US009427458B2

(12) United States Patent
Elizalde

(10) Patent No.: US 9,427,458 B2
(45) Date of Patent: Aug. 30, 2016

(54) METHODS FOR INHIBITING CANCER CELL PROLIFERATION

(75) Inventor: Patricia V. Elizalde, Buenos Aires (AR)

(73) Assignee: Consejo Nacional de Investigaciones Cientificas y Tecnicas, Conicet, Buenos Aires (AR)

( * ) Notice: Subject to any disclaimer, the term of this patent is extended or adjusted under 35 U.S.C. 154(b) by 269 days.

(21) Appl. No.: 13/188,717

(22) Filed: Jul. 22, 2011

(65) Prior Publication Data

US 2012/0021045 A1    Jan. 26, 2012

Related U.S. Application Data

(60) Provisional application No. 61/366,801, filed on Jul. 22, 2010.

(51) Int. Cl.
| | |
|---|---|
| *A61K 48/00* | (2006.01) |
| *A61K 9/127* | (2006.01) |
| *A61K 38/00* | (2006.01) |
| *A61K 38/17* | (2006.01) |
| *A61K 31/138* | (2006.01) |
| *A61K 31/4196* | (2006.01) |
| *A61K 45/06* | (2006.01) |

(52) U.S. Cl.
CPC ........... *A61K 38/177* (2013.01); *A61K 31/138* (2013.01); *A61K 31/4196* (2013.01); *A61K 45/06* (2013.01)

(58) Field of Classification Search
CPC ............. A61K 31/138; A61K 38/177; A61K 31/4196; A61K 45/06
USPC ........................................................ 424/450
See application file for complete search history.

(56) References Cited

U.S. PATENT DOCUMENTS

| | | | |
|---|---|---|---|
| 7,217,737 B2 | 5/2007 | Chen et al. | |
| 2002/0002276 A1 | 1/2002 | Fitzpatrick et al. | |
| 2002/0165193 A1* | 11/2002 | Greene et al. | 514/44 |
| 2003/0053995 A1 | 3/2003 | Hung et al. | |
| 2006/0127928 A1 | 6/2006 | Bacus et al. | |
| 2006/0212956 A1 | 9/2006 | Crocker et al. | |

FOREIGN PATENT DOCUMENTS

| | | |
|---|---|---|
| WO | WO 95-17507 | 6/1995 |
| WO | WO 00-44225 | 8/2000 |
| WO | WO 01-61356 | 8/2001 |
| WO | WO 01-68146 | 9/2001 |
| WO | WO 01-77323 | 10/2001 |
| WO | WO 03-035843 | 5/2003 |
| WO | WO 2004-005320 | 1/2004 |
| WO | WO 2004-087207 | 10/2004 |

OTHER PUBLICATIONS

Davoli et al., 2010, Cancer Chemother. Pharamacol. 65:611-623.*
Chen et al., 2005, Cell Res. 15:504-510.*
Giri et al 2005, Mo. Cell. Biol. 25:11005-110018.*
Hsu et al 2007, JBC 282:10432-10440.*
Schlegel et al 1997, Int. J. Cancer 70:78-83.*
Akiyama et al. "The Transforming Potential of the c-*erbB*-2 Protein is Regulated by its Autophosphorylation at the Carboxyl-Terminal Domain" *Molecular and Cellular Biology* 11(2):833-842 (1991).
Balana et al. "Interactions Between Progestins and Heregulin (HRG) Signaling Pathways: HRG Acts as Mediator of Progestins Proliferative Effects in Mouse Mammary Adenocarcinomas" *Oncogene* 18:6370-6379 (1999).
Bild et al. "Cytoplasmic Transport of Stat3 by Receptor-Mediated Endocytosis" *The EMBO Journal* 21(13):3255-3263 (2002).
Boonyaratanakornkit et al. "The Role of Extranuclear Signaling Actions of Progesterone Receptor in Mediating Progesterone Regulation of Gene Expression and the Cell Cycle" *Molecular Endocrinology* 21(2):359-375 (2007).
Boonyaratanakornkit et al. "Progesterone Receptor Contains a Proline-Rich Motif that Directly Interacts with SH3 Domains and Activates c-Src Family Tyrosine Kinases" *Molecular Cell* 8:269-280 (2001).
Bromberg et al. "Stat3 Activation is Required for Cellular Transformation by V-*src*" *Molecular and Cellular Biology* 18(5):2553-2558 (1998).
Bromberg et al. "Stat3 as an Oncogene" *Cell* 98:295-303 (1999).
Casimiro et al. "ErbB-2 Induces the *Cyclin D1* Gene in Prostate Epithelial Cells In vitro and In vivo" *Cancer Res* 67(9):4364-4372 (2007).
Cicatiello et al. "Estrogens and Progesterone Promote Persistent CCND1 Gene Activation During $G_1$ by Inducing Transcriptional Derepression via c-*Jun*/c-*Fos*/Estrogen Receptor (Progesterone Receptor) Complex Assembly to a Distal Regulatory Element and Recruitment of Cyclin D1 to its Own Gene Promoter" *Molecular and Cellular Biology* 24(16):7260-7274 (2004).
Carnevale et al. "Progestin Effects on Breast Cancer Cell Proliferation, Proteases Activation, and in vivo Development of Metastatic Phenotype all Depend on Progesterone Receptor Capacity to Activate Cytoplasmic Signaling Pathways" *Molecular Endocrinology* 21(6):1335-1358 (2007).
Esteva et al. "Molecular Predictors of Response to Trastuzumab and Lapatinib in Breast Cancer" *Nature Reviews, Clinical Oncology* 7:98-107 (2010).
Faivre et al. "Integration of Progesterone Receptor Mediated Rapid Signaling and Nuclear Actions in Breast Cancer Cell Models: Role of Mitogen-Activated Protein Kinases and Cell Cycle Regulators" *Steroids* 70:418-426 (2005).
Giri et al. "Endosomal Transport of ErbB-2: Mechanism for Nuclear Entry of the Cell Surface Receptor" *Molecular and Cellular Biology* 25(24):11005-11018 (2005).

(Continued)

*Primary Examiner* — Scott Long
*Assistant Examiner* — Kelaginamane T Hiriyanna
(74) *Attorney, Agent, or Firm* — Myers Bigel & Sibley, P.A.

(57) ABSTRACT

The present invention concerns methods of treating cancer and methods of inhibiting cancer cell proliferation, particularly methods of treating breast cancer, wherein the methods comprise delivering a dominant-negative inhibitor of endogenous ErbB-2.

16 Claims, 17 Drawing Sheets

(56) References Cited

OTHER PUBLICATIONS

Guo et al. "β4 Integrin Amplifies ErbB2 Signaling to Promote Mammary Tumorigenesis" *Cell* 126:489-502 (2006).

Hawthorne et al. "ErbB2-Mediated Src and Signaling Transducer and Activator of Transcription 3 Activation Leads to Transcriptional Up-Regulation of p21$^{Cip1}$ and Chemoresistance in Breast Cancer Cells" *Mol Cancer Res* 7(4):592-600 (2009).

Hsu et al. "Nuclear EGFR is Required for Cisplatin Resistance and DNA Repair" *Am J Transl Res* 1(3):249-258 (2009).

Labriola et al. "Heregulin Induces Transcriptional Activation of the Progesterone Receptor by a Mechanism that Requires Functional ErbB-2 and Mitogen-Activated Protein Kinase Activation in Breast Cancer Cells" *Molecular and Cellular Biology* 23(3):1095-1111 (2003).

Leslie et al. "Cyclin D1 is Transcriptionally Regulated by and Required for Transformation by Activated Signal Transducer and Activator of Transcription 3" *Cancer Res* 66(5):2544-2552 (2006).

Li and Shaw. "Autocrine-Mediated Activation of STAT3 Correlates with Cell Proliferation in Breast Carcinoma Lines" *The Journal of Biological Chemistry* 277(20):17397-17405 (2002).

Lin et al. "Nuclear Localization of EGF Receptor and its Potential New Role as a Transcription Factor" *Nature Cell Biology* 3:802-808 (2001).

Lo et al. "Nuclear Interaction of EGFR and STAT3 in the Activation of the iNOS/NO Pathway" *Cancer Cell* 7:575-589 (2005).

Migliaccio et al. "Activation of the Src/p21$^{ras}$/Erk Pathway by Progesterone Receptor Via Cross-Talk with Estrogen Receptor" *The EMBO Journal* 17(7):2008-2018 (1998).

Prat and Baselga. "The Role of Hormonal Therapy in the Management of Hormonal-Receptor-Positive Breast Cancer with Co-Expression of HER2" *Nature Clinical Practice Oncology* 5(9):531-542 (2008).

Proietti et al. "Activation of Stat3 by Heregulin/ErbB-2 Through the Co-Option of Progesterone Receptor Signaling Drives Breast Cancer Growth" *Molecular and Biological Chemistry* 29(5):1249-1265 (2009).

Proietti et al. "Progestins Induce Transcriptional Activation of Signal Transducer and Activator of Transcription 3 (Stat3) via a Jak- and Src-Dependent Mechanism in Breast Cancer Cells" *Molecular and Cellular Biology* 25(12):4826-4840 (2005).

Saitoh et al. "Medroxyprogesterone Acetate Induces Cell Proliferation Through Up-Regulation of Cyclin D1 Expression via Phosphatidylinositol 3-Kinase/Akt/Nuclear Factor-κb Cascade in Human Breast Cancer Cells" *Endocrinology* 146(11):4917-4925 (2005).

Shen et al. "Transcriptional Hyperactivity of Human Progesterone Receptors is Coupled to Their Ligand-Dependent Down-Regulation by Mitogen-Activated Protein Kinase-Dependent Phosphorylation of Serine 294" *Molecular and Cellular Biology* 21(18):6122-6131 (2001).

Sutherland and Musgrove. "Cyclins and Breast Cancer" *Journal of Mammary Gland Biology and Neoplasia* 9(1):95-104 (2004).

Tan et al. "Selective Inhibition of ErbB2—Overexpressing Breast Cancer In vivo by a Novel TAT-Based ErbB2-Targeting Signal Transducers and Activators of Transcription 3-Blocking Peptide" *Cancer Res* 66(7):3764-3772 (2006).

Tsai and O'Malley. "Molecular Mechanisms of Action of Steroid/Thyroid Receptor Superfamily Members" *Annu Rev Biochem* 63:451-486 (1994).

Tzahar et al. "A Hierarchical Network of Interreceptor Interactions Determines Signal Transduction by Neu Differentiation Factor/Neuregulin and Epidermal Growth Factor" *Molecular and Cellular Biology* 16(10):5276-5287 (1996).

Wang and Hung. "Nuclear Translocation of the Epidermal Growth Factor Receptor Family Memebrane Tyrosine Kinase Receptors" *Molecular Pathways* 15(21):6484-6489 (2009).

Wang et al. "Binding at and Transactivation of the COX-2 Promoter by Nuclear Tyrosine Kinase Receptor ErbB-2" *Cancer Cell* 6:251-261 (2004).

Wang et al. "Nuclear Trafficking of the Epidermal Growth Factor Receptor Family Membrane Proteins" *Oncogene* pp. 1-10 (2010).

Xu et al. "Loss of Hsp90 Association Up-Regulates Src-Dependent ErbB2 Activity" *Molecular and Cellular Biology* 27(1):220-228 (2007).

NCI Drug Dictionary. Lapatinib ditosylate. National Cancer Institute. http://www.cancer.gov/drugdictionary?CdrID=269659. Downloaded May 7, 2014. 1 page.

Li, C. et al., "Nuclear EGFR contributes to acquired resistance to cetuximab", *Oncogene* (2009), vol. 28, pp. 3801-3813.

Dittmann, Klaus et al., "Inhibition of radiation-induced EGFR nuclear import by C225 (Cetuximab) suppresses DNA-PK activity", *Radiotherapy and Oncology*, vol. 76 (2005), pp. 157-161.

Wang, Shao-Chun et al., "Binding at and transactivation of the COX-2 promoter by nuclear tyrosine kinase receptor ErbB-2", *Cancer Cell*, Sep. 2004, vol. 6, pp. 251-261.

Konecny, Gottfried E., et al., "Activity of the Dual Kinase Inhibitor Lapatinib (GW572016) against HER-2-Overexpressing and Trastuzumab-Treated Breast Cancer Cells", *Cancer Res.*, Feb. 1, 2006, vol. 66, pp. 1630-1639.

Rusnak, David W., et al., "The Effects of the Novel, Reversible Epidermal Growth Factor Receptor/ErbB-2 Tryrosine Kinase Inhibitor, GW2016, on the Growth of Human Normal and Tumor-derived Cell Lines in Vitro and in Vivo", *Molecular Cancer Therapeutics*, Dec. 2001, vol. 1, pp. 85-94.

* cited by examiner

C4HD cells

| MPA 10 nM (min) | 0 | 5 | 10 | 15 | 30 | 60 | 120 | 30 | 30 | 30 |
|---|---|---|---|---|---|---|---|---|---|---|
| RU486 10 nM | - | - | - | - | - | - | - | + | - | - |
| PR siRNA 25 nM | - | - | - | - | - | - | - | - | + | - |
| Control siRNA 25 nM | - | - | - | - | - | - | - | - | - | + | pErbB-2 (Tyr1272)
ErbB-2
pErbB-2 (Tyr927)
ErbB-2

C4HD cells

| PR siRNA 25 nM | - | + |
|---|---|---|
| Control siRNA 25 nM | + | - |

PR
βTubulin

T47D cells

| MPA 10 nM (min) | 0 | 5 | 10 | 15 | 30 | 60 | 120 | T47D-Y 0 | T47D-Y 30 | T47D-Y-PR-B 0 | T47D-Y-PR-B 30 |
|---|---|---|---|---|---|---|---|---|---|---|---| pErbB-2 (Tyr1222)
ErbB-2
pErbB-2 (Tyr877)
ErbB-2

C4HD cells

C4HD cells

C4HD

C4HD-hErbB-2ΔNLS

METHODS FOR INHIBITING CANCER CELL PROLIFERATION

STATEMENT OF PRIORITY

This application claims the benefit, under 35 U.S.C. §119(e), of U.S. Provisional Application Ser. No. 61/366,801, filed Jul. 22, 2010, the entire contents of which are incorporated by reference herein.

FIELD OF THE INVENTION

The present invention concerns methods of treating cancer and methods of inhibiting cancer cell proliferation, particularly methods of treating breast cancer.

BACKGROUND OF THE INVENTION

Progesterone receptor (PR) and the ErbB family of receptor tyrosine kinases are major factors in breast cancer. In its classical mechanism of action, PR acts as a ligand-induced transcription factor. Upon progestin binding, PR translocates to the nucleus and binds to specific progesterone response elements (PREs) in the promoter of target genes (27). In addition to its direct transcriptional effects, PR activates signal transduction pathways in breast cancer cells through a rapid or nongenomic mechanism (5,19).

On the other hand, the ErbBs family of membrane receptor tyrosine kinases is composed of four members: epidermal growth factor receptor (EGFR/ErbB-1), ErbB-2, ErbB-3, and ErbB-4. ErbBs ligands include all isoforms of heregulins (HRG), which bind to ErbB-3 and ErbB-4 and recognize EGF-R and ErbB-2 as co-receptors, and the epidermal growth factor (EGF) which binds to EGF-R (28). Upon ligand binding, ErbBs dimerize and their intrinsic tyrosine kinase activity is stimulated, which leads to the activation of signal transduction pathways that mediate ErbBs proliferative effects. Although ErbB-2 is an orphan receptor, it participates in an extensive network of ligand-induced formation of ErbBs dimers. ErbB-2 has been shown to migrate to the nuclear compartment where it binds DNA at specific sequences, HER-2 associated sequences (HAS) (30). Through this function as a transcription factor, ErbB-2 modulates the expression of the cyclooxigenase-2 (COX-2) gene (30). Association of ErbB-2 with the COX-2 promoter was detected in breast cancer cell lines overexpressing ErbB-2, as well as in ErbB-2-positive human primary breast tumors (30). Overexpression of ErbB-2 is associated with increased metastatic potential, poor prognosis, and therapeutic resistance in mammary tumors.

The present invention addresses previous shortcomings in the art by providing methods of treating cancer and methods of inhibiting cancer cell proliferation, particularly methods of treating breast cancer.

SUMMARY OF THE INVENTION

A first aspect of the invention is a method of treating cancer in a subject, comprising delivering to a subject in need of such treatment a mutant of ErbB-2 in an amount effective to inhibit cancer cell proliferation, wherein the mutant cannot translocate to a nucleus of a cell in which it is present and functions as a dominant-negative inhibitor of endogenous ErbB-2.

A second aspect of the invention is the use of a mutant of ErbB-2 for carrying out a method of the present invention.

A further aspect of the invention is the use of a mutant of ErbB-2 for the preparation of a medicament for carrying out a method of the present invention.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

DETAILED DESCRIPTION OF THE INVENTION

Figure 1A:
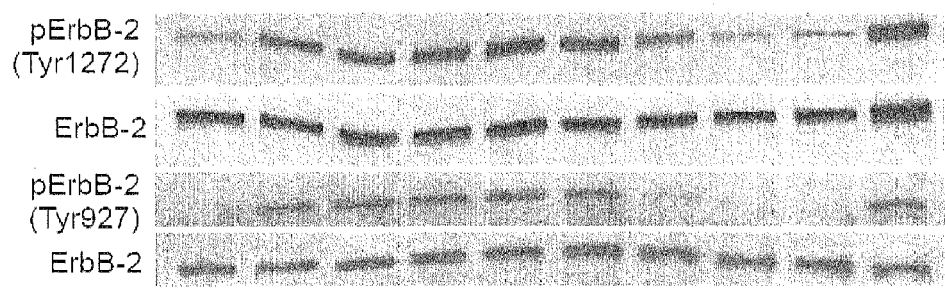
FIG. 1 MPA effects on ErbB-2 and Stat3 activation and cellular localization (A) MPA induces rapid ErbB-2 phosphorylation via the classical PR. Cells were treated with MPA or pretreated with RU486 and transfected with PR or control siRNAs before MPA stimulation. Western blots (WB) were performed with phospho(p) ErbB-2 antibodies and filters were reprobed with a total ErbB-2 antibody. The WB in the lower panel of C4HD cells shows the effects of siRNAs on PR expression. (B) c-Src mediates MPA induced ErbB-2 activation. Cells were treated with MPA or preincubated with PP2 before MPA treatment. WB were performed with phosphoprotein antibodies and membranes were reprobed with total protein antibodies. (C) MPA induces ErbB-2 nuclear migration. Top: Cells were treated with MPA for the time-points shown and nuclear and cytosolic protein extracts were analyzed by WB. The pTyr1272/1222 ErbB-2 blot was reprobed with the ErbB-2 carboxy-terminal region antibody (C) and the pTyr927/877 blot with the antibody to ErbB-2 amino (N) terminus. Total cell lysates were blotted in parallel. Histone H3 and β tubulin were used to control cellular fractionation efficiency. Bottom: WB blot showing that inhibition of ErbB-2 phosphorylation with AG825 blocks ErbB-2 nuclear migration. (D) MPA induces Stat3 activation via ErbB-2. Cells were treated with MPA or pretreated with AG825. C4HD cells were also transfected with ErbB-2 siRNAs targeting mouse ErbB-2 and with control siRNAs. WB were performed with phospho antibodies and filters were reprobed with the respective total protein antibody. (E) MPA stimulates Stat3 nuclear translocation. Nuclear and cytosolic protein extracts were analyzed by WB with pStat3 antibody. Blots were reprobed with total Stat3 antibody. Experiments shown in A to E were repeated five times with similar results.
Figure 1A:
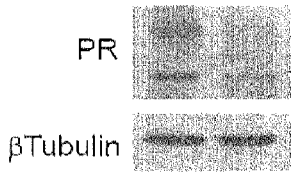
Figure 1A:
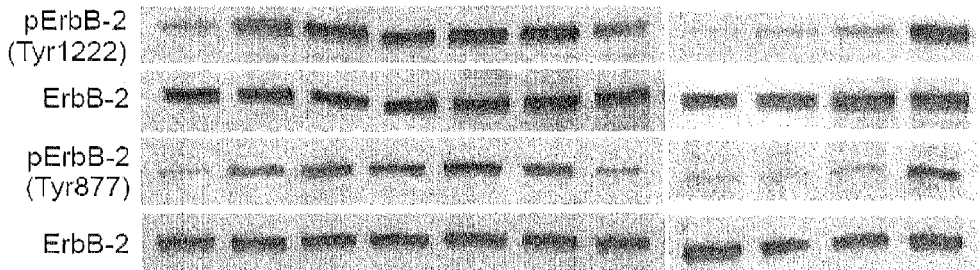

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, *In re Herz*, 537 F.2d 549, 551-52, 190 U.S.P.Q. 461, 463 (CCPA 1976) (emphasis in the original); see also MPEP §2111.03. Thus, the term "consisting essentially of" as used herein should not be interpreted as equivalent to "comprising."

The term "about," as used herein when referring to a measurable value such as an amount or concentration (e.g., the amount of overexpression of ErbB-2) and the like, is meant to encompass variations of 20%, 10%, 5%, 1%, 0.5%, or even 0.1% of the specified amount.

I. Definitions

"ErbB-2" as used herein refers to the tyrosine kinase receptor ErbB-2 that belongs to the epidermal growth factor receptor family. ErbB-2 can be natural or synthetic (e.g., derived from PCR and/or recombinant DNA techniques). ErbB-2 can be from a mammal, such as a human. As recognized by a skilled artisan, nucleic acid sequences and/or amino acid sequences useful to the present invention can be obtained through publicly available databases, such as the National Center for Biotechnology Information (NCBI) database or commercially available databases, such as from Celera Genomics, Inc. (Rockville, Md.). Sequence information for ErbB-2 can be found at NCBI Gene ID: 2064. An exemplary wild-type ErbB-2 nucleic acid sequence is NCBI GenBank Accession No. NG_007503.1 (SEQ ID NO:1) (Table 1).

TABLE 1

Exemplary wild-type ErbB-2 nucleic acid sequence, GenBank Accession No. NG 007503.1 (SEQ ID NO: 1)

```
  1 agttcccgga ttttgtgggg cgcctgcccc gcccctcgtc ccctgctgt gtccatatat
 61 cgaggcgata gggttaaggg aaggcggacg cctgatgggt taatgagcaa actgaagtgt
121 ttttccatgat ctttttgag gtagggctgt ttactgtcac caccoctgtc ggattttact
181 tcctaaacgt acctgtaact atccacttct ctccatctct tctggcacca ccctggttaa
241 agacaccatc atgtgtcgcc aagacagccg cagtagcttc ttaatggctc tccctgcctc
301 tacttttgcc tcttccaacc tgcgctccat tttgaaaaat taaaatttgc ccatatcact
361 ttttttttct taaaattatt tactggctcc caattacctt gggtaaaata cagtctccac
421 aaaccctgcc tgatttggcc cctgtccact ggtctccctc actcccttgc tccagacccg
481 cttcagaggg ctatgtccct caagcttcct gactgcctgg cctggtctga atcactcact
541 cttctttttt cttctagtcg caattgaagt accacctccc gagggtgatt gcttccccat
601 gcggggtaga acctttgctg tcctgttcac cactctacct ccagcacaga atttggctta
661 tggtaggcgc taactgcgtt tgtttgttct tctgtttaat gaatgaacag catacatcaa
721 cataagaact tgacaaatcc agggctgtaa aatcatcagt atggttctgc actgagatcg
781 gagagaagta atatttctag gaaaattagg aaccctggga acaggacgct tgctttagta
841 tcctctccct gctcacctcc cctgcactcc catcagcacc gacccacacc caatctcata
901 gaagccttgt agctaaggat caccctttct cctcccccac tctcctcacc ccttgtcaac
961 ttttctttt cgtcctgggg gttggaatga gtaagaagta gcctgggatt ccattcactc
```

TABLE 1-continued

Exemplary wild-type ErbB-2 nucleic acid sequence, GenBank Accession No. NG 007503.1 (SEQ ID NO: 1)

```
1021 acttaacaaa catttctgag tccttagctc tagcaccttg ctaagcaagg caaaatctcc
1081 aggaggcacc attcacattg cattttctgt gaatggtgct ctggggagca gcattcacat
1141 tgccttttct gtgaatggca aattcttcca gttaaatata acatgaatag tgtccctgg
1201 agttgaccac ccaactgata ctgactgaga agctgaaatg aacaaaacaa cccttagcc
1261 ctccaggagc tgaccggaaa tccagtgcta atactacttt gcatcttaca gattagttct
1321 tttacaatac tgttttttt tcttttttca tttcattttg tcctttctgt gactctggga
1381 tgagtctttt tatgaggatc ctcatataaa gatggacatt taggattaaa gaggatgaaa
1441 tcctgacaaa atagggagtc tccccttag aaaattccta agtaaggctg ggggtggtgg
1501 ctcacgcctg taatcccagc actttgggag gccgaggcgg acggatcacc tgaggttagg
1561 agtttgagac cagcctgacc aacatggaga accccatct ctactaaaaa tacaaaatta
1621 gttgggtgtg gtggtgcatg cctgtaatcc cagctactca ggaggctgag gcaggagaat
1681 cgcttgaacc cagggaggca gaggttgtgg tgagccaaga ttgcgccatc gcactccagc
1741 ctgggcaaca agagcgaaac tcaaaaaaaa aaaaaaag aaaagaaaa ttccaatttt
1801 gaaggcctca tcctatatta tgtcaaacat actgaaatgc agtaacgccc cacattaaat
1861 aagatttata ataactata catatatata attcaatcta attgctgtta atagttgaca
1921 tattgctaca tttatataca tttagttaaa aaaaattttt tttcccagac agcctctcac
1981 tctttcacct agactgaagt gcagtggcat gatcacgact cactgcaacc tcaacctccc
2041 agactcaagt gatccttcca tctcagcctc ctgagtagct gggactgcag catgcgccac
2101 tatgcccctgc taattttttt aattttttgt agagacacgg tcttgctatg ttgcctagac
2161 tggtctccaa ttcctgggct cgagtgatcc tcccgcctca acctcccaaa gtgctgggat
2221 tacgggcgtg agccatgcca cacggccata aatatttaat tttcgcagct ttcttatatt
2281 ttagaactaa caatggaaat ttgttcgggt ctaaagtatt tcagaggtcc ttgaaaaccc
2341 atgcctacat acctgatgga aaagcaatc ctaggttaat ggtggaagtg ggagtagaga
2401 cttctgttct gttgacttct tggaagatgg ggtactgtct ctctgggaca gctcttgaga
2461 atttcccctgc cagcacagcc ccagataaca atctctagat ggcgattacc tggcctctct
2521 tcccaacttt ctagcctgga gcccctagtt ctcccctgag cctccttagc ttgtccttct
2581 tcctaacttg tatttggctt cagatgtgat ccacagtctg aaaagtcact aattcattcc
2641 ttcaactcag gcttattgag tcctcctgtg tatcagccat tgtactcatg ggggaaaaaa
2701 aagacaaagc atatgttaat agtagagtgt gctggacagg cacagtggct catgcctgta
2761 atcccagcac tttgggaggg cgaggcaggt ggatcatctg aggtcaggag ttcgagacca
2821 gcctgaccta acatggagaa actcctgaga tcgtgccatt gcactccagc ctgggcaaca
2881 agagcaaaac tccgtttcaa aaaaaaaaa aaaagtatag tgtgctaaag gctcaacggc
2941 aagctgacca tgttcttaga tcaaaattgg tagagagtct acaatgtggg ttccttattc
3001 atcaaatgtt tattaagttt accatgtgca agtctctggg aacagagtga tgaacaaggc
3061 actgtacttt tcatggtcag aggagggaaa caggccataa acaagtgtca aacaaaagac
3121 tgaagccagg tgcggtggct cacatctgta atcccagcac tgtgggaggc caaggcaggc
3181 ggatcatgag atcaggagat cgagaccatc ctagccaaca tggtgaaacc ccatctctac
3241 taaaaataca aaaaaattag ctgggcatgg tggcacgtgc ctgtaatccc agctactccg
3301 gaagctgagg caggagaatt gcttgaacca gggagttgga ggttgcagtg agcctggatt
```

TABLE 1-continued

Exemplary wild-type ErbB-2 nucleic acid sequence, GenBank Accession No. NG 007503.1 (SEQ ID NO: 1)

```
3361 atgccactgc actccagcct ggtgacagag cgagactcca tctacattaa aaaaaaaaat
3421 atatatatat atatatacac acacacacac acacacacac acatacccto taacccagga
3481 atttcactcc taggtatacc tacataagct ccagtatacc taaacaagtg caaatttgtt
3541 taagtacagt tatttgtggt agcattagtc attgttttca atagcaagaa gaaaaaggaa
3601 acaactaaat gtccatcaat agggaatgaa ttatattaat ggagggagag ccatacaatg
3661 gaaggctgaa cagaaattaa taggaatggg gcagatttgt aatgtactag catggtaaaa
3721 ccttcatgat agatatagat atagatatag atatagatat agatatatat acatatacat
3781 atacatatac atatacatat atatatatat atatatatat ctcttgtgtc tcagcctccc
3841 gagtagctgg gattacaggt gtgtgccacc acatccggct aattttttgta ttttttagta
3901 gagacagggc ttcaccatgt tggtaaggct gtcttgaact cccgacctca ggtgatccac
3961 ctgtctcagc ctcccaaagt gctgggatta taggcatgag ccatcacacc tggccaaata
4021 ttttttgataa gtatcaagtg cacagtgcag aacaaaatat gtgtgtgtgt atgcatgtgt
4081 atgtacacct atacacttat atacagtacc ccatgtgaag aaaaataagg gtacgtgtta
4141 tgcgcgtagt attatggttg ttattttga gaatatatct agaaagataa aaagaaagt
4201 ggaaatagtt cttgcctctg gtgggaagtg ggactatgtg cctgatcaat agggaagtaa
4261 ggaacacttt tttttttttt tttaaacgg agttttgct cttgttaccc aggttggagt
4321 gcaatggcgc gatcttagct cactgcaacc tctgcctccc aggttcaagc gattctgctg
4381 cctcagcctc ctgagtagct gggattatag gcatgcgcct ccacgcctgg ctaattttgt
4441 atttttttagta aagatggggt ttctccatgt tggtcaggct ggtcttgaac tcccacctc
4501 aggtgatccg tccgcctcag cctcccaaag tgctaggatt acaggcgtga ccaccgtgc
4561 ctggccagga acgcttttta tttttgtacc tttaaaagtg tgtaccgtct gtgtatataa
4621 tcagttaaaa acaaagaaaa gctgagtgtg gtggctcatg cctgtaatcc cagcccttaa
4681 ggaggccgag gccggcggca gatcacctga ggtcaggagt tcaagaccgg cctgaccaaa
4741 acggtgaaaa ctcatctcta caaaaacata aaaattagcc aggcatgatg gcaagtgcct
4801 gtaatcccag ctggttggga ggctgaggtg ggagacttgc ttgaacctag gaggcagaga
4861 ttgcagtgag ccaagactgt accactgcac tccagcctgg gcaacagagc aagtctctgt
4921 ctcaaaacaa aaacaaaaac acaaagaaaa aatgtaaaac aatttcatgc agtagcaagc
4981 atcgagttaa atacagttga cccttgaaca acacaggttt gaattgcacg ggtccattta
5041 tactcacatt tcttccacct ctgccacccc caaaatagca agaccaaccc catctctttt
5101 cctttctctt cccctcctc agcctactca atgtgaagat gatgaggatg aaaacctttg
5161 tgatgatcca cttccactta atgaatggta aatatgtttt ttcttactta tgatttcctt
5221 agtagcattt tcttttctct agcttccttt attgtaaaaa tacagtatat aacacatatc
5281 acatacaaaa tgtgtgtaaa tggactgttt gctattgata agtattctgg taaacagtag
5341 actattagtt ttttttgttt tgtgacaagg tctccctctg tcgcccagcc tggaatgaag
5401 tggtgtgatc atggctcact gcagccaaaa acttctgggc taaagcaatc ctctactaaa
5461 aatacaaaaa ttagccaggc atggtggtgc gcttctgtaa tcccagctac tcaggaggct
5521 gaggcaggag aattgcttga acccgggagg cagaggttgc agtgagctga gattgcaccg
5581 ttgcattcca gcctggacaa cagagcgaga ctccatctcg aaaataaaat aataataata
5641 ataataataa taataataat aataataggg ctgggtgtgg tggctcatgc ctgtaatccc
```

TABLE 1-continued

Exemplary wild-type ErbB-2 nucleic acid sequence, GenBank Accession No. NG 007503.1 (SEQ ID NO: 1)

```
5701 agcactttgg gaggccaagg tggacagatc acctgaggtc aggagtctca attaaaaaat
5761 aaataggccg ggcacagtgg ctcatgccca taatcccagc actttgggag gccgaggtgg
5821 gcagatcacc tgaggtcagg agtttgagac cagcctggcc aacacggaga aacgctgcct
5881 ctatcaaaaa tacaaaaatt agctggatgt ggtggtgcat gctataatcc cagtaatacc
5941 agctactcgg aaggctgagg caggagaatc actcgaatcc gggacacgga ggttgcagtg
6001 agccgacatc atgccactgc gctccagcct gggtgacagt gagactctgt ctcagaaaaa
6061 aaaaaaaaaa aaaaaaaaa aaaaaaaat atatatatat atatatatat atatatatat
6121 atatatatat gtgtgtatat atatatatat acacatatat atgtgtatat atatatacac
6181 acacacatat atatgtgtat ataaaaata aaataaataa taataaaaca tttactttgg
6241 ctgctgttgc tgcggggaga attgcagggt gtcaaaagta gcactggtgg aggggtagtg
6301 atcaaagtct ggtgctttag cccaaaggag aaatgataga gactcagact agctggtgat
6361 ggaggtagaa taagcataaa tgtatcaaaa agaggagttg atagatctta aagaatgatt
6421 ggatttgaag ggcaaaggaa gagaagaatc aaccaggtgg gttcagtgaa tgaaaccatc
6481 agaaacgaat tgtcccctga aatcaagact ttgtgattgc catagttgta tgcttctcaa
6541 aggttcctcg tctcctcttc cttggaccaa aagtcagagg caagaatgcc ctcattcata
6601 ccccagtggt ctatacctcc agcagcaagt cgagtgagca agtgatgtcc tgaaaggccc
6661 agtggatcag tggaatgaag cgggcaggaa gacttagtgc tcctgaaaca aggaatccag
6721 aatccaggag aaggatggct cagtggggct ttcaagggac aagtatgggg gttgaagggg
6781 tcactgtccc tataccaaat ccgaaaatat tgtgacaagg aaccattctg tccaactctt
6841 ctatttcagg tggcaaagca aagctatatt caagaccaca tgcaaagcta ctccctgagc
6901 aaagagtcac agataaaacg ggggcaccag tagaatggcc aggacaaacg cagtgcagca
6961 cagagactca gaccctggca gccatgcctg cgcaggcagt gatgagagtg acatgtactg
7021 ttgtggacat gcacaaaagt gaggtgagtc gcaggacaga agagtgcttt ttgtttcagc
7081 agagcagcct ggggagagat aaaagctact cctggggcct gggcctgcat tcctgagatg
7141 tgggtaagag gggcccaggg tcagagtgtc tggcaagctt ggctctgccc ctttgctgtc
7201 ctggagacta gggctaatcc tgggctcagg gagtggcctc cccatggtta ggatacaagt
7261 gctcatcaag ggccacccct aggaaggacc aattttccta tcagaagctt ctaagttatc
7321 ctccttttgc ccaaagggac acctcaagcc tactctgagg aactctttcc aatgaactaa
7381 ttcctacagt cacttcccca gcaacctgtg cctcagcctc aaggcactgt ggggtaggcc
7441 tcagtttgtg gcctggacat cggactgtgg accagacgac tcctcccgat ttctgtttgt
7501 ttttcagtcct ctgaccccaa gctggctggt gaagtaggta gagggaggag actttggtgc
7561 atgcatacac acacacacac acacacacac acacacacac acacacacac acacacacac
7621 gtctcctgtg cccccagtc tccatggctg tcaatgatt gactggcatt tcacaggccg
7681 ctggttgcag cccagcctg ttgacttaga ggtcaccctc ggaagctaga gccctgtcct
7741 gcctcttcag tgtcagtggt cactccactg cccacaggct ggggtcttgg gcaaaacaca
7801 cgcatctgcc ctgatctgag tttgctgccc tctgtcccgc agtcagcccc actctgttcc
7861 cactccctct ccccagcccc ctagctagac ccctctcacc agcaccccct tcccttccct
7921 gagggtcccc ctcgctgtct ttgtccctca gacatcctct ttcctgggct ctcctgccag
7981 gccctgctgg agggacagtt aaggaggaaa tcgaatcagc agcgcccacc cctgcccccc
```

TABLE 1-continued

Exemplary wild-type ErbB-2 nucleic acid sequence, GenBank Accession No. NG 007503.1 (SEQ ID NO: 1)

```
 8041 ttcctctcct cttgtcagac accagacgag gttttttcct ctggcttccc agctctgaat
 8101 gggctcattc tttttcagag gctcggcccc tctcgagcct cctccccagg gcgtgagttc
 8161 tgaccccagc tcctccccccc atccccactc cagccccctc tccagcttgc tccaccctct
 8221 ctaccgccca ccgggactgg gcattgtctg ccagtccggg tttcttcctg ggatttggga
 8281 tgcagagagg atgggtttgc ttgggcgggg gggtggagag tgaaggggggg aagcaggatc
 8341 ttttgtagagg gagggaccta cagttacctg gacttctttc ctctgtctcc cctcttggta
 8401 cccttgactg gggctcttga gggtaatggg tgaagccaaa tctgccatgg ctcagttccc
 8461 agctcagctc tgtgaccttg ggaaagttcc tttagctcgt ggaatctcaa ggctcaaggt
 8521 tcctcttctg caaaatgggg aatgataaca cctgcctcct ctggagtctt ggggactcag
 8581 tgttctgagg aacgtggctg taggtcagag tggcacagag tagggtccaa tgaagcatgg
 8641 cgtccacagt agctttcctg actggactaa cctttccgga cacaacagca gggcaggggt
 8701 ggggcctggg gagaaaggac acctctaacc ctgatcctaa catcccgatg gcctctaagg
 8761 ctgcctgcac actcatccag gtgcaagccc tccaaggtgt ggtgtgatga accagtgact
 8821 cctggagcca ggtcagcgca tcctcttccc gcagggctgt aagctgcagg actgagaggc
 8881 aggttgacca ggtcctgggc tggatgatgg ggtgagagta aggggtcagt tttgatacat
 8941 gcccaacttt tctctctagc cctaagacat cctgggcaaa ttgcttacct cagttccct
 9001 gatcctcacc ctaaccctaa caccagctca agagaaaata gggatattga tggccatcca
 9061 gaagggctgc tgtgttccat acacagcaat atttctcgaa tgtttgtgac agcggtccaa
 9121 ggaataagtt aattttacat tatcactctg gatacctgta caaaactcca ccttatcctt
 9181 actatatgaa tgtgctaggg ttgttttttt gttttgtttt ttttttttt ttttgagaca
 9241 gagtttcgct cttgttgccc aggctggagt acaatggcgc gatcttggct caccgcaacc
 9301 tccgcttccc aggttcaagc gattcacctg cctcagcctt cccgagtagc tgggattaca
 9361 ggcatgcgcc accatgcccg gctaattttg tgtttttagt agagacaggg tttctccatg
 9421 ttggtcaggc tggtaccaaa ctcccgacct caggtgatcc acctgccttg gcctcccaaa
 9481 gtgctgcaat tacaggcatg agccaccgca cccagccgtg ctagggtctt tttctgttca
 9541 attccttct ctctcttgct ctctttcttt ctttcaatgg agtcttactc tgtcacccag
 9601 gctggagtgc agtggcaaga tctcagctca ctgcaacctc tgccctctga gttcaagcaa
 9661 ttctcctgcc tcagcctccc gagtagctgg gattacaggt gcctgccacc acacctagtt
 9721 aattttttgta ctttagtag agatggggtt ttgtcatgtt ggccaggctg gtctcgaact
 9781 cctgacctcg tgatctgcct gtcttggcct cccaaagtgc tgggattaca ggcatgagcc
 9841 gccatactcg gccaactttg tattactttc ttaaagagag tttcccaaat tatataagct
 9901 tcaggcccca caaacctag atctgcccca gtataactaa atctgggacc atttattgag
 9961 caattattat gtgccaagta ttgcgctgag tgcttccaga gcattatctc ctttaaccc
10021 agcatagtat gtcagatgct gttttacaga tgagccaact gagaccagag atgctcagtc
10081 acttgcccaa ggtgacatga ctgatatgga atagagtcaa gatttttttt tttttttttg
10141 acacggagtc tcactctgtc tcccaggctg gagtgcagag gcgcaatctc agctcactgc
10201 aagctctgcc tcccaggttc acgccattct cctgcctcag cctcctgagt agctgggact
10261 acaggcaccg ccaccacac ctggctaatt ttttgtattt ttagcagaga cagggtttca
10321 ccgtgttagc caggatggtc tcgatctcct gacctcgtga tctgcctgcc tcggcctccc
```

TABLE 1-continued

Exemplary wild-type ErbB-2 nucleic acid sequence, GenBank Accession No. NG 007503.1 (SEQ ID NO: 1)

10381 aaagtgctgg aattacaggt gtgagccacc gcgactggcc agattcaaga tttgaaccca
10441 ggtcctcttg gtcccagagg ccctgtttc tcaactccct aggatggcat agcaacctgt
10501 cccacaagag gtgcctgctt taagtgtgct cagcacatgg aagcaagttt agaaatgcaa
10561 gtgtatacct gtaaagaggt gtgggagatg ggggggaggg aagagagaaa gagatgctgg
10621 tgtccttcat tctccagtcc ctgataggtg cctttgatcc cttcttgacc agtatagctg
10681 cattcttggc tggggcattc aactagaac tgccaaattt agcacataaa ataaggagg
10741 cccagttaaa tttgaatttc agataaacaa tgaataattt gttagtataa atatgtccca
10801 tgcaatatct tgttgaaatt aaaaaaaaaa aaaaagtct tccttccatc cccaccccta
10861 ccactaggcc taaggaatag ggtcagggc tccaataga atgtggttga gaagtggaat
10921 taagcaggct aatagaaggc aaggggcaaa gaagaaacct tgaatgcatt gggtgctggg
10981 tgcctcctta aataagcaag aagggtgcat tttgaagaat tgagatagaa gtcttttgg
11041 gctgggtgca gttgctcgtg gttgtaattc cagcactttg ggaggctgag gcgggaggat
11101 cacctgaggt tgggagttca agaccagcct caccaacgtg gagaaaccct gtctttacta
11161 aaaatacaaa aaattagctg gtcatggtgg cacatgcctg taatcccagc tgctcgggag
11221 gctgaggcag gagaatcact tgaaccaggg aggcagaggt tgtggtgagc agagatgcg
11281 ccattgctct ccagcctggg caacaagagc aaaagttcgt ttaaaaaaaa aaaaaagtcc
11341 tttcgatgtg actgtctcct cccaaatttg tagaccctct taagatcatg cttttcagat
11401 acttcaaaga ttccagaaga tatgccccgg gggtcctgga agccacaagg taaacacaac
11461 acatccccct ccttgactat caatttact agaggatgtg gtgggaaaac cattatttga
11521 tattaaaaca aataggcttg ggatggagta ggatgcaagc tccccaggaa agtttaagat
11581 aaaacctgag acttaaaagg gtgttaagag tggcagccta gggaatttat cccggactcc
11641 gggggagggg gcagagtcac cagcctctgc atttagggat tctccgagga aaagtgtgag
11701 aacggctgca ggcaacccag gcgtcccggc gctaggaggg acgcacccag gcctgcgcga
11761 agagagggag aaagtgaagc tgggagttgc cactcccaga cttgttggaa tgcagttgga
11821 gggggcgagc tgggagcgcg cttgctccca atcacaggag aaggaggagg tggaggagga
11881 gggctgcttg aggaagtata agaatgaagt tgtgaagctg agattcccct ccattgggac
11941 cggagaaacc aggggagccc cccgggcagc cgcgcgcccc ttcccacggg gccctttact
12001 gcgccgcgcg cccggccccc accctcgca gcacccgcg ccccgcgccc tcccagccgg
12061 gtccagccgg agccatgggg ccggagccgc agtgagcacc atggagctgg cggccttgtg
12121 ccgctggggg ctcctcctcg ccctcttgcc cccggagcc gcgagcaccc aaggtgggtc
12181 tggtgtgggg aggggacgga gcagcggcgg gaccctgccc tgtggatgcc ccgccgaggt
12241 cccgcggccg gcggggccag aggggcccgg acgagctctc ctatcccgaa gttgtggaca
12301 gtcgagacgc tcagggcagc cgggccctgg ggccctcggg cgggaggggg cagttacacg
12361 gcagcggctc gagatggccc atccaagaga ctggcgcttt ccaggctccg aggggctccg
12421 ggaacttgtc aaagaagttc tctgaaattg ttcagaaagt tttcccgcaa agggtgtatt
12481 gcgtagagcg cgcgcgcgcg tttccccct tcttgagccc cctcaagctt tctcaaagcc
12541 tttccagttg gcagcctccg cctccggact ggcctgggct ggattccttg gggggtcct
12601 ctgcccctgcc cctcctccag cccctccccg ctcccttca gacgattttg gtttggttgc
12661 tcctgcttct ggcggggtcg ggtgtgtgtg tgtgtggtgg agtggagggt ggcatagcaa TABLE 1-continued Exemplary wild-type ErbB-2 nucleic acid sequence, GenBank Accession No. NG 007503.1 (SEQ ID NO: 1)

```
12721 cctgtcccaa ccagagccgg ggaggaaagg gtggcccgga gggtggcctc ttgctggggt
12781 ctgggttggg ggcggggggag acgtttgctt tgaacagatt cttggggcca gcttagggac
12841 tgtgctctgt gacttttgga gcgcgtggac catggagggg tgggggtggg tttcttgggg
12901 tgtaaagtgg gagagttccc agagaaggaa gctaagaaat aaggccagat gggagcctag
12961 ggagggctgc gttgttctgc tgccttttcc ttggtgctgt gcgtggggaa gggtgagtgg
13021 gggcagtgtg tatcctgacc catctgtcca cctgtgtgca ttaatcataa agctaacat
13081 atagcctggg ccaggtatac tctgccagga actgtttgtg gtgttttgca tgcattctcc
13141 tttaatccta gaacacccct atagtggaag ttctgccagc attctggact gagtagcagt
13201 ccagaggttg agtagcagct agtaagtggt ggggtcaaga tgggacccca ggcagtgcga
13261 cccccaacca tgcattcgaa atcgctatat ggatgagtgc acctggagca atgagggaca
13321 ctgctccctg agtcactggg ctgcagggga gacaaaatga aagtgttctg ggagtcgtgg
13381 gtggtctcca taggtcagag ggtctgggga gggagtgggt gtcatcgtgg ctgtgtgttg
13441 cccgaggggc cctctgtgag tgagtgcatg gccgtgttat tctgcaggt ctacgccagg
13501 gtgttcctca gttgtgtggt ctttgtattt gtgtgtctgg gctttgtgtt gccaaacagc
13561 agtctctctg ctgacttggg gacacaggct gaactctgtc ctctgcagga actcccttaa
13621 ggtgctgggc cagatctgcc ataaacagag ggaggtagcc ttctatggcc acgccttctt
13681 gctgaggaag aaggttcctc tcttccaggg agtacatcct tgccctcccct gtttcccaga
13741 caagcatctt cacctctcat cttctgatga aagggtgag gccatactga gctgtcaggc
13801 tgagctgctg cccttcctca ccttgggctg ggagttgatc agggaatggc agttgctgca
13861 gagctggatt tgagggctgg gttctctgga tgggcctcc tcatgtcctc accccctcaac
13921 ctgcactatt gattgtgttg tgcaggagtt agttaaaaag tcattgcaca gcctgggcaa
13981 caaggcaaaa ctctgtacaa aaaatacaaa aattagttgg atgtgattac acgtgcctgt
14041 agtcccagct actccggagg ctgaggcagg aggatcacct gagcccagga agttgaggct
14101 tgcagtgagc tgtgattgca aatgctctcc agcctgggtg acagtgtgag actccgtttc
14161 agaaaaaaag tataccaccc agctgcctcc agcacccaga tttacccaa ggggtgaggt
14221 ctggggcagg aatgtggggg aagggggaggc ctaggggag ccccagaggg gtcaggattt
14281 ttctgaaatc ctttcttaga ggtatggggtt ttacaaattg cagcaaatac atcctttta
14341 tcttgcagaa ctccttcata ttttaattcc agtatgattc ttccaacagc ctcctctctt
14401 tactatactt ggggaaagta ctcattttat ttgtcaagaa aaaaacaatt gaaaagatag
14461 ggatcaaatg taaaaagaaa aaatacgtgg cattccaaag tcaaacacaa agcatgttta
14521 attttctcgt ggtttgggat tacccatatt cctgctgtat gaacctgtct tgtcttaact
14581 ttttaagaaat gtacggtgta cttcctatat gctaggtttt tatccatgct ttcatttaat
14641 ctctgtgaca gtcctgtgaa gtaggtgcac agatgagaaa atggaagttc agagaaatga
14701 agcaacttat ccaaggctcc cagctaccca gtaatgtcca gggaattttt ggactctgaa
14761 gaggaggcat taagaggtgg ttagagtctt attccagcca acaataatgg gttgaacaaa
14821 gccttagggg caggcaggtg gccagatggg aggagaagcg ctcctcttgt tcaggcgaat
14881 gacctttcca tccacttctc taggctgtag aaagtggagc tgagctgggg gccctgaggt
14941 tccctcttga cttcagagtc ctctcccttc ctgtccagcc aatgcctgtc ttccttttgg
15001 gcccctaccag catgacaggg ggctgcgggc aggaggggac agaggccacg ttgacacaca
```

TABLE 1-continued

Exemplary wild-type ErbB-2 nucleic acid sequence, GenBank Accession No. NG 007503.1 (SEQ ID NO: 1)

```
15061 gggctgtggg tgagagagac agctgaagtg tcagcgtgag gggccagtgt ggggctgcgg
15121 ctgggagggc tggggtgggg cccagggtag ttgtgcctgt ccttgggtga tggaatgatc
15181 tggaaagaga ttccttccct gccctccacc tgtgagaagc ccctctagag tgacatctcc
15241 atcttatgtt tggccaccca tcctccccct gggaagagag ccgaggtggg gtaagggatg
15301 tgtactcttt caaggagtgg gagaattatt ctagcgaatg tttgtgttgt cccagttctg
15361 ttttacaaagc ctcgtcatgt ttacagatgg ctgcgcaatt cattacctca tttaactctc
15421 atgtacctcc tctagggag taagagctgt tacagccaag tttaggtcag taaatattca
15481 ccaagttgca ggtactgcag ggcatagaga tgaatccgat ttagcttctg ccctggaggt
15541 ctgggaactt gctcaagatc actcagtgag cagctgagct agggttctca actaaagacc
15601 ctgggcccag gccctggtct gatgtcaggc ctgatacacc aggtgtttgt ggtcggggaa
15661 tcccagtgtc acttgaatgg gctgtgacat tatgggtctg ggagagctga gctttgggga
15721 cacaggtcat tttactgtag tattcatgga aaccaaggga agtattggct tttctgctgt
15781 gagcaagagg agcagctggg gctgcaagct ggtggggagg agaaaccca cctgagagaa
15841 acctcaggac tggggtcaag tcctgaccac cagagtccag agagacatga aggactgtga
15901 ccagctctga gcagagagat ggattccatg acctcaactg gtccctttg ttcggagact
15961 cgtgactgga cttcattcat ccactcattc attcattcac tcagcagaca cttatctagc
16021 gctccctgtg gctggtcctg cctcatactg tctttgctct ggagaattgg aggttggggt
16081 tcctgagggg cagggtcctg gagacaagga cactcctggg tagaattagg acctaccccc
16141 caggaaatca acggggacca ggtgccgtgg ctcacacctg taatcccagc actttgggag
16201 gccgagacgg gcggatcaca aggtcagcag ttcaggacca gcctggccaa catggtgaaa
16261 cccgcctcaa ctaaaaatac aaaaattagc caggtgtggt gtcaggcacc cgtaatccca
16321 gctactgagg aggctgaggc aggagaattg cttgaacccg ggaggcagag gttgcagtga
16381 gccgagattg cgccactgca ctccagcctg gcgacagggc gagactccat ctcaaaaaaa
16441 gaaaaccaat gggacagggc agatatgggg acaatggtaa ggagatggga gagtgggagg
16501 gaggtgtcag gaagaccttc ttgacttcat gtaggctggt gggggtgtta gccagcaagc
16561 ctccagttcc ctgggaaccg ttctcagggt accaatttta ccacctgtct gcaaacactt
16621 taagattctt aatcagactc aaattggcca caaatcaggt aaacaaactc actagtgggg
16681 tggggctacc acccgttctg accctccagc ccaacccagc ccagccaccc tgccctccgt
16741 agagcctgtg tgttttatcg gtggcattgg gagaattagt gtgtatttat gttggcgtgg
16801 ggtgtggggt ggatttgtgt gtgtgcagtt aggcctagtg gaaggaatgt gggatctgaa
16861 ggcaggccag cctgagttcc agtcctgcct gttgctcaca agctttatga ggcgagagct
16921 aaccccctgcc agcctcagtt gtcttctttg caagatggag gttgcagccc cagtctctgg
16981 agcatgttat gcagatccac cgagagtgcc tgccaggcac acagtaggtg ctcagctcag
17041 ttactgtggc ggcccccact ccccattgtt gttgttttcc tattgcctgg cggccacagc
17101 tggtatccct tgaaaagggc tacagggggt ggagtcggac cctgccccag ccctgtggag
17161 accctgggct tgggccaggg cctggggtct gggcctgcag acagctgtgt ctataaagca
17221 gctgaagggc tgaggccggg ggaggtcctg gcagcagggc gttattttgg gcctggcctg
17281 ccaccccag ctcctgtttc tcttgggagt ctgttggggg aggaagtgtg gggaagagga
17341 gggggtgcaa gtgggtgagg catggagtgg ggaggcctcc ctcagggaca tggaccttg
```

TABLE 1-continued

Exemplary wild-type ErbB-2 nucleic acid sequence, GenBank Accession No. NG 007503.1 (SEQ ID NO: 1)

```
17401 agttctattt ctgttcctcc ctcctgttcc tccctctttg tccttatctg cctagagagg
17461 tgggaataga ggccattctg agtatcacta ggagaccacc agtttgtggc cactggccac
17521 tggcccaggc agggaacctg ggggcttgcc ctaccagcct ctcccagcaa tctgaaggca
17581 gggggtacct cgtattaccc cctaggattt gaccttaggc tccaacttgc tgggagagca
17641 gtgcctctgg tgtcagaccc caagccagcc cttgtgctgt ccctgaatct gcatgtagcc
17701 tgtgggaggc ggagcagtga ccggcaggaa ttctgggcag ctcaggcacc tgtgggcctg
17761 agggtgccct ctgccccac ccttccgatc tcctgggcaa gacacgccag gtgattcatc
17821 tcaccagagc agaaaaacaa gttcaactgg gcactttaat ctcccctcac tggcaggcct
17881 ggtgtgagct gctaccccgg cgcccctcac caggggtgct ttacctcctc tagtattcct
17941 gaccttagtg ggcatttctg gtctcaggga taccaggctg gggtccaagt gggccaggtg
18001 tggcagttca gccctatgcc ccatggctga tggctcgcgc tgggcaggta tgcagggctg
18061 acgtagtgcc tttgtggcag cagtttcgtg gcacacattc tgccagctgg ttctggagtc
18121 ttgccctgag gaggtggcca gggtgagggt gccagcgcag gaacctttgg cgcatgcttc
18181 accctggcct gggatctgca gcctgggtcc agatgcccac aactggaatc tgacgctcct
18241 ttttctcttca tgggggactc ccagaggtct ctgcaatgac cagagcccg gttgtcccat
18301 gcctcagctg caactccagc tgaccctcct tccccactct ctgggtggca ttacgggggt
18361 gtggatccct tgccaagagg ttggcatgtg ggtgtgctgg aatggcatag ggagaatgca
18421 ccgagtttgt ttgcttggga gaggggcagg gggtatccag aagattcatg attcgtcatc
18481 gcctctcttg ggggattttt accccttgc cctgagttgt gcctttggga caaggaagc
18541 ctttctttgc cagccaacac cctgtactgg cgggcgagct ccccagggct ggcacgctgg
18601 ggcagcctct gaatgcacag ggtgggccta gtcagaagaa gccttcccc tgaaatccct
18661 ctacttccca agcacgcaag cttctcctg ctgttaaacc tgcagtgtgc aagggacatg
18721 ggcggagggg tccttcagtc aggcttctcc ctgtctgagg tggcatgact tggagtgagt
18781 ttggatgggg tggccaggtc tgagaaggtc ccccgccagt gtcctctgac ccatctgctc
18841 tctcctgcca gtgtgcaccg gcacagacat gaagctgcgg ctccctgcca gtcccgagac
18901 ccacctggac atgctccgcc acctctacca gggctgccag gtggtgcagg gaaacctgga
18961 actcacctac ctgcccacca atgccagcct gtccttcctg caggtgaggc ccgtgggcaa
19021 cccagccagg ccctgcctcc agctgggctg agccctctgt ttacaggtgg gtggcagaag
19081 aaggtgccct gcccttctgt ttcctctctt gttgtggttt ctcaaccagg aagtcctttc
19141 taacatctaa cccccattca ttttactgca gaatcagttg actctctcta taacgtggct
19201 ggccgaggtc atgtctggat gggatgcgtc tgtgttccg ctaaatcttg tgctctcttg
19261 ccagcatgat catgtcccct gtccacctgc tccagccact atccctctcc cacttacagc
19321 agaagaaagg gctggtgaga aaggtggatt acaggcccac ttctgccact gacgagccct
19381 atgaatgtgg cctacacccc cttagcttca ctgggtctca gtttccctat ctgtatattg
19441 ggagcagttg tgaagctcag aagagaaatg tctgtgaaaa ggttatgaac aggagggaga
19501 gtggaaacca acctgctgga tcgtgtccac agaccctgga atggggccac atgcttggtt
19561 tgtcaaattg cagacgccgg ccgggtgcga tggctcatgc ctgtaatccc agcactttgg
19621 gaggccgagc cggacagatc acttgaggtc gggagttcga ccagcctg accaacatgg
19681 agaaaccccg tctctactga aaatacaaaa ttagccaggc atggtggcac atgcctataa
```

TABLE 1-continued

Exemplary wild-type ErbB-2 nucleic acid sequence, GenBank Accession No. NG 007503.1 (SEQ ID NO: 1)

```
19741 tcccagctac ttgggaaggc tgaggcagga gaatcacttg aacctgggag acggaggttg
19801 tggtgagcct agatcgtgcc attgtactcc agcctgggca acaagagtga aactccgtct
19861 caaaaaaaaa aaatttgcag acgccatccc atccaggcct ttgctttcac tgatgaagaa
19921 actgagatac agagagggca gggcacctgt tcggagttta tgaaatgccc ccccaccatt
19981 atctttcttg atcatataag aatctggtga ggcaaggtag ggcgtgatct ttatctctat
20041 ttttatcgtt tatttaagcg ggaacaggac tgctcagtgg ctgggggcct tgcccaagat
20101 ctccaagtac tggggaaccc cagggaggcc ctgggggtg gcagtgttcc tatttcagcc
20161 ccactctgct tcccctccc aggatatcca ggaggtgcag ggctacgtgc tcatcgctca
20221 caaccaagtg aggcaggtcc cactgcagag gctgcggatt gtgcgaggca cccagctctt
20281 tgaggacaac tatgccctgg ccgtgctaga caatggagac ccgctgaaca ataccacccc
20341 tgtcacaggg gcctccccag gaggcctgcg ggagctgcag cttcgaagcc tcacaggtgg
20401 ccttcaccgt cattgaaacc ttctcttggt tattcagagc tgaccagggc cactgctaac
20461 caggggggagg ctttgtgtgc attagaaatg gtgtccattc tgggcagacg caggcagagc
20521 ccgggaagac gccctcagaa gattggaaaa agattcccct tcttcctggg aagttgtagc
20581 ttgcgtcagc acatataatt caatcgtgag aatgcaggct gggttttttgc ccccacttgg
20641 ctgagtgaag tgtacagtga acaacctatg taactatttg ctggccctgg agccgactct
20701 gccccagagt ctgggtgcca ggtgctttgc ccgcatggcc catttcagtc acgctgcagt
20761 cctgtcagga aaaaatcagt gttattctca ttctacatat gagaaaactg aggcttgcag
20821 atataagggc caaaagttac acagctagtg agtgatgggg ctgagtttca gactccacag
20881 tctcttaacc accaagcagc atgcccagag tagaggtgag aaggaaggag agagctgcgg
20941 tccacatgag catctggacc tagcatggac aactcactcc tccctggctc tcgctttgtt
21001 cttgttgcgg gtgtggtggt ggtgggactc aaagacggta aagatagctt tctctcctcc
21061 ctggggaatc tgggggttgt ttaaaaggcc tgctcctctt ttagaaggca ggagggcccc
21121 aagggaagca gaaggtgaca gaaggggaaa gggtcctctg atcattgctc accccacaga
21181 gatcttgaaa ggaggggtct tgatccagcg gaaccccag ctctgctacc aggacacgat
21241 tttgtggaag gacatcttcc acaagaacaa ccagctggct ctcacactga tagacaccaa
21301 ccgctctcgg gcctgtaagc catgcccctc cctgctgcct cttctctcag acagcctgac
21361 cccagccgca aactcccaac ttacaaccca gtgcctgccc gccactgccc cagccgccta
21421 caccacccat ttcctcccctc tctgtccctc ctgccatctc cctgtgcctc ttcatctctg
21481 gggttctctg tcttgtctcc ctctgcttat aggttgtgcc tctggtttgg gggcctctca
21541 gcctgtctgg gtccctccct tgctgtgcag ttggcctcgt ggcctctgct gctgtttgtg
21601 cctctctctg ttactaaccc gtcctctcgc tgttagacat ctctctcact gcctgtctct
21661 ggttctgtcc tcaggccacc cctgttctcc gatgtgtaag ggctcccgct gctggggaga
21721 gagttctgag gattgtcaga gccgtgagtc tcagggaggc ctggagtcag ggaaggggag
21781 ggctggggcc gggtggaatg caggtgtcat acaggtgaca tgggagggggt gggataacag
21841 gcttgggatg tctccccctgg gccaggtagt ctccctagaa ggtgatgctg atgagggtct
21901 ggtgcccagg gcgccactca gccctcatcc tgccctttgc ccaacagtga cgcgcactgt
21961 ctgtgccggt ggctgtgccc gctgcaaggg gccactgccc actgactgct gccatgagca
22021 gtgtgctgcc ggctgcacgg gccccaagca ctctgactgc ctggtatgtg cctctgcttt
```

TABLE 1-continued

Exemplary wild-type ErbB-2 nucleic acid sequence, GenBank Accession No. NG 007503.1 (SEQ ID NO: 1)

```
22081 gtgcccaatg tgctctaccc cccaggatgc aaggggtggg caccctgcct ggtactgccc
22141 tattgcccct ggcacaccag ggcaaaacag cacagtgaaa gccagccacc tgtcccccca
22201 ggcctgcctc cacttcaacc acagtggcat ctgtgagctg cactgcccag ccctggtcac
22261 ctacaacaca gacacgtttg agtccatgcc caatcccgag ggccggtata cattcggcgc
22321 cagctgtgtg actgcctgtc cctgtgagtg ccagggagaa acacagtttt ctcattttgg
22381 tgggaggtt tgtttctgta aatgggagca tatggggagc actgtctgca tcttgctttg
22441 agagctggtc atgacagttc ctgccgagct gccttgttct ttcaacagct gtggagcagg
22501 tggcagtaag gagaggcagc taagagccca gacttgggag ccagactgcc tgggtttgaa
22561 acccagctct atcaattagt aggcacgtga ccctcttgct gtgcctcagt ttcctcatca
22621 gtaaaatggg ggcaagaata gtcccaactg cataagatgg ttataacatt tgaaagagtt
22681 aatatttgta aagctcttag aacggtgcct ggtatgtact aagtgctcct aaatgttagc
22741 ttttattcta tagcctggtg aggtcagttt tacctttcgt tttgttttt agaccgaatt
22801 tagttagctc tatcgcagtg gcgcgatctc ggctcactgc aacctccgcc tcccaggttc
22861 gtgctattct cgtgtctcag cctcctgagt agctgggatt acaggcgccc accaccatgc
22921 ctcgctaaat tttgtatttt tagtagagac agggtttcac cacgttggcc agactggtct
22981 cgaactcctg acttcaggcg atccacctgc ctaggcctct gaaagtgctg ggattacagg
23041 cgtgagccac tgcaccccgga cttttttttt tttggcagag tctcgctcca ttgcccaggc
23101 tggagtgcag tggtgcaatt ttggctcact gcaacctctg ccttccgcat tcaagcaatt
23161 cttgtgcctc agactcttga gtaggtggaa ctacaggcat gcaccaccat ggctgggtaa
23221 ttttttgtatt tttagtagag acggagtttc actatgttgg ccaagctggt ctcgaactcc
23281 tgacctcaag tgatccaccc gccttgttct cccaaagtgc tgggattaca ggcatgagcc
23341 atcgtgcctg gcctagctca gttttattta acagatcacc tatttactga tgggcgttta
23401 tggactgggc tcagacctgg ggaacctctt tcctcctctc acaggaacag gagtgggcct
23461 tcagatcctg gctgactgtg ttagggagag acaaaatgt agagccagac catttgggtt
23521 caaatcctcg ctcctccact cactagcaca atgaccttga ataatttaca gaactctctg
23581 ctttggtctc cctttttgca aaatgggaat ctcacagtgc tgatcccgtc tggttgttgt
23641 gaggggtaaa tggatgtcag gtgctgatgc gtggtagggc atttaagtat tggttgatat
23701 tattcttctt gtgcctgggc acggtaatgc tgctcatggt ggtgcacgaa gggccagggt
23761 atgtggctac atgttcctga tctccttaga caactacctt tctacggacg tgggatcctg
23821 caccatcgtc tgccccctgc acaaccaaga ggtgacagca gaggatggaa cacagcggtg
23881 tgagaagtgc agcaagccct gtgcccgagg tacccactca ctgaccccga ggccagctgc
23941 agttcctgtc cctctgcgca tgcagcctgg cccagcccac cctgtcctat ccttcctcag
24001 accctcttgg gacctagtct ctgccttcta ctctctaccc ctggccccc tcagccctac
24061 aagtgtccct atatcccctg tcagtgtggg aggggcccg accctgatg ctcatgtggc
24121 tgttgacctg tcccggtatg aaggctgaga cggccccttc cccacccacc cccacctcct
24181 cagtgtgcta tggtctgggc atggagcact tgcgagaggt gagggcagtt accagtgcca
24241 atatccagga gtttgctggc tgcaagaaga tctttgggag cctggcattt ctgccggaga
24301 gctttgatgg gtaagagtgg gcacgatgac ctgagacagt gtcagggcag acagagtcct
24361 gaggatccag atgtggcagc atctcttggg gatggcagga gacagaagtg gggggatcaa
```

TABLE 1-continued

Exemplary wild-type ErbB-2 nucleic acid sequence, GenBank Accession No. NG 007503.1 (SEQ ID NO: 1)

```
24421 gaatgcaaag aaagcagatg ggagaccaga ggagcagggc ctttggtggg tgggggtgat
24481 tatttttgta aatgacatgc tatccgtgaa caaggacttg tatggaggtc agaccatcta
24541 gataaagtaa aattcccttt gagttcatag cagctttatt caaaatatcc ccaaattgga
24601 aataactcaa atgtgcatca ctaggtgaag gaataaacaa gtggcagtgt atccatttgg
24661 tgaagttcta cttagcaacc aaaggaaatg aactaccgat acaacataaa tgaatctcag
24721 aaacattaca ttgagcaaaa gaagccagag acaagattcc atactgtctg atcccctta
24781 tgtgaggctc tgaaccgaaa aaaccactct gtggtgggag agatcagaac ggtggttgcc
24841 ccagggtggg gggcttcaaa agggaggcac acaaggacat ttctggggta atagaaatgc
24901 tctgtatagt gattgggta gtggatacat gagcgaatcc atttgtcaaa actcatcaaa
24961 ctgtgtgata agagtctgtg cattttattt atttcatttt attttttgag atagagtctc
25021 actctgtcag caggctggag tgcagtggta cgatcttggc tcactgcaac ctctgcctcc
25081 tggattcaag caattctcct gcctcagtct cctgagtagc tgggactaca ggtgtgtgcc
25141 accatgccca gctaattttt gtattttaa tagagatggg gtttcaccat gttggcaagg
25201 atggtctcga tctcttgacg tcgtgatccg cccacctcag cctcccaaag tgctgggatt
25261 acaggcatga gccaccacac ccggtgcatt ttattgtata taagttatac ttcaataaga
25321 aatgaattgg ggccaggcac ggtggctcac gcctgtaatc ccagcacttt gggaggccga
25381 ggcaggcaga tcacttgagg tcaggagttc aagaccagcc tggccaacat ggtgaaaccc
25441 catctctact aaaaaatata aaaaattagc caggcttcct ggcatgcgcc tatcatccca
25501 gctacttggg aggctgaggc aggagaattg catgaactcg ggaggtggag gttgtagtga
25561 gctgagattt cgctattgca ctccagcctg ggcgacagag tgagaccctg tctcaaaaag
25621 aaaaaaaaaa aaagggtca ggcgccgtgg tgcacacctg taatcccagc actttgggag
25681 gctgaagcag gaagattgct tgagcccagg aattcaagaa cagcgtgggc aacatagtga
25741 gatcccatct ctacaaaaaa acacaaaaaa ttagccgggc atggtggtac gcacctgtag
25801 tctcagctac tagggagact gaggtgggag aatcacctga gcctgggagg tggaggttgc
25861 agtgggttga aatcatgtca ctgtactcca gcctgggtga cagaatgaga ccctgtctca
25921 aaaaaaaaaa aaaaaaaaaa attccctttc acacttcctt tacctccact cccctttcca
25981 gagggggcca tggttaacag tgtgtgtgtt cacctagacc gtttatgcat ctgtagacac
26041 acacacagtg aagtgtggtt ttcgtcgttt tggtggggag gttggtttct gtaaatggga
26101 acatataggg agcactgtct gcaccttgct ttgagagccg gtcatgacag ttcccattga
26161 actgccttgt tctttcaata gctgcagagc aggtggcggc aaggagaggc agctaagagc
26221 ccagacttgg gagccagact gcctgggttt gaaacccggc tctaccactt actaggcatg
26281 tgacccttgt gctgtgcctc agtttcttca tctgtaaagt gggggcaaga acagtcccaa
26341 cttcataaga tggttatacc accatgcctg gccagatgat tataaagttt gaatgagtta
26401 atatttgtaa agctcttaga acagtgcctg gcagatacta ggtgctccta aatgttggtt
26461 ttttattatgt ggctgggtgg ctcggggttt tatttaacag ctccccctatt tactaataga
26521 catttagatc atgttccatt ttcactctta caaacagttc cactttgtgt gtggctctgg
26581 gaacatgggc cagtgtctcc ctaggccaca ttcctagaaa taagatttct tttcttttt
26641 ttttttttt gagacagagt ctcgctttat cgccaggctg gtgtgcagta gtgtgatctc
26701 ggctcactgc aacctctgcc tcccgggttc aagtgattct cctgcctcag cctctcgagt
```

TABLE 1-continued

Exemplary wild-type ErbB-2 nucleic acid sequence, GenBank Accession No. NG 007503.1 (SEQ ID NO: 1)

```
26761 aactgggact ataggcgcgc ggcaccacac ccagctaatt tttgtatttg tagtagagat
26821 ggggttttcac catgttggcc aggatggtct ccatctcttg acttcgtgat ccgcccgcct
26881 cggcctccca aagtgctggg attacaggcg tgagccactg agcccaggca gaaataagat
26941 ttctagatca aaggatataa atactgtttt gatagatgtt gccgaactaa ggcctgggct
27001 ttgaagccca ggatgggaac agctgggctc gatgggcaaa gggtttgagt gaaggcattc
27061 atggtgggga gtggctggca tggccagtgc tgggagtgat gtccaccctg ttcctggccc
27121 tgctgactcc tctcctgacc cctccaggga cccagcctcc aacactgccc cgctccagcc
27181 agagcagctc caagtgtttg agactctgga agagatcaca ggtgggctct gtctctgcat
27241 cctgttctgc aggggctggg agtccttgtc ctgtccccac tcctttaatc tcaccctctg
27301 cctgcaggtt acctatacat ctcagcatgg ccggacagcc tgcctgacct cagcgtcttc
27361 cagaacctgc aagtaatccg gggacgaatt ctgcacaagt gagcactgag aaagagggg
27421 cctgatgggg aggagtccca gggaggagtc cctgtgggaa gctttgggcc tgagggagta
27481 ctcctgtagc agtaaccttt ccatgaaagt ctgcagagtg tgctggggat ggaggaagat
27541 gagaatagcc tttgctgacc gggaaggggt ccgtggtaag gtgcccacct ttctcccata
27601 gtggcgccta ctcgctgacc ctgcaagggc tgggcatcag ctggctgggg ctgcgctcac
27661 tgagggaact gggcagtgga ctggccctca tccaccataa cacccacctc tgcttcgtgc
27721 acacggtgcc ctgggaccag ctctttcgga acccgcacca agctctgctc cacactgcca
27781 accggccaga ggacgagtgt ggtaagacag ggagcccagt gtgcgcactc cccatctgcc
27841 agcacacagc agtgcccagg gggccctggc agcagcgttc ttggacttgt gcagactgcc
27901 cgtctctgtg caccctccttt gactcagcac agctctggct ggcttggcct cttggcatgg
27961 cttctctagc tgggtcctac ctgccttggc atccttccct cccctctgt ttctgaaatc
28021 tcagaactct tcctctccct acatcggccc cacctgtccc caccctccc gcccacagcc
28081 atgcccacag ccagttccct ggttcacttg gacctggggc ctcccctaaa agtcccctgc
28141 ggtcccttcc tcctcactgc agtgggcgag ggcctgggct gccaccagct gtgcgcccga
28201 gggcactgct ggggtccagg gcccacccag tgtgtcaact gcagccagtt ccttcgggc
28261 caggagtgcg tggaggaatg ccgagtactg caggggtatg aggggcggag gagagggtgg
28321 ctggagggt gcatgggct cctctcagac cccctcacca ctgtcccttc tctcaggctc
28381 cccagggagt atgtgaatgc caggcactgt ttgccgtgcc accctgagtg tcagccccag
28441 aatggctcag tgacctgttt tggaccggtg agctgctggc gggctcagag ctgggtggag
28501 gggggcagcg aggggattg ccagggactt ggcaggatgg cgagatgcag tagggtgtgc
28561 tatctggtaa aatatccctg gagagggctc agcgctcaga cctgaacagc aacagagtgg
28621 cagaaaaggg gcctggggga cactgggcc cttcagacta tgaaaaggtt ctaaggaggt
28681 ctgtgttggt ggctgtgact gtggctgtgc tagggtggtg agccctgtgg gctcaggcgt
28741 cagactacct ggattcagac ccagctcctg cttccaacct tggtttttta ttcctaaaat
28801 gggtattgta ataatacta ccttgctggg gtgtggcaag aatgaaatta aacagggctt
28861 ggcacagtga agcacgggaa aggctttcta cagagcagtg actgttgtta ctcgctgtta
28921 caccttaggt aatgcgtttt cctctctggg tgcctcccat tttctggctc aagtacctgc
28981 ccaggatcaa gcttggagga gggccccgag ggagggggcca cagagactgg gtgaagagca
29041 agggtgtttg tcccaggagc atggcgaaaa ttgctgctgg gtggccttgg gaagcacaaa
```

TABLE 1-continued

Exemplary wild-type ErbB-2 nucleic acid sequence, GenBank Accession No. NG 007503.1 (SEQ ID NO: 1)

```
29101 ggggacccaa ctaagggcct gatcctactg ccctgggggt gtcagtgcca gcccccaca
29161 aatcttttct gccccccca ggaggctgac cagtgtgtgg cctgtgccca ctataaggac
29221 cctcccttct gcgtggcccg ctgccccagc ggtgtgaaac ctgacctctc ctacatgccc
29281 atctggaagt ttccagatga ggagggcgca tgccagcctt gccccatcaa ctgcacccac
29341 tcgtgagtcc aacggtcttt tctgcagaaa ggaggacttt cctttcaggg gtctttctgg
29401 ggctcttact ataaaagggg accaactctc cctttgtcat atcttgtttc tgatgacaaa
29461 aataacacat tgttaaaatt gtaaaattaa aacatgaaat ataaattaat gccctagcag
29521 ttctatcccc actgttaata atttgaaata tttttcctct agttattttt gtctgtgcac
29581 attctaatat gtatatataa gttaacatat attaatatta ttctccagtt attttatct
29641 gtgcacattt taacacacac acacacacac acacacacac acatatgtat ttttagacgg
29701 agtttcactc tgtcgcccag gctggagtgc agtagtacaa tcttggctca ctgcagcctc
29761 cacctcctgg gtttaagcaa ttctcctgct tccgcctcct gagtagctgg gattacggga
29821 acgtgctacc ttgcctggct aatttttgta tttttagtac ataggatttc accatgttgg
29881 ccaggctggt ctcgaacccc tgacctcagg tgatctgcca gcctcggtcc cccaaagtgt
29941 tgggattaca gcgtgagcc accatgccca gtcatatatt tctttttaac aaatagaatc
30001 atagatcata catattgttt gcaaattgct ttttctcact ttccagaacc ttgaaatgtt
30061 ttttccatgt tctaacatgg tgatctacct tattctttaa ttttttcttat ttagttgtct
30121 ttacacatga aacacatgaa tacatccttg tgataaacat tttcagtaac ataaagtat
30181 aaatgttaca aagccaacgt gccctttcac tcaactccct gtccacccag tctctcctgt
30241 ctgctgggag aaccaccgca ttgacttgtg tgttcaccct tccaggctct tttctgcaca
30301 cttatataga catactacat ttatattagg tcgagtcaaa taagattgct gtttgtgtaa
30361 accaaaaagt gtcaagagcc tgggcgcagt gactcacacc tgtaatccca gcactttggg
30421 aggctgaggc aggcagatca cttgagatca ggagttcgag accaatctgg ccaacatagc
30481 gagacccgt ctctactaaa aatacaaaaa ctagccaggt gtggtgatgc tgttctgcac
30541 tttgctttcc ccccgacttg aggtatcctt tcttgtgagt acagacggat ctaccacctt
30601 tattttttt ttaattactc aacctgtaac atggatgtaa tttcacttg ttttgaggg
30661 atattgagct tgtttccctg tttttgcagt ttattgcaat tgagctccac acacaagtga
30721 gccctctttt gtatgccccc tagtgggaat acagtgctgg caatgtttat cacaaggata
30781 tattcatgca tttcaattta aagacaacta aatgagaaaa attaaaagaa tatggatcca
30841 ggctgggcat ggtggctcac gcctgtaatc ccagcacttt gggaggccga ggcaggcaga
30901 tcacctgagg tcaggagttc aagaccagcc tggccaacat ggcaaaaccc cgtctctact
30961 aaaaatacaa aaattagcca ggcgtggtgg tgggcgcctg taatcccagc tatttgagag
31021 gttgagacag gagaattgct tgaacctggg cagcggaggt tgcagtgaga cgagattgca
31081 ccagtgcact ccaacctggg caacacagtg caactccttc tcaagaaaaa aagaaaaaa
31141 aaaaagaata tgggtccaga tccatatgga tcctagatcc agatcacggt gttagaacat
31201 ggaaaaacat tgcaagattc tgctaagtga aaaaagcatt tgcaaacagt atgtacagtc
31261 tatattcaga ggaggaactg ctgggtcata gatgatattt cataggtatt gccaaaccgt
31321 tctctggaga agtggtatgg gtttaccctg ggattcttct atggagggaa tagttgagct
31381 cccgggcttg ctcttctggg tgcccctccc cgcttcctat ccaccacaag gagctgcagg
```

TABLE 1-continued

Exemplary wild-type ErbB-2 nucleic acid sequence, GenBank Accession No. NG 007503.1 (SEQ ID NO: 1)

```
31441 ggagcggggc atgccggttc cttggctgga gaaggagtct ccttgtgagg tggtagaagg
31501 agcactgacg gccttgagcc cagtttctgc ctttgtcaaa tggggataat gacccagcca
31561 caccectccc agggttgttg tgaggctgga aaggtggttc ccaagagggt ggttcccaga
31621 attgttgatg agactgtttc tcctgcagct gtgtggacct ggatgacaag ggctgccccg
31681 ccgagcagag agccaggttg gcctggaccc caggatgtac ccttcattgc ccttcactcc
31741 cccactggat gctgggtggt cactgctgta ggggaggggac cccctgacat atgtcccttc
31801 ccacccactc ttccactgtg gaacctcctg tcattttcca cttcaccaag tgacagagga
31861 cctgctcaga tgctgagggg aggggactgc aaggaaagat ggctaggaaa cccagtccct
31921 ccacacccta gagtaacttg atgccttgtg agggacacag gcaaagttca attccttgga
31981 agtcaaggga gactgagaag agtacagctg cagcactgag ggagtgatga attcttaact
32041 ggggatggtg ggaggcttcg agtgggaggt ggcatttgag ctaggctttg agagaggagc
32101 aggtattgca cttgcattta ggtagaaagc attggggtgc aaggtgacac tggagggga
32161 ggcatcagga aatccaggat gtcttcaaag ttctggtgtc gggggctgtt gagtaagcac
32221 aggaataagg gggtcaagtt agagtcaggg tggggtctga cctggatgcc ataggacctg
32281 atccccaagc cacagggtgg gacttgactg ggcagtgggg acctttggaa aggactttgg
32341 ggagaaaaac agactggagt ctgtcttagg cgatcatcgg tccgtgaaat gagcatgtgt
32401 tacaggcttg gtatgtacca gaccctgtgc taagcaaggg ggtatggaga ggagagggtg
32461 acaagaatat tggatcaaca cccgggagct ccatctatcc caggatgcac tatctttttt
32521 ttatttttt gagacggagt ctcactctgc ctgcaggctg gagtgcagtg gctccatctc
32581 ggttcactgc aacctctgcc tcctgggttc aagcgcttct tgtgcctcag cctcccaagt
32641 agctgggatt acaggcacat gccaccacac ccagctaatt tttgtatttt tagtagagac
32701 ggggtttcac catgttggcc aggatggtct cgatctcttg acctcaagat ccgcccacct
32761 tggcctccca aagtgctggg attacagaca tgagccaccg tgcccagcca gatacgctat
32821 cttttttattg agtgattgag acagggtctt gctctcttgt ccagtcttga atgtggtggt
32881 gtaatcacag gctcactgca gccttgacct cctgggctca agttacccett ctgcagtagc
32941 tgggactata ggagcgtgcc accacgcctg gtaatttaa aaaatttttt ttgtatagac
33001 agggtctcac tatgttgccc gagctggtct caaactcgtg ggctcaagtg atcctccagt
33061 tttggcctcc caaaatgttg ggatcacagg agtgagccac cactcctggc gatgagccaa
33121 gtctttttt tttttttttt ttttttgatat ggagtcttgc tctgttgccc aggctggagt
33181 gcaatgacac gatcttggct cactgcaacc tctgcctccc aggttcaagc agttcaagca
33241 atcctcctgt ctcagccccc cagtagctgg gattacaggc atgcgctacc acgtccggct
33301 aattttttgta tttttagtag agatgaggtt ttgccatgtt ggccaggctg gtcttgaact
33361 gctgacctca ggtgatccac ctgcctcggc ctcccaaagt gctgggatta caggtgtgag
33421 ccatcgtgcc tggcggagcc gagtcttaaa agatgaccct gtggagaaat ggtggtccag
33481 gctgaaggga cagcctatgc aaacactggg aggtgtggaa aatcatgacc tgtgggtgga
33541 aattttggct agaacatcaa aatcatcagg tgtacattcc tgtacccatg cagcagtcag
33601 aatctctggg ggtggggccc caaaattgta tgcatacaga ctgtgtgctg atttgtgata
33661 ttacttagga tttttgact ttacaatggt ggaaaagcaa taatatacat tcagtataaa
33721 ccgtactttg aatacccata cagccattct gttttcact tttattttta tttatttatt
```

TABLE 1-continued

Exemplary wild-type ErbB-2 nucleic acid sequence, GenBank Accession No. NG 007503.1 (SEQ ID NO: 1)

```
33781 tatttattat ttattttgag atgtcatttt gctgttgtta cccaggctgg agtgcaatgg
33841 cgcagtcttg gctcaccgca acctccacct ctcaggttca aacgattctc ctgcttcagc
33901 ctccagagtg gctgggatta caggcaggca ccaccacacc cggctaattt tgtattttta
33961 gtagagacgg ggtttctcca tgttagtcag gctggtctcg aactcgagag ctcaggtgat
34021 ctgcccatct cagcctcaag ccaccatgcc cagccctact ttcagtattc aataaattac
34081 atagccaggc accgtggctc acacctgtaa tcccagcact ttaggaggcc aaggtgggag
34141 gatcctttga ggccagaagc tcgagaccag cctgggcaac atagtgagac cccatttcta
34201 caaaaaataa aaaaactagc tgagtgtggt ggcgtgtgtc tgtagtccca gctacttggg
34261 cagctgaggt ggaaagactg cttgagccca gaggtcaggg ctgcagtggg ccatgatctc
34321 accactgcac tcagcctggg caacacagca aggccctgtc tcaaaaataa ataaataaat
34381 aacacaaact tatttaacag tttactataa aataggcttt gtgtcagatg attctgccca
34441 actgtaagct gctggcagtg taaatgttct gagcacgtgt aagccaggct aggtgtctta
34501 aatgcatttt cagtttcaac ttagaattgg tttatcagga cgtagcccct tggtgttgag
34561 gggcatgtgt attaacagtc tccttagtga cttttttttt tttgagatgg agtcttgcac
34621 tggccgtagt gcagtggcac aatctcagct cactgcaacc tcttgtctcc cgggttcaag
34681 cgattctcct gcctcagtct cccaagtagc tgggattaca ggcacccaca ccacgcccag
34741 ctaattttg tgtgtgtgta ttttagtag agacggggg ttcactatgt tggccaggct
34801 ggtctcgaac tcctgacctt gtgatctgcc cacctcagac tctcaaagtg ctaggattcc
34861 aggcatgagc caccgcgccc agagtcctta gtgatttta caccatgaat tgttgaagcc
34921 ctaagccaga gccaagggca agagtataga gaatctggag atgcggagag ggttctgatt
34981 gcctacaagg agtttggact ttattgtgga ggcagcgggg agccaaggca ggtttagag
35041 taggagaggg tccaagcctg tgggtcaccc ttccgacttc cctttccgaa tgccaaacac
35101 cttcatgtcc cccgtgggcc ccctttgtcc ctcccacccc aaactagccc tcaatccctg
35161 accctggctt ccgcccccag ccctctgacg tccatcatct ctgcggtggt tggcattctg
35221 ctggtcgtgg tcttgggggt ggtctttggg atcctcatca agcgacggca gcagaagatc
35281 cggaagtaca cgatgcggag actgctgcag gaaacggagg tgaggcgggg tgaagtcctc
35341 ccagcccgcg tggggtctgc accggccccc ggcactgacc caccacccc tcacccagc
35401 tggtggagcc gctgacacct agcggagcga tgcccaacca ggcgcagatg cggatcctga
35461 aagagacgga gctgaggaag gtgaaggtgc ttggatctgg cgcttttggc acagtctaca
35521 aggtcagggc caggtcctgg ggtgggcggc cccagaggat ggggcggtg cctggagggg
35581 tgtggtcggc agttctgatg ggaggggcaa gagctggagg cagtgtttgg gggagggcag
35641 ttacagcgga gaagggagcg gggccaagcc ctagggtggt gaaggatgtt tggaggacaa
35701 gtaatgatct cctggaaggc aggtaggatc cagcccacgc tcttctcact catatcctcc
35761 tctttctgcc cagggcatct ggatccctga tggggagaat gtgaaaattc cagtggccat
35821 caaagtgttg agggaaaaca catccccaa agccaacaaa gaaatcttag acgtaagccc
35881 ctccaccctc tcctgctagg aggacaggaa ggacccatg gctgcaggtc tgggctctgg
35941 tctctcttca ttgggttg gggagatatg actcccgcaa acctagacta ttttttga
36001 gacggagtct tgctctgtca cccaggctgg agtgcagtgg cgttatctcg gctcactgca
36061 acctccacct cctggactca agcgattttc atgcctcagg ctcctgagta gctgggatta
```

TABLE 1-continued

Exemplary wild-type ErbB-2 nucleic acid sequence, GenBank Accession No. NG 007503.1 (SEQ ID NO: 1)

```
36121 caagcgcccg ctaattttt tttttttttt gagacagagt ctcgctctgt cacccaggct
36181 agagtgaaat ggtgcggtct cagctcagcc tcccaggtta aagcgattct tctccctcag
36241 tctcctgagt agctgggatt acaggcgcga gccaccacgc ccggctaatt tttgtatttt
36301 tagtagagat gggatttcac catgttggcc aggttggtgt caaactcctg acctcatgat
36361 ccgcccgcct cggcctccca aagtgctggg attacaggtg tgagccaccg tgcccggcct
36421 aatctttgta tttttagtag agacagggtt tcaccatgtt gtccaggctg gtactttgag
36481 ccttcacagg ctgtgggcca tggctgtggt ttgtgatggt tgggaggctg tgtggtgttt
36541 gggggtgtgt ggtctcccat accctctcag cgtaccttg tccccaggaa gcatacgtga
36601 tggctggtgt gggctcccca tatgtctccc gccttctggg catctgcctg acatccacgg
36661 tgcagctggt gacacagctt atgccctatg gctgcctctt agaccatgtc cgggaaaacc
36721 gcggacgcct gggctcccag gacctgctga actggtgtat gcagattgcc aaggtatgca
36781 cctgggctct ttgcaggtct ctccggagca aaccctatg tccacaaggg gctaggatgg
36841 ggactcttgc tgggcatgtg gccaggccca ggccctccca aaggtctac atgggtgctt
36901 cccattccag gggatgagct acctggagga tgtgcggctc gtacacaggg acttggccgc
36961 tcggaacgtg ctggtcaaga gtcccaacca tgtcaaaatt acagacttcg ggctggctcg
37021 gctgctggac attgacgaga cagagtacca tgcagatggg ggcaaggtta ggtgaaggac
37081 caaggagcag aggaggctgg gtggagtggt gtctagccca tgggagaact ctgagtggcc
37141 acctcaccac aacacacagt tggaggactt cctcttctgc cctcccaggt gcccatcaag
37201 tggatggcgc tggagtccat tctccgccgg cggttcaccc accagagtga tgtgtggagt
37261 tatggtgtgt gatgggggt gttgggaggg gtgggtgagg agccatggct ggagggagga
37321 tgagagctgg gatggggaga attacggggc caccctcagca tgtgaaggga gggaaggggc
37381 tgcctgtgcc ccaccttgca gggtctgtgc acttcccagg attagggaaa gaccgggtag
37441 ggtctgtctc ctggcatcac atctccccct gctacctgcc atgatgctag actcctgagc
37501 agaacctctg ctcagtaca ctaaagctcc ctctggccct cccactcctg accctgtctc
37561 tgccttaggt gtgactgtgt gggagctgat gacttttggg gccaaacctt acgatgggat
37621 cccagcccgg gagatccctg acctgctgga aaaggggggag cggctgcccc agccccccat
37681 ctgcaccatt gatgtctaca tgatcatggt caaatgtgcg tggctgagct gtgctggctg
37741 cctggaggag ggtgggaggt cctgggtgga ggagcccaca aggggcatga aaggggacca
37801 ggatgtatgt agacccagga gccctagtat gttaggagcc tcaaaacctt cttgtatccc
37861 ttttacagtc aaagtccaaa gccactcttg aggaacactc ttgtacaaaa ttaagctggg
37921 cacagtggct catgcctgta atcccagtac ttttggaggc tgaggtggga ggatcccttg
37981 aagccaggag ttcaagacca gcctgggcaa catagtgaga tcctatctct acaaaaaata
38041 aaaaaattat ctgggtgtgg tggtgtgtgc cagtagtccc agctactcag gagaggctga
38101 ggcaggaaga tcacttgagc ctagtttaag gttgcagtaa gctatgattg caccactgaa
38161 atccagcctg ggtgacagag cgaaacctca tctcaaaaaa ataaaaaagc aaacaaaaag
38221 aaaaaaaaaa ttaaaaggga aactagaaga gatgccaaag gttctggctg aagaccccag
38281 agtctggtgc tacttctcta ccacctgagg ctttgggct gtcccttggg actgtctaga
38341 ccagactgga gggggagtgg gaggggagag gcagcaagca cacagggcct gggactagca
```

TABLE 1-continued

Exemplary wild-type ErbB-2 nucleic acid sequence, GenBank Accession No. NG 007503.1 (SEQ ID NO: 1)

```
38401 tgctgacctc cctcctgccc caggttggat gattgactct gaatgtcggc caagattccg
38461 ggagttggtg tctgaattct cccgcatggc cagggacccc cagcgctttg tggtcatcca
38521 ggtactgggc ctctgtgccc catccctgcc tgtggctaag agcaccctcc tgcagagggt
38581 gggaaggaga gatgagtcca gtatgccagg cccctcacgg aaggctgcat gctgggctgg
38641 ggaggggcca ccatcctgcc tctccttcct ccacagaatg aggacttggg cccagccagt
38701 cccttggaca gcaccttcta ccgctcactg ctggaggacg atgacatggg ggacctggtg
38761 gatgctgagg agtatctggt accccagcag ggcttcttct gtccagaccc tgccccgggc
38821 gctgggggca tggtccacca caggcaccgc agctcatcta ccagggtcag tgccctcggt
38881 cacactgtgt ggctgtctgc ttacctcccc caaccccggt ggactagggt ccatttctct
38941 gatgttccct caactgtcac ctctcaagga aaccccatta tccctacaaa aaattcttac
39001 tgccttccaa cccctgtgac cccattctct ccacggtgac tgtgtcatac cccaaaggtg
39061 acctctgttt ttctcctgtg accctgtcac cttccatgga gtccccatcc cagatccgtg
39121 agtgaccccc atcatgactt tctttcttgt cccagagtg cggtggga cctgacacta
39181 gggctggagc cctctgaaga ggaggccccc aggtctccac tggcaccctc cgaaggggct
39241 ggctccgatg tatttgatgg tgacctggga atgggggcag ccaaggggct gcaaagcctc
39301 cccacacatg accccagccc tctacagcgg tacagtgagg accccacagt accccctgccc
39361 tctgagactg atggctacgt tgccccctg acctgcagcc cccagcctgg tatggagtcc
39421 agtctaagca gagagactga tgggcagggg aggtgggacc ttcagcccag ggtccactgt
39481 gggggcagag ggagtggcag agacaccggg gttccttccc ctaatgggtc accttctctt
39541 gacctttcag aatatgtgaa ccagccagat gttcggcccc agcccccttc gccccgagag
39601 ggccctctgc ctgctgcccg acctgctggt gccactctgg aaaggcccaa gactctctcc
39661 ccagggaaga atggggtcgt caaagacgtt tttgcctttg ggggtgccgt ggagaacccc
39721 gagtacttga cacccagggg aggagctgcc cctcagcccc accctcctcc tgccttcagc
39781 ccagccttcg acaacctcta ttactgggac caggacccac cagagcgggg ggctccaccc
39841 agcaccttca aagggacacc tacggcagag aacccagagt acctgggtct ggacgtgcca
39901 gtgtgaacca gaaggccaag tccgcagaag ccctgatgtg tcctcaggga cagggaagg
39961 cctgacttct gctggcatca gaggtggga gggccctccg accacttcca ggggaacctg
40021 ccatgccagg aacctgtcct aaggaacctt ccttcctgct tgagttccca gatggctgga
40081 aggggtccag cctcgttgga agaggaacag cactggggag tctttgtgga ttctgaggcc
40141 ctgcccaatg agactctagg gtccagtgga tgccacagcc cagcttggcc ctttccttcc
40201 agatcctgga tactgaaagc cttagggaag ctggcctgag aggggaagcg gccctaaggg
40261 agtgtctaag aacaaaagcg acccattcag agactgtccc tgaaacctag tactgccccc
40321 catgaggaag gaacagcaat ggtgtcagta tccaggcttt gtacagagtg cttttctgtt
40381 tagtttttac tttttttgtt ttgttttttt aaagatgaaa taaagaccca gggggagaat
40441 gggtgttgta tggggaggca agtgtggggg gtccttctcc acacccactt tgtccatttg
40501 caaatatatt ttggaaaaca gct
```

An exemplary wild-type ErbB-2 protein sequence is NCBI Protein Accession No. P04626.1 (SEQ ID NO:2) (Table 2).

TABLE 2

Exemplary wild-type ErbB-2 protein sequence NCBI Protein Accession No. P04626.1 (SEQ ID NO: 2)

```
   1 melaalcrwg lllallppga astqvctgtd mklrlpaspe thldmlrhly qgcqvvqgnl 61 eltylptnas lsflqdiqev qgyvliahnq vrqvplqrlr ivrgtqlfed nyalavldng 121 dplnnttpvt gaspgglrel qlrslteilk ggvliqrnpq lcyqdtilwk difhknnqla 181 ltlidtnrsr achpcspmck gsrcwgesse dcqsltrtvc aggcarckgp lptdccheqc 241 aagctgpkhs dclaclhfnh sgicelhcpa lvtyntdtfe smpnpegryt fgascvtacp 301 ynylstdvgs ctlvcplhnq evtaedgtqr cekcskpcar vcyglgmehl revravtsan 361 iqefagckki fgslaflpes fdgdpasnta plqpeqlqvf etleeitgyl yisawpdslp 421 dlsvfqnlqv irgrilhnga ysltlqglgi swlglrslre lgsglalihh nthlcfvhtv 481 pwdqlfrnph qallhtanrp edecvgegla chqlcarghc wgpgptqcvn csqflrgqec 541 veecrvlqgl preyvnarhc lpchpecqpq ngsvtcfgpe adqcvacahy kdppfcvarc 601 psgvkpdlsy mpiwkfpdee gacqpcpinc thscvdlddk gcpaeqrasp ltsiisavvg 661 illvvvlgvv fgilikrrqq kirkytmrrl lqetelvepl tpsgampnqa qmrilketel 721 rkvkvlgsga fgtvykgiwi pdgenvkipv aikvlrents pkankeilde ayvmagvgsp 781 yvsrllgicl tstvqlvtql mpygclldhv renrgrlgsq dllnwcmqia kgmsyledvr 841 lvhrdlaarn vlvkspnhvk itdfglarll dideteyhad ggkvpikwma lesilrrrft 901 hqsdvwsygv tvwelmtfga kpydgipare ipdllekger lpqppictid vymimvkcwm 961 idsecrprfr elvsefsrma rdpqrfvviq nedlgpaspl dstfyrslle dddmgdlvda 1021 eeylvpqqgf fcpdpapgag gmvhhrhrss strsgggdlt lglepseeea prsplapseg 1081 agsdvfdgdl gmgaakglqs lpthdpsplq rysedptvpl psetdgyvap ltcspqpeyv 1141 nqpdvrpqpp spregplpaa rpagatlerp ktlspgkngv vkdvfafgga venpeyltpq 1201 ggaapqphpp pafspafdnl yywdqdpper gappstfkgt ptaenpeylg ldvpv
```

"Mutant" as used herein refers to a protein, such as ErbB-2, which comprises, consists of, or consists essentially of at least one amino acid substitution, insertion, deletion, and/or any combination thereof, i.e., the mutant can comprise 1, 2, 3, 4, 5, 6, 7, 8, 9, 10, 11, 12, 13, 14, 15, 20, 50, 100, or more amino acid substitutions, insertions, deletions, and/or any combination thereof. These substitutions, insertions, deletions, and/or any combination thereof may or may not be confined to one location of the protein sequence and may be at multiple locations of the protein amino acid sequence. The mutation, i.e., the substitution, insertion, deletion, and/or any combination thereof, can be made to a wild-type protein, i.e., a protein existing naturally in an organism or subject, a protein substantially identical to a wild-type protein, or to a protein already comprising a mutation.

Mutants of the present invention can be produced by any suitable method known in the art. Such methods include conventional techniques in molecular biology, microbiology, and recombinant DNA. These techniques are well known and are explained in, for example, Sambrook et al., 2001, Molecular Cloning: A Laboratory Manual, Third Edition, Cold Spring Harbor Laboratory Press, Cold Spring Harbor, N.Y.; DNA Cloning: A Practical Approach, Volumes I and II, 1985 (D. N. Glover ed.); Oligonucleotide Synthesis, 1984 (M. L. Gait ed.); Nucleic Acid Hybridization, 1985, (Hames and Higgins, eds.); Transcription and Translation, 1984 (Hames and Higgins, eds.); Animal Cell Culture, 1986 (R. I. Freshney ed.); Immobilized Cells and Enzymes, 1986, (IRL Press); Perbas, 1984, A Practical Guide to Molecular Cloning; the series, Methods in Enzymology (Academic Press, Inc.); Gene Transfer Vectors for Mammalian Cells, 1987 (J. H. Miller and M. P. Calos eds., Cold Spring Harbor Laboratory); and Methods in Enzymology Vol. 154 and Vol. 155 (Wu and Grossman, and Wu, eds., respectively); Current Protocols in Molecular Biology, John Wiley & Sons, Inc. (1994), and all more current editions of these publications. The mutant can be prepared by the construction of nucleotide sequences encoding the respective mutant and expressing the amino acid sequence in a suitable transfected host. The mutant can also be produced by chemical synthesis or by a combination of chemical synthesis and recombinant DNA technology. The mutant can be produced by obtaining the desired nucleotide sequence from a vector harboring the desired sequence or synthesized completely or in part using various oligonucleotide synthesis techniques known in the art, such as site-directed mutagenesis and polymerase chain reaction (PCR) techniques where appropriate.

"Substantially identical" or "substantially similar" as used herein refers to a reference amino acid sequence that is at least about 75%, 80%, 85%, 90%, 95%, 97%, 98% or 99% identical or similar, respectively, to the reference amino acid sequence. In some embodiments the reference amino acid sequence is the wild-type protein amino acid sequence.

"Dominant-negative inhibitor" and grammatical variations thereof as used herein refer to a mutant resulting from a dominant negative mutation. A dominant negative mutation occurs when a mutant affects one or more of the activities and/or functions of the normal, wild-type protein within the same cell in which it is present. A dominant negative mutation usually occurs if the product of the mutation (i.e., the dominant-negative inhibitor) can still interact with the same elements as the wild-type protein, but blocks or inhibits some aspect of the wild-type protein's activity and/or function. Such dominant-negative inhibitors can act in a variety of manners. "Dominant-negative inhibitor" as used herein is not intended to be limited in the manner in which the dominant-negative inhibitor acts as they can act in a variety of manners. In some cases, the dominant-negative inhibitor includes a binding domain and is capable of interacting with the wild-type protein to induce an inactive conformational change or the dominant-negative inhibitor may prevent an activating conformational change. In other cases, the dominant-negative inhibitor competitively binds to a substrate; thus, preventing binding of the substrate to the wild-type protein. Additionally, it is not intended to be limited in the manner in which the dominant-negative inhibitor is made as the dominant-negative inhibitors of the present invention may be made by any method known in the art. Some embodiments contemplate that it is produced synthetically. "Dominant-negative inhibitor" as used herein is also intended to include a mutant that provides partial inhibition or alteration of activity and/or function. It is not intended to require total inhibition or alteration, but in some embodiments the dominant-negative inhibitor may totally or substantially inhibit one or more functions of the wild-type protein. Exemplary dominant-negative inhibitors of the present invention include, but are not limited to, mutants of ErbB-2, which inhibit one or more activities and/or functions of endogenous (i.e., wild-type) ErbB-2 in a cell in which they are present. In some embodiments the ErbB-2 mutant inhibits cancer cell proliferation. In other embodiments the ErbB-2 mutant inhibits nuclear translocation of endogenous ErbB-2. In certain embodiments the ErbB-2 mutant inhibits cancer cell proliferation and inhibits nuclear translocation of endogenous ErbB-2.

"Subject" as used herein is generally a human subject and includes, but is not limited to, a cancer patient. The subject may be male or female and may be of any race or ethnicity, including, but not limited to, Caucasian, African-American, African, Asian, Hispanic, Indian, etc. The subject may be of any age, including newborn, neonate, infant, child, adolescent, adult, and geriatric. Subjects may also include animal subjects, particularly mammalian subjects such as canines, felines, bovines, caprines, equines, ovines, porcines, rodents (e.g. rats and mice), lagomorphs, primates (including non-human primates), etc., treated or screened for veterinary medicine or pharmaceutical drug development purposes.

"Cancer" or "cancers" that can be treated by the compounds, compositions and methods described herein include, but are not limited to, breast cancer, ovarian cancer, endometrial cancer, fallopian tube cancer, bone cancer such as osteogenic sarcoma, bladder cancer, pancreatic cancer, colorectal cancer, head and neck cancer, thyroid cancer, lung cancer, prostate cancer, leukemia, and brain cancer such as gliomas (e.g., GBM), etc. In some embodiments of the present invention the cancer treated is breast cancer.

In some embodiments of the present invention the cancer is characterized by overexpression of ErbB-2 (i.e., is ErbB-2 positive or HER2 positive). The terms "overexpression," "overexpresses," and grammatical variations thereof as used herein refer to expression of a protein in a cancer cell or tissue at a level higher than the level typically observed in a non-cancerous cell or tissue (i.e., normal or control cell or tissue). The normal level of expression for a cell or tissue may be assessed by measuring protein expression in a healthy portion of that tissue or cell or in a healthy subject. Methods for determining the level of expression of a protein both in a healthy cell and cancerous cell are well known in the art. In some embodiments, the level of expression of a protein that is overexpressed in a cancer cell is at least about 10%, 20%, 40%, 60%, 80%, 100%, 200%, 400%, 500%, 750%, 1,000%, 2,000%, 5,000%, 10,000%, or greater in the cancer cell relative to a control cell. Thus, a cancer cell that is characterized by overexpression of ErbB-2 is a cancer cell in which expression of ErbB-2 is at a higher level than the level typically observed in a non-cancerous cell or tissue.

In other embodiments the cancer is progesterone receptor positive, estrogen receptor positive, or both. Progesterone receptor positive and estrogen receptor positive are phenotypes of cancer that can be used to determine prognosis, treatment regimes, and/or follow up care. Cancer cells that are progesterone receptor positive indicates that the cancer cells have a receptor protein to which the hormone progesterone will bind. Progesterone receptor positive cancer cells may need progesterone to grow and will usually stop growing when treated with hormones that block progesterone from binding. Estrogen receptor positive cancer cells are cancer cells that have a receptor protein that binds the hormone estrogen. Cancer cells that are estrogen receptor positive may need estrogen to grow, and may stop growing or die when treated with substances that block the binding and actions of estrogen. The cancer, in some embodiments, is both progesterone receptor positive and estrogen receptor positive.

In certain embodiments the cancer overexpresses ErbB-2, is progesterone receptor positive, is estrogen receptor positive, or is any combination thereof. The cancer, in some embodiments, overexpresses ErbB-2 and is progesterone receptor positive.

In some embodiments of the present invention, the cancer may be resistant to one or more cancer therapies. The term "resistant," "resistance," and grammatical variations thereof as used herein refers to the response of a cell when contacted with an agent or therapy. A cancer cell is said to be resistant to a therapy or agent when the therapy or agent inhibits the cell growth or proliferation of the cancer cell to a lesser degree than is expected compared to an appropriate control, such as an average of other cancer cells that have been matched by suitable criteria, including but not limited to, tissue type, doubling rate or metastatic potential. In some embodiments, lesser degree refers to about 10%, 15%, 20%, 25%, 50%, or 100% less than the control cell. Exemplary cancer therapies that a cancer may become resistant to include, but are not limited to, ErbB-2 targeting therapies such as trastuzumab, lapatinib, and pertuzumab; hormonal therapies, such as tamoxifen and anastrozole; docetaxel; dacarbazine; paclitaxel; carboplatin; cisplatin; and gemcitabine.

"Proliferation" and "proliferating" as used herein refer to cells undergoing mitosis. Thus, "cancer cell proliferation" refers to cell division and a resulting increase in the number of cancer cells.

"Inhibit" as used herein refers to the prevention or slowing of a certain activity or function and includes a partial reduction in the activity. The term "inhibit" as used herein does not require complete blockage or elimination of the activity, but complete blockage or elimination of the activity may be seen in some embodiments of the present invention.

"Inhibition of proliferation" and grammatical variations thereof as used herein refer to a decrease in the rate of proliferation (e.g., a decrease or slowing in the rate of cellular division), cessation of proliferation (e.g., entry into G0 phase or senescence), or death of a cell, including necrotic cell death or apoptosis.

"Treat," "treating" or "treatment" as used herein refer to any type of treatment that imparts a benefit to a patient afflicted with a disease, including improvement in the condition of the patient (e.g., in one or more symptoms), delay in the progression of the disease, reduction in the severity of the disorder or the symptoms of the disorder, the disorder is partially or entirely eliminated, as compared to that which would occur in the absence of treatment, etc. Treatment does not require the achievement of a complete cure of the disorder and can refer to stabilization of disease.

"Effective amount" or "amount effective" as used herein refer to the amount of a therapeutic active agent that when administered or delivered to a subject by an appropriate dose and regimen produces the desired result.

"Pharmaceutically acceptable" as used herein means that the active agent is suitable for administration or delivery to a subject to achieve the treatments described herein, without unduly deleterious side effects in light of the severity of the disease and necessity of the treatment.

Active agents of the present invention may optionally be administered in conjunction with other compounds useful in the treatment of cancer. The other compounds may optionally be administered concurrently. As used herein, the word "concurrently" means sufficiently close in time to produce a combined effect (that is, concurrently may be simultaneously, or it may be two or more events occurring within a short time period before or after each other, e.g., sequentially). Simultaneous concurrent administration may be carried out by mixing the compounds prior to administration or delivery, or by administering or delivering the compounds at the same point in time but at different anatomic sites and/or by using different routes of administration.

II. Active Agents and their Methods of Use

Active agents or compounds of the present invention comprise, consist of, or consist essentially of mutants of ErbB-2. The mutants of ErbB-2 of the present invention cannot translocate to the nucleus of the cell in which they are present or are not as effective at translocating to the nucleus of the cell in which they are present compared to wild-type ErbB-2. The effectiveness of the ErbB-2 mutant in translocating to the nucleus of the cell in which it is present can be reduced by about 10%, 20%, 30%, 40%, 50%, 60%, 70%, 80%, 90%, 95%, 98%, 99% or 100% compared to wild-type ErbB-2. The inability or reduced effectiveness or ability of the ErbB-2 mutant to translocate to the nucleus of the cell may be due to many factors, such as, but not limited to, a mutation in a necessary binding domain or signaling sequence. In some embodiments of the present invention the ErbB-2 mutant lacks a functional nuclear localization signal. A "functional nuclear localization signal" as used herein refers to a nuclear localization signal having the characteristics of the wild-type protein. In certain embodiments the ErbB-2 mutant's nuclear localization signal does not allow for the mutant to be translocated to the nucleus or is not as effective as the nuclear localization signal of the wild-type ErbB-2 in translocating to the nucleus. The nuclear localization signal sequence of the ErbB-2 mutant may be mutated in any manner to result in a non-functional nuclear localization signal. A "non-functional nuclear localization signal" as used herein refers to a nuclear localization signal that inhibits translocation of the ErbB-2 mutant to the nucleus of the cell in which it is present. The inhibition provided by the non-functional nuclear localization signal can be a partial inhibition, i.e., result in a reduced effectiveness or ability of the mutant to translocate to the nucleus, or it can be a total inhibition of translocation to the nucleus. A non-functional nuclear localization signal includes where part or the entire nuclear localization signal sequence has been deleted in the ErbB-2 mutant.

The nuclear localization signal sequence of wild-type ErbB-2 comprises the amino acid sequence of KRRQQKIRKYTMRR (SEQ ID NO:3). In some embodiments of the present invention the nuclear localization signal sequence, e.g., SEQ ID NO:3, of the ErbB-2 mutant is deleted. In other embodiments amino acids at positions 676 to 689 of SEQ ID NO:2 are deleted and in certain embodiments amino acids at positions 676 to 692 of SEQ ID NO:2 are deleted. Deletion of the nuclear localization signal sequence may comprise removing or deleting a portion or segment of the nuclear localization signal sequence or removing or deleting the entire nuclear localization signal sequence. Deletion of the nuclear localization signal sequence does not foreclose the possibility that more of the ErbB-2 amino acid sequence than just the nuclear localization signal sequence is mutated. In some embodiments more of the ErbB-2 sequence is mutated than the amino acids of SEQ ID NO:3. The ErbB-2 mutants of the present invention may be mutated in more than one location. In other embodiments only a portion of the nuclear localization signal sequence or SEQ ID NO:3 is mutated. In some embodiments the mutant of ErbB-2 may be shortened by the number of amino acids in the nuclear localization signal sequence, i.e. the entire nuclear localization signal sequence is deleted. In other embodiments the nuclear localization signal sequence may be replaced or substituted with one or more amino acids.

In certain embodiments the ErbB-2 mutant is generated by deleting the nuclear localization signal sequence KRRQQKIRKYTMRR (SEQ ID NO:3) at amino acids 676 to 689 to result in the amino acid sequence of KLM at the deletion junction. For this ErbB-2 mutant N-terminal (aa 1 to 675) and C-terminal (aa 690 to 1234) portions of ErbB-2 can be PCR amplified using a high-fidelity PCR kit (Roche) and two sets of primers, 5'-ATCGCTAGCATGGAGCTG-GCGGCCTTG-3' (SEQ ID NO:4) with 5'-ATCAAGCTT-GATGAGGATCCCAAAGAC-3' (SEQ ID NO:5) and 5'-ATCAAGCTTATGCTGCTGCAGGAAACGGAG-3' (SEQ ID NO:6) with 5'-ATCACCGGTAACACTG-GCACGTCCAGACC-3' (SEQ ID NO:7), respectively. The amplified N-terminal portion that contains NheI (5' end) and HindIII (3' end) and the C-terminal portion that contains HindIII (5' end) and AgeI (3' end) can be digested and sequentially cloned into the pEGFP-N1 vector (BD Biosciences) (Giri et al., 2005).

In some embodiments of the present invention the mutants of ErbB-2 function as dominant-negative inhibitors of endogenous ErbB-2 (i.e., wild-type ErbB-2). Thus, the ErbB-2 mutant inhibits one or more functions and/or activities of endogenous ErbB-2 in a cell in which it is present. In some embodiments of the present invention the ErbB-2 mutant inhibits nuclear translocation of endogenous ErbB-2. The ErbB-2 mutant may inhibit nuclear translocation of endogenous ErbB-2 by about 10%, 15%, 20%, 25%, 50%, 60%, 70%, 80%, 90%, 95%, 98%, or more compared to a control cell or cancerous cell in which the ErbB-2 mutant is not present. ErbB-2 is a transmembrane protein that upon inducement or activation translocates or migrates to the nucleus of a cell. In some embodiments the ErbB-2 mutant prevents inducement or activation of endogenous ErbB-2 and in other embodiments it blocks or inhibits activated ErbB-2 from translocating to the nucleus. In certain embodiments of the present invention the ErbB-2 mutant inhibits progesterone receptor inducement or activation of endogenous ErbB-2. Inhibition of progesterone receptor inducement of endogenous ErbB-2, in some embodiments, inhibits nuclear translocation of endogenous ErbB-2. In some embodiments of the present invention the ErbB-2 mutant prevents or inhibits phosphorylation at one or more residues of endogenous ErbB-2. The ErbB-2 mutant, in some embodiments, prevents or inhibits progestin induced phosphorylation at one or more residues of endogenous ErbB-2.

In other embodiments of the present invention the ErbB-2 mutant inhibits cancer cell proliferation. The rate of cancer cell proliferation may be inhibited or slowed down by about 10%, 20%, 30%, 40%, 50%, 60%, 70%, 80%, 90%, 95%, 98%, or more compared to the rate the cancer cells were previously proliferating at or compared to the rate of cellular proliferation for other cancer cells that have been matched by suitable criteria, including but not limited to, tissue type, doubling rate or metastatic potential. In certain embodiments the ErbB-2 mutant inhibits progestin induced cancer cell proliferation.

Resistance to cancer therapies may occur with some types of cancer. In some embodiments of the present invention the ErbB-2 mutant overcomes or lessens resistance to one or more cancer therapies. Resistance to a cancer therapy may be decreased by the ErbB-2 mutant by about 10%, 20%, 30%, 40%, 50%, 60%, 70%, 80%, 90%, 95%, 98%, or more. Exemplary cancer therapies that a cancer may become resistant to include, but are not limited to, ErbB-2 targeting therapies such as trastuzumab, lapatinib, and pertuzumab; hormonal therapies, such as tamoxifen and anastrozole; docetaxel; dacarbazine; paclitaxel; carboplatin; cisplatin; and gemcitabine. In some embodiments the cancer is resistant to at least one ErbB-2 targeting therapy selected from the group consisting of trastuzumab, lapatinib, and pertuzumab. The cancer in other embodiments is resistant to at least one hormonal therapy selected from the group consisting of tamoxifen and anastrozole.

In certain embodiments the ErbB-2 mutant sensitizes the cancer to one or more cancer therapies or makes the cancer more susceptible to one or more cancer therapies. A cancer cell is more susceptible or sensitive to a cancer therapy or agent when the therapy inhibits the cell growth or proliferation of the cancer cell to a greater degree than is expected for an appropriate control, such as an average of other cancer cells that have been matched by suitable criteria, including but not limited to, tissue type, doubling rate or metastatic potential. In some embodiments, the cancer is more susceptible or sensitive to a cancer therapy by at least about 10%, 20%, 30%, 40%, 50%, 60%, 70%, 80%, 90%, 95%, 98%, or more compared to a control cell or the response of cancer cells prior to treatment with the ErbB-2 mutant. Exemplary cancer therapies that a cancer may become more sensitive to upon or after delivery or administration of the ErbB-2 mutant include, but are not limited to, ErbB-2 targeting therapies such as trastuzumab, lapatinib, and pertuzumab; hormonal therapies, such as tamoxifen and anastrozole; docetaxel; dacarbazine; paclitaxel; carboplatin; cisplatin; and gemcitabine.

In some embodiments of the present invention methods for treating cancer are provided and in certain embodiments methods for treating breast cancer are provided. In certain embodiments a method of treating cancer in a subject is provided comprising delivering to a subject in need of such treatment a mutant of ErbB-2 in an amount effective to inhibit cancer cell proliferation, wherein the mutant cannot translocate to a nucleus of a cell in which it is present and functions as a dominant-negative inhibitor of endogenous ErbB-2. In other embodiments a method for slowing the growth of a breast cancer tumor are provided comprising delivering to a subject in need of such treatment a mutant of ErbB-2 in an amount effective to inhibit cancer cell proliferation, wherein the mutant cannot translocate to a nucleus of a cell in which it is present and functions as a dominant-negative inhibitor of endogenous ErbB-2.

The method for treating cancer, in some embodiments, may comprise identifying a subject having a breast cancer tumor that is characterized by overexpression of ErbB-2 and/or is progesterone receptor positive; and delivering to the subject a mutant of ErbB-2 in an amount effective to inhibit cancer cell proliferation, wherein the mutant cannot translocate to a nucleus of a cell in which it is present and functions as a dominant-negative inhibitor of endogenous ErbB-2. In other embodiments a method of inhibiting the proliferation of a breast cancer cell is provided comprising delivering to a breast cancer cell a mutant of ErbB-2 in an amount effective to inhibit cancer cell proliferation, wherein the mutant cannot translocate to the nucleus of the cell and functions as a dominant-negative inhibitor of endogenous ErbB-2.

In some embodiments of the present invention other therapies, including but not limited to cancer therapies, known to one of skill in the art can be used in combination with the methods of the present invention. Exemplary therapies include, but are not limited to, radiotherapeutic agents and factors; surgery; antibiotics such as doxorubicin, daunorubicin, mitomycin, actinomycin D, and bleomycin; chemotherapeutic agents such as cisplatin, VP16, adriamycin, verapamil, and podophyllotoxin; tumor necrosis factor; plant alkaloids such as taxol, vincristine, and vinblastine; and alkylating agents such as carmustine, melphalan, cyclophosphamide, chlorambucil, busulfan, and lomustine. Additional exemplary cancer therapies include, but are not limited to, ErbB-2 targeting therapies such as trastuzumab (Herceptin®), lapatinib (Tykerb®), and pertuzumab (Omnitarg™); hormonal therapies, such as tamoxifen and anastrozole; docetaxel; dacarbazine; paclitaxel; carboplatin; and gemcitabine. In some embodiments the mutant of ErbB-2 is delivered in combination with at least one additional cancer therapy. In certain embodiments the at least one additional cancer therapy is an ErbB-2 targeting therapy selected from the group consisting of trastuzumab, lapatinib, and pertuzumab. In other embodiments the at least one additional cancer therapy is a hormonal therapy selected from the group consisting of tamoxifen and anastrozole.

In other embodiments of the present invention, the ErbB-2 mutant is delivered as a single-agent therapy to treat the cancer. A "single-agent therapy," as used herein, is one in which no other agent or therapy is utilized to treat the cancer or to sensitize the cancer cell to the ErbB-2 mutant, i.e., the ErbB-2 mutant is administered or delivered as a single therapeutic or agent to treat the cancer. In some embodiments the ErbB-2 mutant is delivered as a single-agent therapy in the first-line therapeutic approach. The "first-line therapeutic approach," "first-line therapy," and grammatical variations thereof, as used herein, refer to a therapeutic utilized in the initial treatment of a disease or disorder. The first-line therapeutic approach as used herein is not limited to single-agent therapies, but may also apply to combination therapies. Thus, in some embodiments the ErbB-2 mutant is utilized as a first-line therapy for the initial treatment of cancer, wherein the ErbB-2 mutant is delivered as a single-agent therapy or as a combination therapy. In other embodiments the ErbB-2 mutant is utilized as a therapeutic in the second-line therapeutic approach or in any subsequent therapeutic approach. The second-line therapeutic approach and any subsequent therapeutic approaches refer to therapeutic approaches after the initial therapeutic approach, i.e., the first-line therapeutic approach. These approaches may be the same as or different than the first-line therapeutic approach and may comprise a single-agent therapy or a combination therapy.

III. Pharmaceutical Formulations and Methods of Delivery

The active agents and/or compositions thereof described herein may be formulated for administration or delivery in a pharmaceutical carrier in accordance with known techniques. See, e.g., Remington, *The Science and Practice of Pharmacy* (9$^{th}$ Ed. 1995). In the manufacture of a pharmaceutical formulation according to the invention, the active compound(s) (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound(s) as a unit-dose formulation, for example, a tablet, which may contain from 0.01 or 0.5% to 95% or 99% by weight of the active compound. One or more active compounds may be incorporated in the formulations of the invention, which may be prepared by any of the well-known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Particular routes of parenteral administration include intrathecal injection, including directly into the tumor or a tumor resection cavity, and intraventricular injection into a ventricle of the brain.

Active compounds and compositions may be administered by intratumor injection (including tumors in any region such as tumors of the brain), or in the case of brain tumors injection into a ventricle of the brain.

Formulations of the present invention suitable for parenteral administration comprise sterile aqueous and non-aqueous injection solutions of the active compound, which preparations are preferably isotonic with the blood of the intended recipient. These preparations may contain antioxidants, buffers, bacteriostats and solutes that render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound or composition in a unit dosage form in a sealed container. The compound or composition is provided in the form of a lyophilizate that is capable of being reconstituted with a suitable pharmaceutically acceptable carrier to form a liquid composition suitable for injection thereof into a subject. The unit dosage form typically comprises from about 10 mg to about 10 grams of the compound or composition. When the compound or composition is substantially water-insoluble, a sufficient amount of emulsifying agent that is physiologically acceptable may be employed in sufficient quantity to emulsify the compound or composition in an aqueous carrier. One such useful emulsifying agent is phosphatidyl choline.

Further, the present invention provides liposomal formulations of the compounds disclosed herein and compositions thereof. The technology for forming liposomal suspensions is well known in the art. When the compound or composition thereof is an aqueous-soluble composition, using conventional liposome technology, the same may be incorporated into lipid vesicles. In such an instance, due to the water solubility of the compound or composition, the compound or composition will be substantially entrained within the hydrophilic center or core of the liposomes. The lipid layer employed may be of any conventional composition and may either contain cholesterol or may be cholesterol-free. When the compound or composition of interest is water-insoluble, again employing conventional liposome formation technology, the composition may be substantially entrained within the hydrophobic lipid bilayer that forms the structure of the liposome. In either instance, the liposomes that are produced may be reduced in size, as through the use of standard sonication and homogenization techniques.

Liposomal formulations containing the compounds disclosed herein or compositions thereof (e.g., ErbB-2 mutants), may be lyophilized to produce a lyophilizate, which may be reconstituted with a pharmaceutically acceptable carrier, such as water, to regenerate a liposomal suspension. Examples of liposomal formulations that can be used include the neutral lipid 1,2-dioleoyl-sn-glycero-3-phosphatidylcholine (DPOC) (See, e.g., Landen Jr. et al. (2005) Cancer Res. 65:6910-6918).

Other pharmaceutical compositions may be prepared from the water-insoluble compounds disclosed herein, or compositions thereof, such as aqueous base emulsions. In such an instance, the composition will contain a sufficient amount of pharmaceutically acceptable emulsifying agent to emulsify the desired amount of the compound or composition thereof. Particularly useful emulsifying agents include phosphatidyl cholines, and lecithin.

In addition to active compounds, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well-known in the art.

The therapeutically effective dosage of any one active agent, the use of which is in the scope of present invention, will vary somewhat from compound to compound, and patient to patient, and will depend upon factors such as the age and condition of the patient and the route of delivery. Such dosages can be determined in accordance with routine pharmacological procedures known to those skilled in the art.

As a general proposition, the initial pharmaceutically effective amount of the active compound or composition administered parenterally will be in the range of about 0.1 to 50 mg/kg of patient body weight per day, with the typical initial range of antibody used being 0.3 to 20 mg/kg/day, more preferably 0.3 to 15 mg/kg/day. The desired dosage can be delivered by a single bolus administration, by multiple bolus administrations, or by continuous infusion administration of active compound, depending on the pattern of pharmacokinetic decay that the practitioner wishes to achieve.

The active compound(s) is administered to the patient at one time or over a series of treatments. Depending on the type and severity of the disease, about 1 µg/kg to 15 mg/kg (e.g. 0.1-20 mg/kg) of active compound(s) is an initial candidate dosage for administration to the patient, whether, for example, by one or more separate administrations, or by continuous infusion. A typical daily dosage might range from about 0.1, 0.5, 1, 10 or 100 µg/kg up to 100, 200 or 500 mg/kg, or more, depending on the factors mentioned above. For repeated administrations over several days or longer, depending on the condition, the treatment is sustained until a desired suppression of disease symptoms occurs. A more particular dosage of the active compound will be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g., such that the patient receives from about two to about twenty, e.g. about six doses of the ErbB2 mutant). An initial higher loading dose, followed by one or more lower doses may be administered. An exemplary dosing regimen comprises administering an initial loading dose of about 0.5 to 10 mg/kg, followed by a weekly maintenance dose of about 0.5 to 10 mg/kg of the active compound. However, other dosage regimens may be useful. The progress of this therapy can be monitored by conventional techniques and assays.

Subjects treated by the methods of the present invention can also be administered one or more additional therapeutic agents. See U.S. Pat. No. 5,677,178. Chemotherapeutic agents may be administered by methods well known to the skilled practitioner, including systemically, direct injection into the cancer, or by localization at the site of the cancer by associating the desired chemotherapeutic agent with an appropriate slow release material or intra-arterial perfusing of the tumor. The preferred dose may be chosen by the practitioner based on the nature of the cancer to be treated, and other factors routinely considered in administering. See, e.g., U.S. Pat. No. 7,078,030.

Subjects may also be treated by radiation therapy, including, but not limited to, external beam radiotherapy, which may be at any suitable dose (e.g., 20 to 70 Gy or more per tumor, typically delivered over a fractionated schedule).

The ErbB-2 mutants of the present invention can be delivered or administered to a cell (e.g., a cancer cell) in vivo, ex vivo, or in vitro. In some embodiments the ErbB-2 mutant is delivered as a nucleic acid sequence that encodes and expresses the ErbB-2 mutant. In certain embodiments the ErbB-2 mutant is delivered to a subject as a nucleic acid sequence that encodes the mutant and expresses the mutant in the subject. The nucleic acid sequence may comprise deoxyribonucleic acids and/or ribonucleic acids.

Delivery of the nucleic acids of the present invention to an organelle, cell, tissue, and/or organism can be by any method known to those skilled in the art. One exemplary means of delivering or introducing genetic material into a cell is by transfection or transduction procedures. Transfection refers to the acquisition by a cell of new genetic material by incorporation of added nucleic acid molecules. Transfection can occur by physical or chemical methods. Transduction refers to the process of transferring nucleic acid into a cell using a DNA or RNA virus. Such methods for delivering nucleic acids to an organelle, cell, tissue, and/or organism include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859), including microinjection (Harlan and Weintraub, 1985; U.S. Pat. No. 5,789,215); by electroporation (U.S. Pat. No. 5,384,253; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538, 877 and 5,538,880); by agitation with silicon carbide fibers (Kaeppler et al., 1990; U.S. Pat. Nos. 5,302,523 and 5,464, 765); by *Agrobacterium*-mediated transformation (U.S. Pat. Nos. 5,591,616 and 5,563,055); by PEG-mediated transformation of protoplasts (Omirulleh et al., 1993; U.S. Pat. Nos. 4,684,611 and 4,952,500); by desiccation/inhibition-mediated DNA uptake (Potrykus et al., 1985), naked plasmid adsorption, and any combination of such methods. Through the application of techniques such as these, organelle(s), cell(s), tissue(s) or organism(s) may be stably or transiently transformed.

A vector may be utilized in some embodiments as a carrier for the nucleic acid sequence. A "vector" as used herein refers to a carrier nucleic acid molecule into which a nucleic acid sequence encoding the ErbB-2 mutant can be inserted for introduction into a cell where it can be replicated. The vector may comprise deoxyribonucleic acids (DNA) and/or ribonucleic acids (RNA). When the vector is a DNA molecule it is capable of being transcribed and subsequently translated into the ErbB-2 mutant. When the vector is a RNA molecule it is capable of being translated into the ErbB-2 mutant. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994). Non-limiting examples of vectors include plasmid vectors such as E. coli; phage vectors; and viral vectors such as adenoviral vectors, adeno-associated virus (AAV) vectors, retroviral vectors, vaccinia viruses, and Semliki Forest virus vectors.

Treatment of cells, or contacting cells, with recombinant nucleic acid molecules can take place in vitro, in vivo, or ex vivo. For ex vivo treatment, cells are isolated from an animal (e.g., a human), transformed (i.e., transduced or transfected in vitro) with a delivery vehicle containing a nucleic acid molecule encoding an ErbB-2 mutant, and then administered to a recipient. Procedures for removing cells from mammals are well known to those of ordinary skill in the art. In addition to cells, tissue or the whole or parts of organs may be removed, treated ex vivo and then returned to the patient. Thus, cells, tissue or organs may be cultured, bathed, perfused and the like under conditions for introducing the recombinant nucleic acid molecules of the invention into the desired cells.

For in vivo treatment, cells of a subject are transformed in vivo with a recombinant nucleic acid molecule of the invention. The in vivo treatment may involve, but is not limited to, systemic intravenous treatment with a recombinant nucleic acid molecule, local internal treatment with a recombinant nucleic acid molecule, such as by localized perfusion or topical treatment, and the like.

In certain embodiments of the present invention, a nucleic acid sequence encoding an ErbB-2 mutant is delivered to a cell or subject and is expressed in the cell or subject. In some embodiments the nucleic acid sequence encoding the ErbB-2 mutant is delivered to the cell or subject by injection. The injection (e.g., needle injection) may comprise one or more injections and can be, for example, subcutaneous, intradermal, intramuscular, intervenous, intraperitoneal, intrathecal, and/or intratumor. Methods of injection are well known to those of ordinary skill in the art (e.g., injection of a composition comprising a saline solution). Further embodiments of the present invention include the introduction of a nucleic acid by direct microinjection.

In other embodiments the nucleic acid sequence encoding the ErbB-2 mutant is delivered to the cell or subject by liposome-mediated transfection. When the nucleic acid sequence encoding the ErbB-2 mutant is delivered to the cell or subject by liposome-mediated transfection the nucleic acid is entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a nucleic acid complexed with Lipofectamine™ (Gibco BRL) or Superfect (Qiagen). In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

The present invention is explained in greater detail in the following non-limiting Examples.

EXAMPLES

MPA Induces Rapid ErbB-2 Activation and Nuclear Translocation

In this study we used primary cultures of C4HD epithelial cells from the model of mammary carcinogenesis induced by the synthetic progestin medroxyprogesterone acetate (MPA) in female BALB/c mice (2), and human breast cancer cell lines. C4HD cells display high levels of estrogen receptor (ER) and progesterone receptor (PR), overexpress ErbB-2 and ErbB-3, exhibit low ErbB-4 levels and lack EGF-R expression (2). We have long demonstrated that prolonged MPA treatment of C4HD cells resulted in upregulation of ErbB-2 expression as well as in stimulation of ErbB-2 tyrosine phosphorylation (2). Here, we found that MPA treatment of C4HD cells induces a rapid phosphorylation of a major ErbB-2 autophosphorylation site, tyrosine (Tyr) 1272 (Tyr 1222 in the human protein), as well as of the residue Tyr 927 (Tyr 877 in human), a site different from the autophosphorylation ones (12,31) (FIG. 1A). MPA effects were inhibited by preincubation with the antiprogestin RU486 (FIG. 1A). Same results were obtained by knockdown of PR gene expression with PR small interfering (si)RNAs (FIG. 1A).

Our findings in the human breast cancer cell line T47D also evidenced PR rapid activation of ErbB-2 (FIG. 1A). In order to further explore PR role, we used PR-null T47D cells (T47D-Y), in which we found that MPA had no effect on ErbB-2 phosphorylation at either Tyr 1222 or Tyr 877 (FIG. 1A). However, when we transfected T47D-Y cells with human PR-B (T47D-Y-PR-B), MPA treatment markedly enhanced ErbB-2 phosphorylation of both residues (FIG. 1A). Without being bound to a particular theory, these results indicate that MPA regulates the rapid activation of ErbB-2 acting through the classical PR. Progestin induction of rapid c-Src activation in mammary tumor cells, including our C4HD tumor model, is well acknowledged (5,19,21). On the other hand, a series of recent findings and ours as well, have shown that c-Src acts as an upstream effector of ErbB-2 (12,22,31).

Figure 1B:
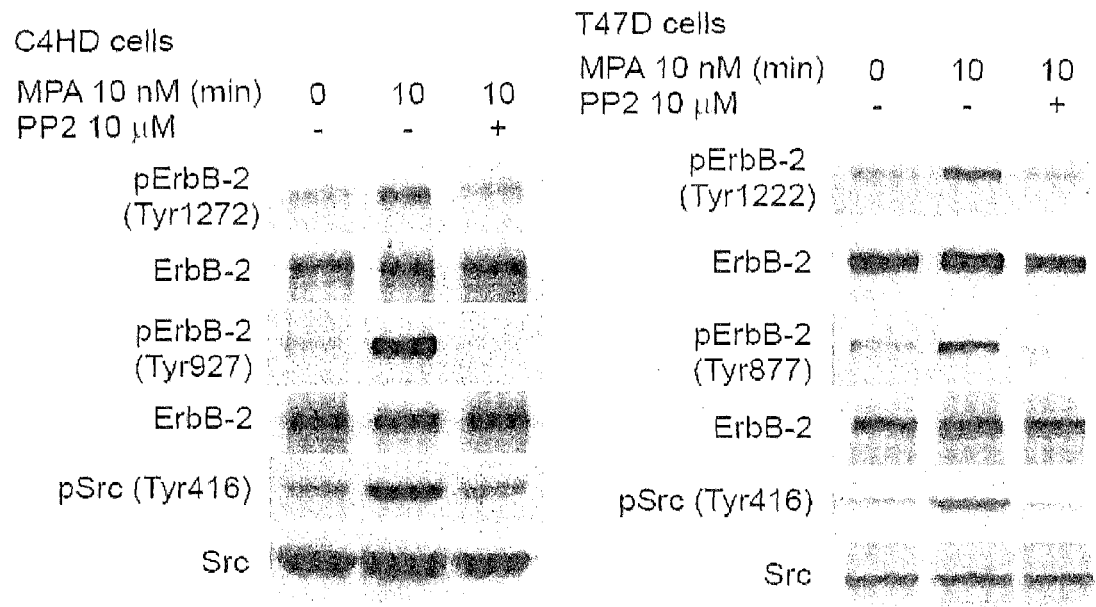
Figure 1C:
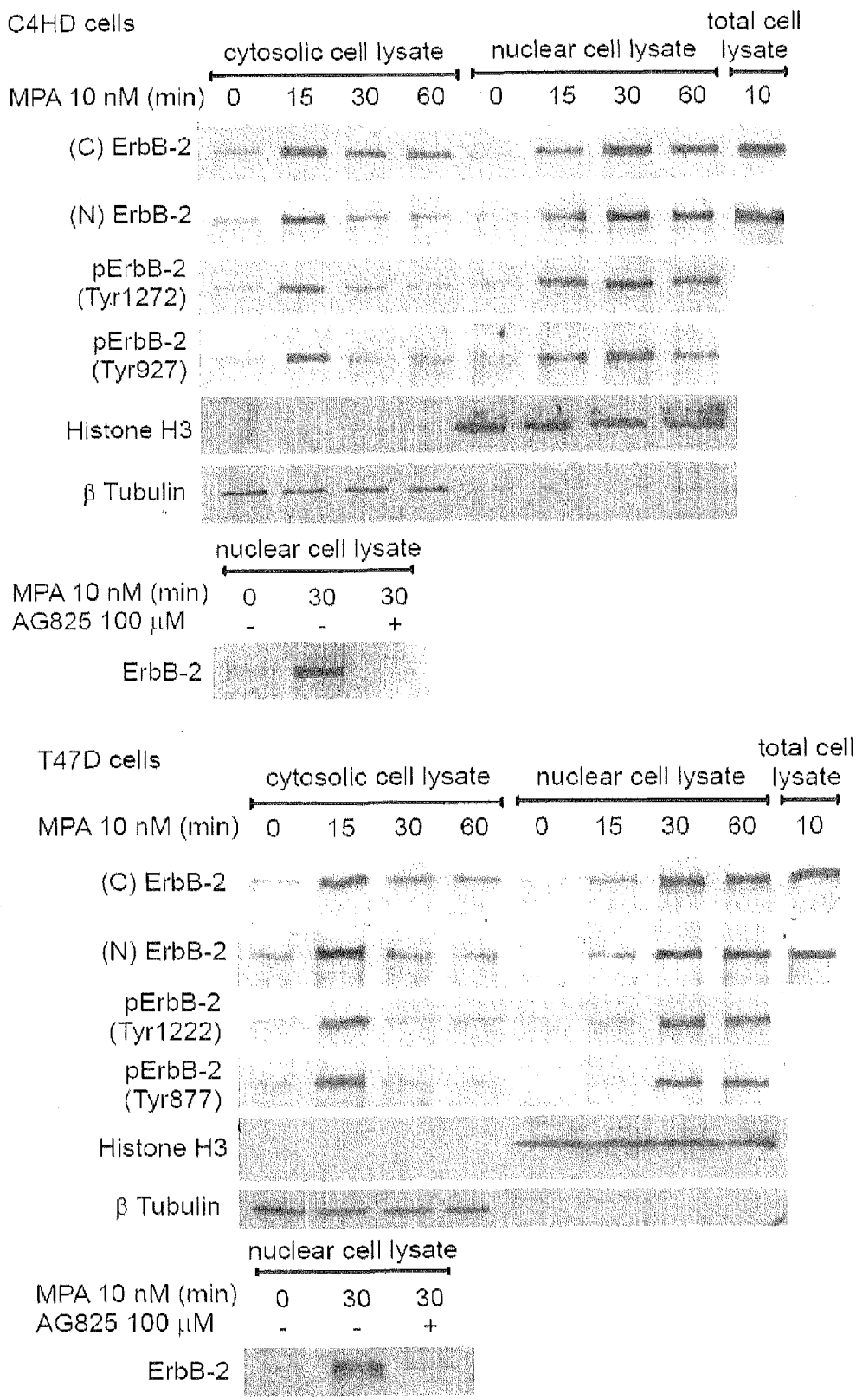

Therefore, we explored whether c-Src could be involved in MPA-induced ErbB-2 phosphorylation. We found that inhibition of c-Src activity in C4HD and T47D cells with the c-Src kinase inhibitor PP2 abrogated MPA stimulation of ErbB-2 phosphorylation at Tyr 1272/1222 and Tyr 927/877 (FIG. 1B). We then assessed whether MPA modulates ErbB-2 cellular localization. Subcellular fractionation and immunoblotting studies, using an antibody to the carboxy-terminal region (C) of ErbB-2, showed that MPA treatment of C4HD and T47D cells for 15 to 60 min induced a strong ErbB-2 protein nuclear translocation (FIG. 1C). Similar results were found when we used an antibody against the amino (N) terminus of the receptor (FIG. 1C). Full length ErbB-2 protein nuclear translocation was shown by the identical molecular weight of nuclear ErbB-2, as compared to ErbB-2 present in total cell extracts, corresponding to the entire 185 kDa protein (FIG. 1C), and shown as well by our findings with both the ErbB-2 carboxyl and amino terminus antibodies. Interestingly, this is the first report of a steroid hormone receptor induction of endogenous ErbB-2 migration to the nucleus.

Figure 1D:
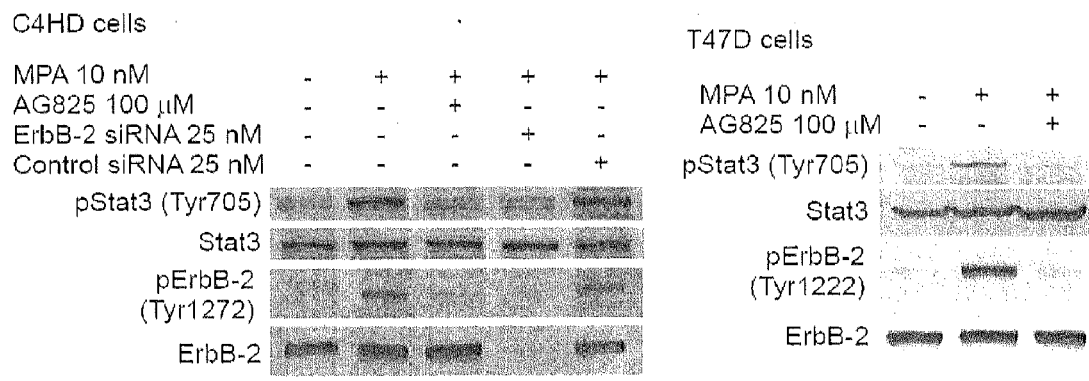
Figure 1E:
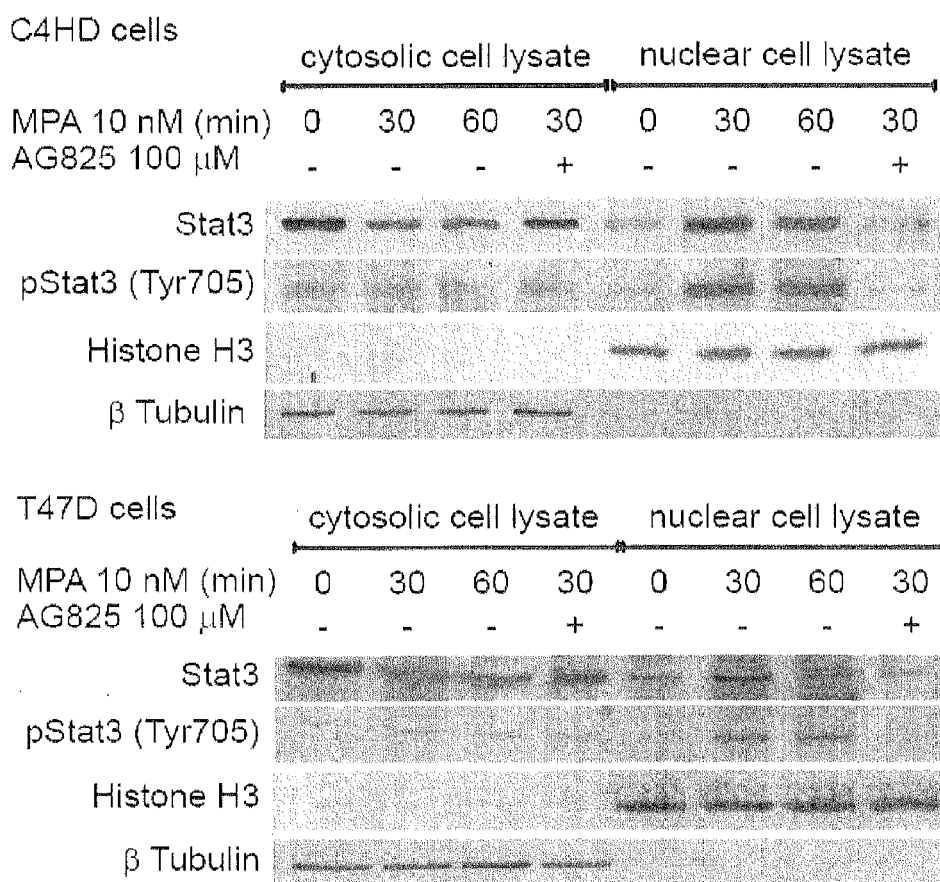

Our findings also showed high levels of nuclear ErbB-2 phosphorylation at Tyr 1272/1222 and Tyr 927/877 in C4HD and T47D cells (FIG. 1C). Preincubation of cells with the specific ErbB-2 tyrosine kinase inhibitor AG825, which prevented MPA-induced ErbB-2 Tyr phosphorylation, significantly inhibited ErbB-2 migration to the nucleus (FIG. 1C), indicating that ErbB-2 activation is an absolute requirement in this process. Our previous studies demonstrated that MPA induced rapid Stat3 Tyr 705 phosphorylation via a Jaks and c-Src-dependent pathway in breast cancer (21). Here, we found that blockage of ErbB-2 activity in C4HD and T47D cells and transfection of C4HD cells with ErbB-2 siRNAs designed to selectively knockdown mouse ErbB-2 expression inhibited WA-induced Stat3 phosphorylation (FIG. 1D), evidencing that ErbB-2 is also involved in MPA-induced Stat3 activation. To assess whether ErbB-2 and Stat3 are simultaneously present in the nucleus, we studied the kinetics of MPA-induced Stat3 nuclear translocation. We found that, upon stimulation of C4HD and T47D cells with MPA for 30 and 60 min, Stat3 is present at the nuclear compartment and strongly phosphorylated at Tyr 705 (FIG. 1E). Inhibition of Stat3 tyrosine phosphorylation by blockage with AG825 the activity of its upstream effector, ErbB-2, absolutely prevented Stat3 nuclear migration (FIG. 1E).

MPA Induces ErbB-2 and Stat3 Nuclear Colocalization

Figure 2A:
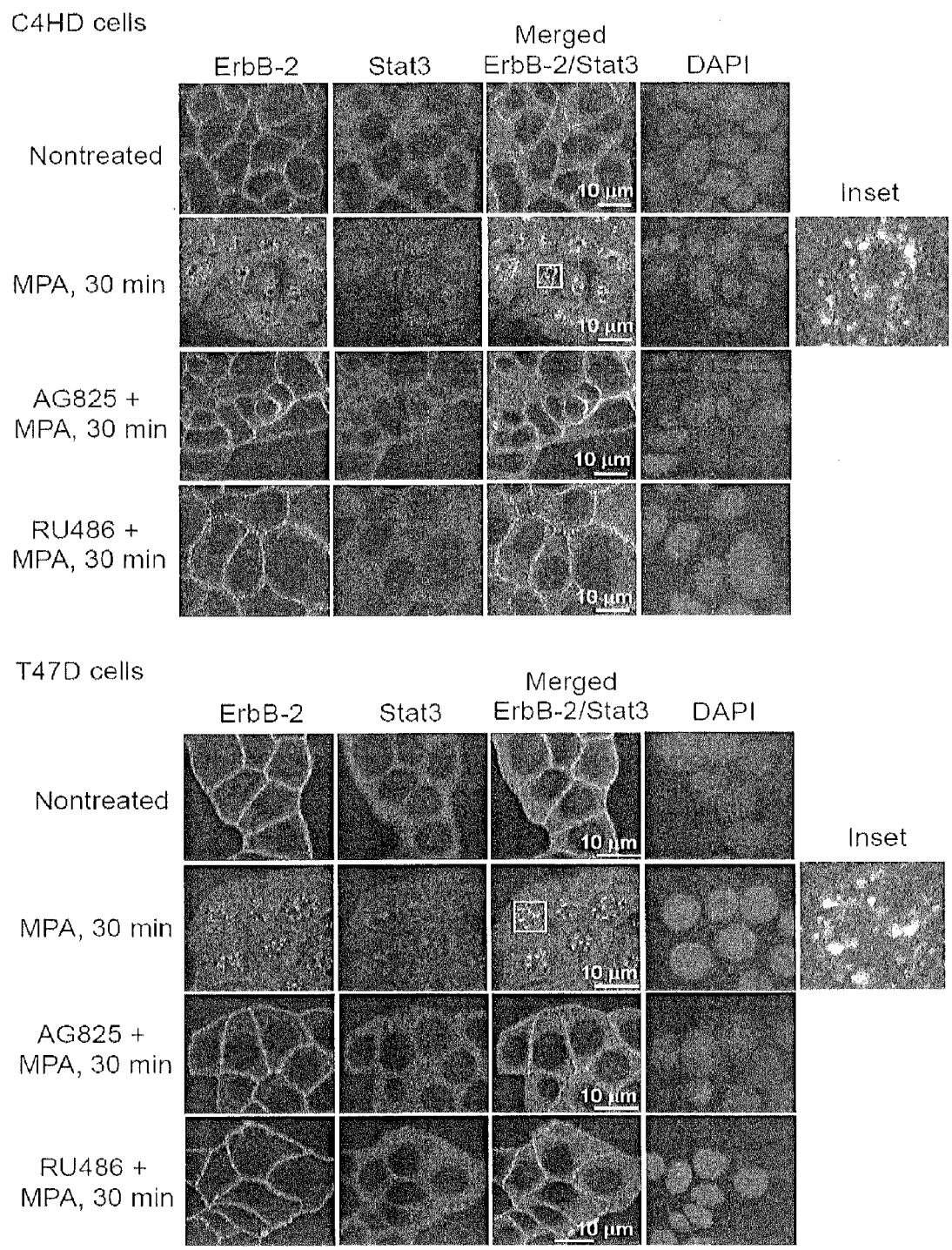
FIG. 2. MPA induces Stat3 and ErbB-2 nuclear colocalization and physical association (A) Cells were treated with MPA or pretreated with AG825 and RU486 before MPA stimulation. ErbB-2 (light gray) and Stat3 (light gray) were localized by immunofluorescence and confocal microscopy (see Materials and Methods for antibodies specifications). Merged images in the third panels of the second rows show MPA-induced ErB-2 and Stat3 nuclear colocalization, evidenced by the yellow foci. The boxed areas are shown in detail in the right inset. Nuclei were stained with DAPI (light gray). (B) Nuclear extracts from C4HD cells treated and untreated with MPA for 30 min were immunoprecipitated (IP) with ErbB-2 or Stat3 antibodies and analyzed by WB with the indicated phosphotyrosine antibodies. Membranes were reprobed with total protein antibodies. As control of the specificity of these proteins interaction, lysates were immunoprecipitated with rabbit immunoglobulin (IgG). Total cell lysates were blotted in parallel. Experiments in A and B were repeated three times with similar results.
Figure 2B:
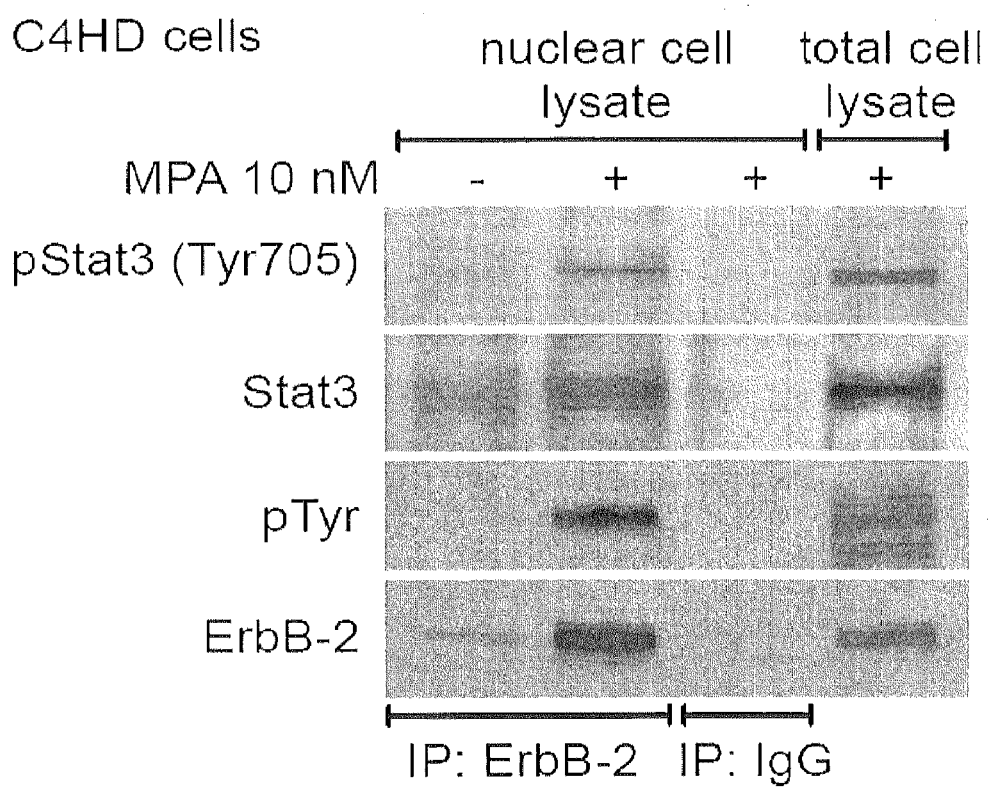
Figure 2B:
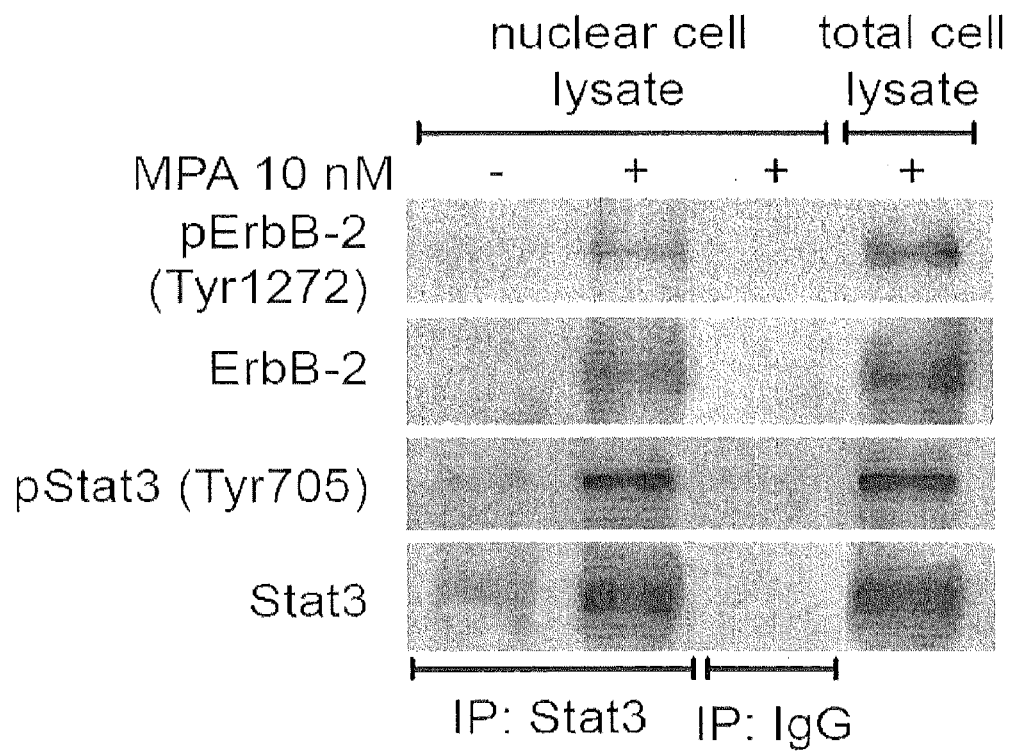

We then explored whether MPA treatment induces nuclear colocalization of Stat3 and ErbB-2 by using immunofluorescence staining and confocal microscopy. In the absence of MPA stimulation, the vast majority of ErbB-2 was localized in the cytoplasmic membrane of C4HD and T47D cells (FIG. 2A). MPA treatment of both cell types for 30 min resulted in ErbB-2 nuclear localization, detected as nuclear light gray foci (FIG. 2A). These results were obtained with the antibody against the ErbB-2 C-terminus. Inhibition of ErbB-2 Tyr 1222/1272 and Tyr 877/927 phosphorylation by AG825 abrogated ErbB-2 nuclear translocation (FIG. 2A), which is consistent with our cellular fractionation studies. On the other hand, in the absence of MPA treatment, Stat3 was diffusely located throughout the cytoplasm (FIG. 2A). MPA stimulation induced nuclear translocation of Stat3 in both cell lines (FIG. 2A). Inhibition of Stat3 tyrosine phosphorylation with AG825 absolutely prevented its nuclear migration (FIG. 2A). Abolishment of MPA-induced ErbB-2 and Stat3 activation with RU486 resulted in abrogation of both proteins migration to the nucleus (FIG. 2A). Notably, our findings also demonstrated that MPA treatment of C4HD and T47D cells resulted in strong nuclear colocalization of ErbB-2 and Stat3, as shown by the yellow foci in the merged images (FIG. 2A). Similar nuclear colocalization findings were obtained in T47D cells using an antibody raised against the NH2 terminus of ErbB-2 (data not shown). Significant ErbB-2 and Stat3 nuclear colocalization was also detected up to 60 min MPA stimulation (not shown). We did not observe Stat3 and ErbB-2 colocalization in the cytoplasm after MPA treatment for 30 min (FIG. 2A). Since we did not find significant levels of cytoplasmic phosphorylation in either protein at this time point (FIG. 1C), our results indicate that ErbB-2 and Stat3 only colocalize when both are phosphorylated. MPA-induced physical association between ErbB-2 and Stat3 in the nucleus was demonstrated through our coimmunoprecipitation studies in nuclear extracts from C4HD cells (FIG. 2B).

Figure 3A:
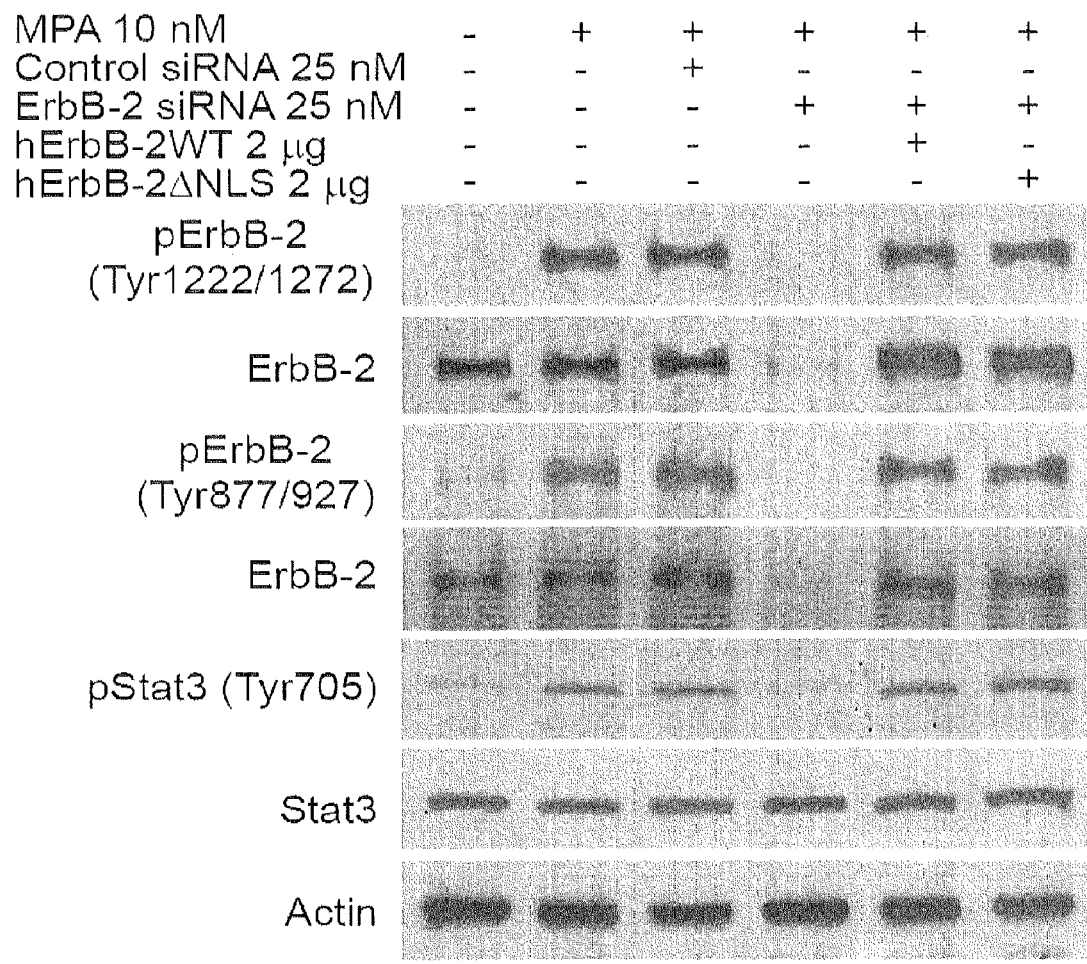
FIG. 3. Nuclear import of Stat3 mediated by MPA occurs independently of ErbB-2 nuclear localization (A) ErbB-2ΔNLS mutant induces Stat3 phosphorylation in response to MPA. Cells were transfected with siRNAs targeting mouse ErbB-2 or with control siRNAs and cotransfected with hErbB-2WT or hErbB-2ΔNLS plasmids when indicated, and then treated with MPA for 10 min. Cell lysates were analyzed by WB with pTyr ErbB-2 and Stat3 antibodies and then membranes were reprobed with the respective total protein antibody. (B) Cellular localization of Stat3 in ErbB-2siRNA-C4HD-hErbB-2ΔNLS cells treated with MPA. Green fluorescent protein (GFP) from the ErbB-2ΔNLS vector was visualized by direct fluorescence imaging (light gray). Nuclei were stained with DAPI (light gray). (C) Effect of hErbB-2ΔNLS on endogenous ErbB-2 nuclear migration. C4HD cells retaining endogenous ErbB-2 expression were transfected with the hErbB-2ΔNLS mutant and treated with MPA. Green fluorescent protein from hErbB-2ΔNLS expression vector was visualized as in B (light gray), and mouse ErbB-2 (light gray) was localized using an antibody that specifically recognizes the mouse protein. Solid arrows: cells transfected with hErbB-2ΔNLS, dashed arrows: wild-type C4HD cells that did not uptake the hErbB-2ΔNLS mutant. See Materials and Methods for specifications of antibodies used in B and C. Experiments in A to C are representative of three independent ones.
Figure 3B:
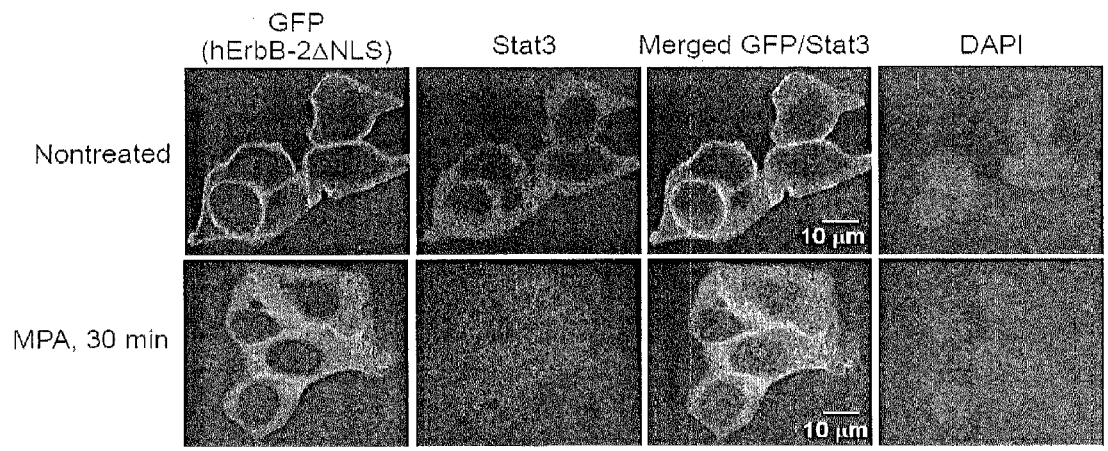

In order to study whether inhibition of ErbB-2 nuclear localization affected Stat3 transport, we used an RNA interference (RNAi)-reconstitution strategy. We transfected C4HD cells with ErbB-2 siRNAs specifically targeting mouse ErbB-2 in combination with either wild-type (WT) human ErbB-2 (ErbB-2siRNA-C4HD-hErbB-2WT cells) or a human ErbB-2 nuclear localization domain mutant (hErbB-2ΔNLS) (11), which is unable to translocate to the nucleus (ErbB-2siRNA-C4HD-hErbB-2ΔNLS cells). The characterization of hErbB-2ΔNLS response to MPA showed levels of hErbB-2ΔNLS phosphorylation on Tyr 1222 and Tyr 877 comparable to those of hErbB-2WT and of endogenous ErbB-2 (FIG. 3A). Similarly, hErbB-2ΔNLS induced Stat3 tyrosine phosphorylation upon MPA stimulation (FIG. 3A). These results indicate that ErbB-2ΔNLS retains its intrinsic tyrosine kinase activity, as already described (11), and they also for the first time identify ErbB-2ΔNLS role as an upstream activator in the mechanism of MPA induced Stat3 phosphorylation. In accordance with the pioneering work describing this mutant (11), our confocal microscopy studies revealed that hErbB-2ΔNLS did not translocate to the nucleus upon MPA treatment of ErbB-2siRNA-C4HD-hErbB-2ΔNLS cells, while a clear MPA-stimulated Stat3 migration to the nuclear compartment was detected in these cells (FIG. 3B). This indicates that nuclear import of Stat3 mediated by MPA occurs independently of ErbB-2 nuclear localization. The merged image in MPA treated cells, showing lack of proteins colocalization in the cytoplasm (FIG. 3B), further supports our finding that phosphorylation of both ErbB-2 and Stat3 is mandatory for their colocalization. Thus, although both proteins are present in the cytoplasmic compartment, only hErbB-2ΔNLS is phosphorylated there, since Stat3 which remains in the cytoplasm is unphosphorylated, as shown in FIG. 1E.

Figure 3C:
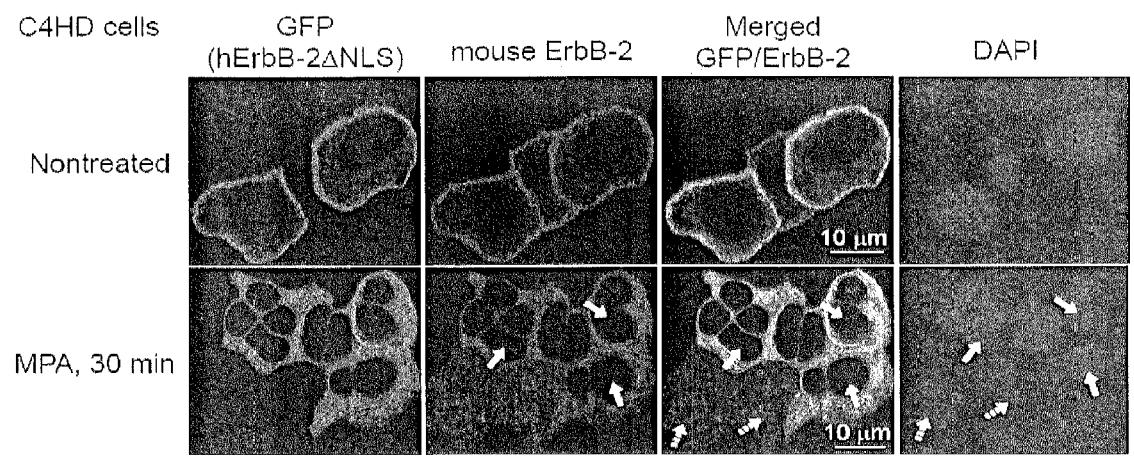

We then explored the effect of hErbB-2ΔNLS on the cellular localization of endogenous ErbB-2. For this purpose, we transfected the hErbB-2ΔNLS mutant to C4HD cells retaining endogenous ErbB-2 expression. Since hErbB-2ΔNLS is GFP-tagged (11), this mutant was visualized through direct fluorescence imaging. On the other hand, we visualized endogenous ErbB-2 by using an antibody which specifically recognizes mouse ErbB-2 and a rhodamine-labeled secondary antibody. Interestingly, our results showed that expression of hErbB-2ΔNLS absolutely prevented the nuclear translocation of endogenous mouse ErbB-2 (FIG. 3C), lower row, second panel, as example some cells are marked with solid arrows) for the first time revealing the function of hErbB-2ΔNLS as a dominant negative (DN) inhibitor of endogenous ErbB-2 nuclear migration. The merged image in FIG. 3C (lower row, third panel) shows the cytoplasmic presence and the colocalization (yellow spots) of hErbB-2ΔNLS and mouse ErbB-2 in cells transfected with the hErbB-2ΔNLS (solid arrows) in contrast to the clear migration of mouse ErbB-2 to the nucleus in the cells that did not uptake the hErbB-2ΔNLS (dashed arrows). To explore whether Stat3 cellular localization regulates the nuclear import of ErbB-2 mediated by MPA, we inhibited Jaks activity, which resulted in abolishment of MPA-induced Stat3 phosphorylation without affecting ErbB-2 activation. Inhibition of Stat3 tyrosine phosphorylation did not affect migration of ErbB-2 to the nucleus.

ErbB-2 Acts as Stat3 Coactivator

Figure 4A:
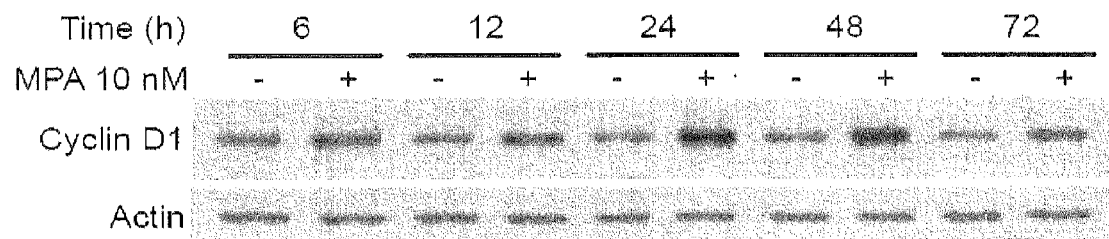
FIG. 4. ErbB-2 acts as a Stat3 coactivator in MPA-induced cyclin D1 promoter activation MPA induces cyclin D1 protein via ErbB-2 and Stat3. (A) Cyclin D1 expression was analyzed by WB. (B) Cells were preincubated with the indicated pharmacological inhibitors or transfected with Stat3, ErbB-2, and PR siRNAs and were then treated with MPA for 48 h. Cyclin D1 levels were studied by WB. Lower panel, control of inhibition of Stat3 expression by siRNAs. Experiments in A and B were repeated three times with similar results. (C) MPA induces cyclin D1 promoter activation via Stat3. Cells were transfected with a 1,745-bp length human cyclin D1 promoter luciferase construct containing the GAS sites indicated in the upper diagram. C4HD cells were also transfected with constructs truncated at positions −963, −262 and −141, as shown in the diagram. When indicated, cells were cotransfected with the Stat3Y705-F expression vector. After transfection, cells were treated with MPA for 24 h. Results are presented as n fold induction of luciferase activity with respect to control cells untreated with MPA. The data shown represent the mean of six independent experiments for each cell type±SEM. For b vs. a, and c vs. b: $P<0.001$. (D) ErbB-2 acts as a Stat3 coactivator. Top: C4HD cells were transfected with the 1,745 cyclin D1 promoter construct as described in C and were also cotransfected with hErbB-2WT or hErbB-2ΔNLS vectors when indicated and treated with MPA as in C. The relative light units of luciferase obtained in the transient transfection assays were normalized by the arbitrary densitometric values of phosho Tyr705/total Stat3 obtained in the WB shown in the bottom panel, and data are presented as n fold induction of cyclin D1 promoter activity relative to cells untreated with MPA. Data shown represent the mean of three independent experiments±SEM. For b vs. a, c vs. b, d vs. b: $P<0.001$. Bottom: Cells were transfected with hErbB-2WT or hErbB-2ΔNLS and were then treated with MPA for 10 min. Stat3 phosphorylation was studied by WB as described in FIG. 1D.
Figure 4B:
Figure 4B:

We then explored the nature of the nuclear interaction between ErbB-2 and Stat3. Although Stat3 function as a transcription factor is well acknowledged, the coactivators that modulate Stat3 activity remain, however, poorly studied. On the other hand, even though seminal findings unraveled ErbB-2 role as a transcription factor (30), the capacity of ErbB-2 to act as a transcriptional coactivator remains completely unknown. We consequently built up a novel hypothesis, namely that ErbB-2 could modulate breast cancer growth acting as a coactivator of Stat3. Through database (MatInspector) and literature searches, we first identified cancer-related genes that contain Stat3 response elements but lack HAS sites. We found that cyclin D1 was a prospective gene to analyze, since it contains Stat3 binding sites in its promoter but lacks HAS sequences. Cyclin D1 is a particularly attractive gene because its involvement in breast cancer growth, as well as progestin induction of cyclin D1 gene expression have long been shown (4,10,23, 25). Cyclin D1 promoter lacks a canonical PRE. Here, we found that MPA treatment of C4HD cells induced a significant increase in cyclin D1 protein levels (FIG. 4A). Preincubation with RU486 and silencing PR expression abrogated MPA effects (FIG. 4B). Constitutively activated Stat3 and ErbB-2 have been recently found to stimulate cyclin D1 promoter activity in breast and prostate cancer cells, respectively (8,15). Therefore, we sought out to determine the participation of ErbB-2 and Stat3 in MPA upregulation of cyclin D1 expression. Inhibition of ErbB-2 activity or knockdown of ErbB-2 expression significantly inhibited MPA capacity to induce cyclin D1 expression (FIG. 4B). Abolishment of MPA-induced Stat3 activation or silencing Stat3 expression with Stat3 siRNAs also abrogated MPA upregulation of cyclin D1 protein levels (FIG. 4B). These findings demonstrate that both ErbB-2 and Stat3 are key players in the mechanism of MPA-induced cyclin D1 expression.

Figure 4C:
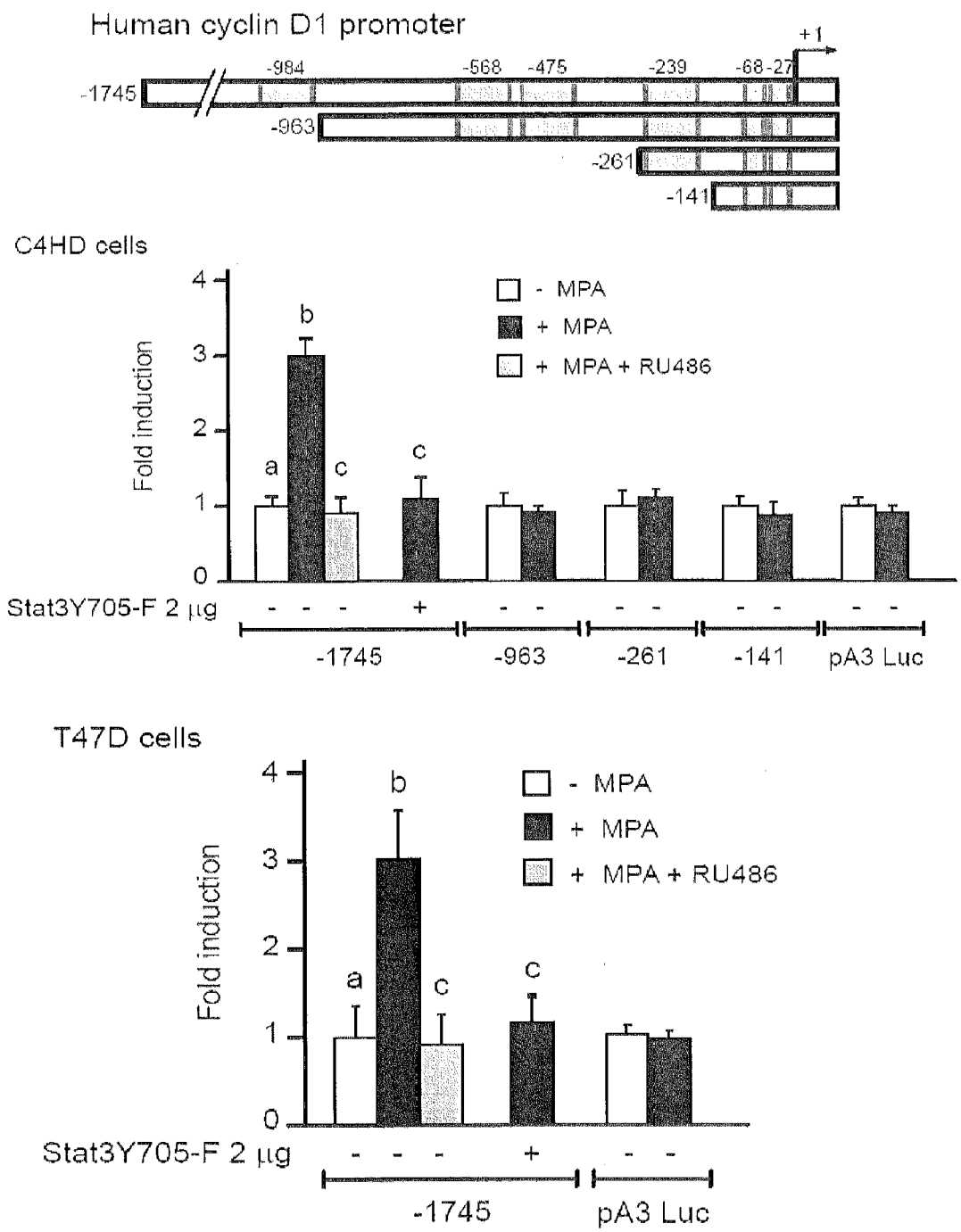

We also found that MPA modulates cyclin D1 expression in T47D cells via ErbB-2 and Stat3. Next, we assessed whether MPA regulates the transcriptional activity of the cyclin D1 promoter directly via induction of Stat3 binding to its response elements. C4HD and T47D cells were transiently transfected with a 1,745-bp human cyclin D1 promoter luciferase construct containing Stat3 binding sites, named GAS sites, at positions −984, −568, −475, −239, −68 and −27 (FIG. 4C, upper diagram) (15). MPA treatment of both cell types resulted in a 3-fold increase in cyclin D1 promoter activity, which was completely abrogated by RU486 (FIG. 4C). Cotransfection with a DN Stat3 expression vector, Stat3Y705-F, absolutely inhibited MPA effects (FIG. 4C). In order to further demonstrate that MPA activates cyclin D1 promoter via direct Stat3 binding to the GAS sequences, C4HD cells were transfected with cyclin D1 promoter constructs truncated at positions −963, −261, and −141, in which one, three, or four GAS sites, respectively, were excluded (FIG. 4C, upper diagram). Interestingly, MPA capacity to induce cyclin D1 promoter activation significantly decreased when the Stat3 binding site at position −984 was eliminated and no further effect were found by the loss of the rest of the GAS sites (FIG. 4C).

Figure 4D:
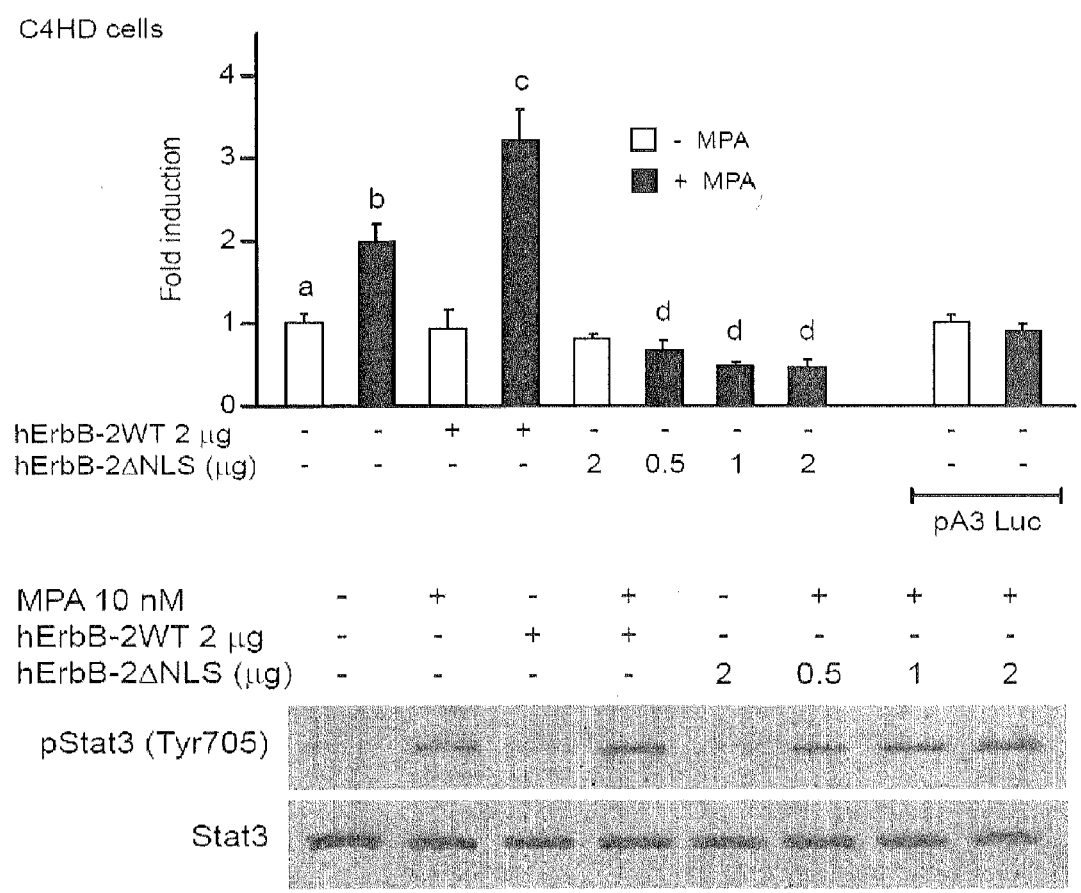

We then specifically evaluated whether ErbB-2 acts as a transcriptional coactivator of Stat3 in the mechanism of MPA-induced cyclin D1 promoter activation. As shown in FIG. 4D, we found that overexpression of hErbB-2WT significantly enhanced cyclin D1 promoter activation induced by MPA via Stat3. In the absence of MPA, ErbB-2WT did not modulate basal levels of Stat3 transcriptional activity under the assay conditions used. On the other hand, transfection of C4HD cells with the hErbB-2ΔNLS resulted in abrogation of MPA-stimulated Stat3 activation of the cyclin D1 promoter (FIG. 4D). This finding is consistent with ErbB-2ΔNLS function as a DN inhibitor of endogenous ErbB-2 nuclear migration, as we here identified (FIG. 3C), resulting in a scenario in which Stat3 is located in the nucleus and binds to the cyclin D1 promoter, but ErbB-2 is not available to act as coactivator. Notably, we are here defining a new class of transcriptional complex in which the transcription factor itself (Stat3) is a downstream target of its coactivator (ErbB-2). Therefore, simultaneous to the transient transfection assays, we also performed Western blots in which we studied Stat3 activation levels in cells transfected with hErbB-2WT or hErbB-2ΔNLS by assessing Stat3 Tyr 705 phosphorylation. As shown in FIG. 4D, transfection of C4HD cells with hErbB-2WT or hErbB-2ΔNLS resulted in higher levels of Stat3 Tyr705 phosphorylation upon MPA stimulation than those observed in wild-type C4HD cells also stimulated with MPA. To normalize for this modulation in Stat3 Tyr705 phosphorylation levels, which is directly involved in Stat3 transcriptional activity (7), phospho Stat3 bands in the immunoblots underwent densitometry and values were normalized to total Stat3 bands. Then, the luciferase units obtained in the transfection assays were divided by the densitometric values of phosho Tyr705/total Stat3. FIG. 4D shows data analysis thus performed, clearly evidencing that Stat3 activation of cyclin D1 promoter was not due to increase in Stat3 phosphorylation at Tyr705, but to ErbB-2 enhancement of MPA-induced Stat3 transcriptional activity. These findings identify a novel function of ErbB-2 as a Stat3 coactivator.

In order to further explore ErbB-2 function as coactivator, we took advantage of our RNAi-reconstitution model in C4HD cells. Expression of the ErbB-2ΔNLS in C4HD cells in which endogenous ErbB-2 was abolished by ErbB-2 siRNAs, failed to reconstitute Stat3 activation of the cyclin D1 promoter. To confirm that the role of ErbB-2 as a Stat3 coactivator is not restricted to the cyclin D1 promoter, or to a specific cell line, we transfected C4HD and T47D cells with a luciferase reporter plasmid containing four copies of the m67 high-affinity Stat3 binding site (7). MPA-induced Stat3 transcriptional activation measured using this reporter was significantly enhanced by cotransfection with hErbB-2WT.

Figure 5A:
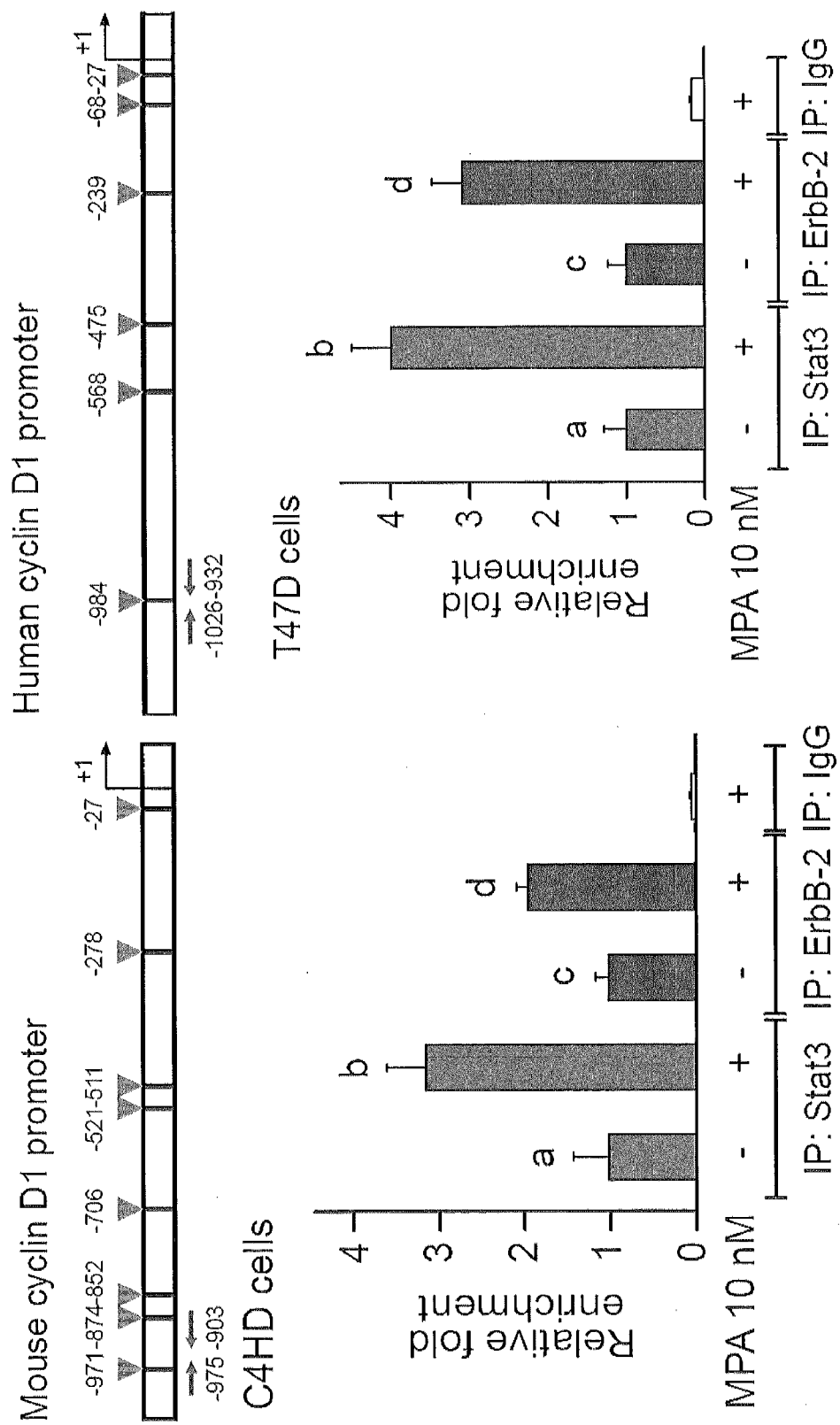
FIG. 5. MPA induces in vivo binding of Stat3 and ErbB-2 to the cyclin D1 promoter (A) Recruitment of Stat3 and ErbB-2 to the cyclin D1 promoter was analyzed by ChIP in cells treated with MPA for 30 min. Immunoprecipitated DNA was amplified by qPCR using primers (horizontal gray arrows) flanking the GAS sites (vertical gray arrows) indicated in top panels. The arbitrary qPCR number obtained for each sample was normalized to the input, setting the value of the untreated sample as 1. Data are expressed as fold chromatin enrichment over untreated cells. For b vs. a, and d vs. c: $P<0.001$. (B) Sequential ChIP. Chromatins from cells treated as described in A were first immunoprecipitated with a Stat3 antibody, and then were re-immunoprecipitated using an ErbB-2 antibody. qPCR and data analysis were performed as detailed in A. For b vs. a: $P<0.001$. Results in A and B are mean±SEM from three independent experiments. IgG was used as a negative control. (C) C4HD cells were treated with MPA for 48 h or transfected with increasing amounts of hErbB-2ΔNLS expression vectors before MPA stimulation. Cyclin D1 protein levels were analyzed by WB.
Figure 5B:
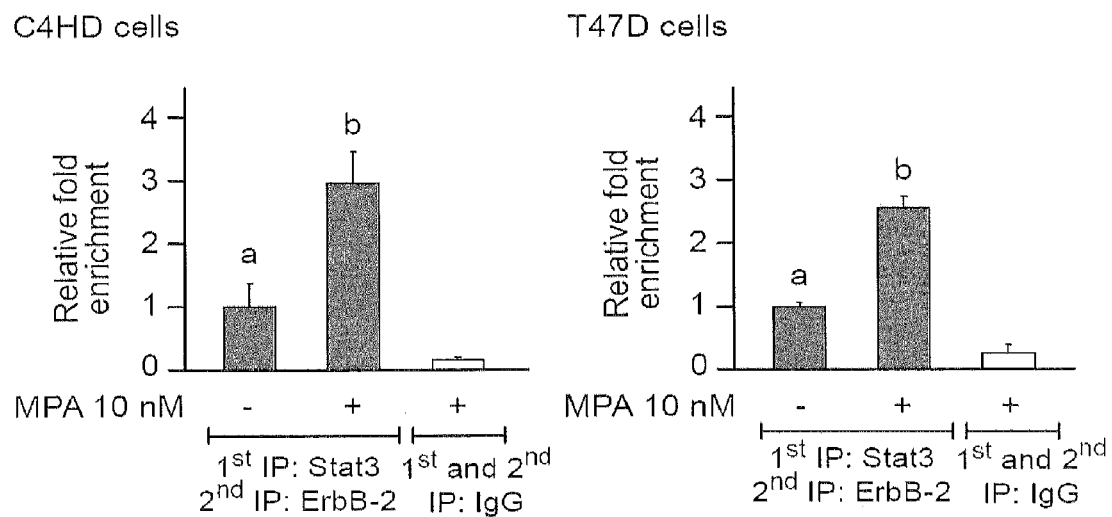
Figure 5C:
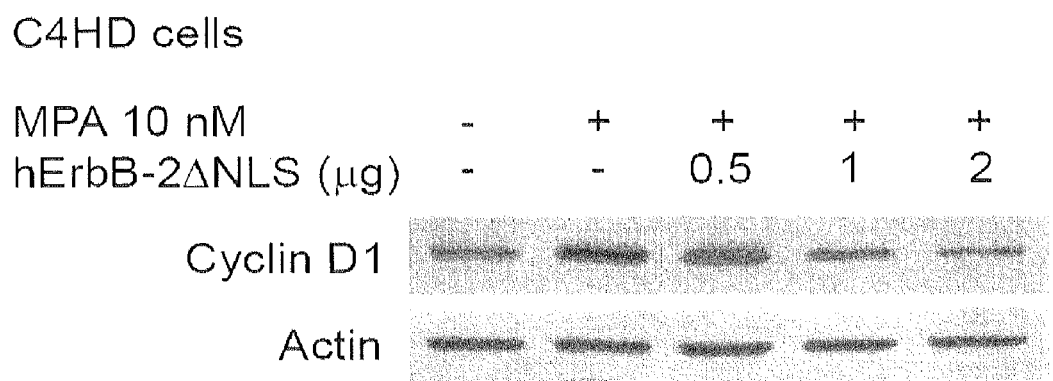

In Vivo Binding of the Stat3 and ErbB-2 Transcriptional Complex to the Cyclin D1 Promoter To assess the specific association of Stat3 and ErbB-2 in the context of living cells we used a ChIP assay. Our findings in C4HD cells using primers spanning two GAS sites showed significant and specific MPA-induced binding of both nuclear Stat3 and ErbB-2 to the mouse cyclin D1 promoter after 30 min treatment (FIG. 5A). Importantly, both proteins associate with the cyclin D1 promoter at the same time, suggesting that they function together in the process of MPA-mediated cyclin D1 promoter activation. We also found that MPA caused a striking increase in the occupancy by both Stat3 and ErbB-2 of the human cyclin D1 promoter in T47D cells using a pair of primers flanking the −984 GAS site (FIG. 5A). We then assessed whether Stat3 and ErbB-2 simultaneously bind to the cyclin D1 gene promoter, using sequential ChIP in C4HD and T47D cells, Quantitative real-time PCR analysis clearly evidenced that Stat3 and ErbB-2 co-occupy the cyclin D1 promoter after 30 min of stimulation with MPA (FIG. 5B). To further confirm that a nuclear Stat3/ErbB-2 complex regulates cyclin D1 expression in breast cancer, we explored the levels of cyclin D1 protein in C4HD cells transfected with increasing amounts of hErbB-2ΔNLS. Our results showed that levels of MPA-induced cyclin D1 were significantly reduced by hErbB-2ΔNLS expression, as compared to those found in wild-type C4HD cells (FIG. 5C).

The Nuclear Stat3/ErbB-2 Complex Regulates Breast Cancer Cell Proliferation

Figure 6A:
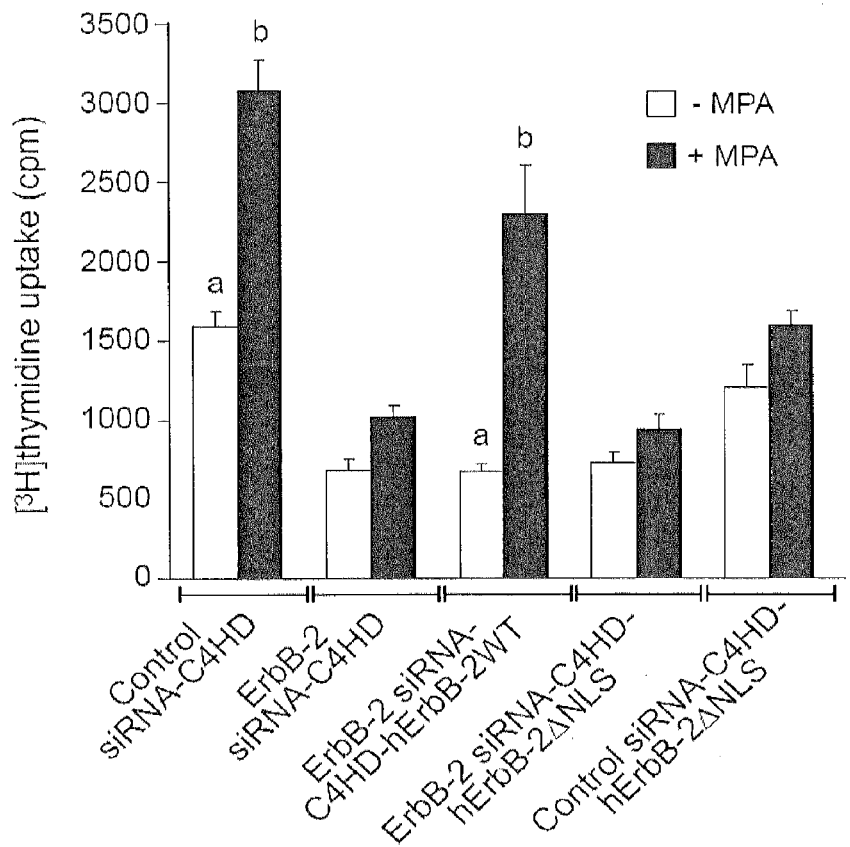
FIG. 6. Nuclear Stat3/ErbB-2 complex regulates in vitro breast cancer proliferation (A) Endogenous ErbB-2 expression was silenced by transfection with ErbB-2 siRNAs and expressions of either hErbB-2WT or hErbB-2ΔNLS were restored by cotransfection with the respective plasmids. Cells were treated with MPA 48 h and incorporation of [3H]thymidine was used as a measure of DNA synthesis. Data are presented as means±standard deviations ($P<0.001$ for b versus a). (B) C4HD cells were transfected with control siRNA (top) and cotransfected with hErbB-2ΔNLS (bottom) before MPA stimulation for 48 h and were then stained with PI and analyzed for cell cycle distribution by flow cytometry. The experiments shown in A and B are representative of a total of three.
Figure 6B:
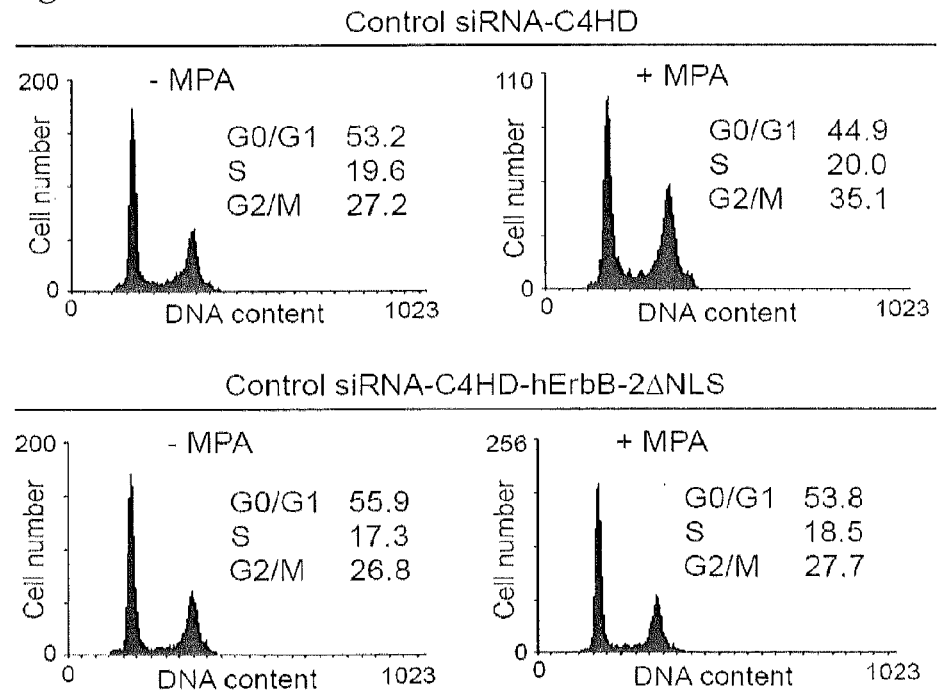

To investigate the correlation between MPA-induced assembly of the nuclear Stat3/ErbB-2 complex and cell growth, we examined the in vitro proliferative response of ErbB-2-siRNA-C4HD-hErbB-2ΔNLS cells to MPA. As showed in FIG. 6A, ErbB-2-siRNAC4HD-ErbB-2ΔNLS cells were completely unresponsive to MPA stimulation. This finding reveals a direct correlation between ErbB-2 nuclear localization and progestin-induced breast cancer growth. Since we found that hErbB-2ΔNLS acts as a DN negative inhibitor of endogenous ErbB-2 nuclear translocation, we next addressed whether transfection of hErbB-2ΔNLS to C4HD cells expressing ErbB-2 (Control siRNA-C4HD-ErbB-2DNLS) affects MPA-induced growth. Our results showed that under these cell conditions, the response to MPA was abrogated (FIG. 6A), for the first time identifying the function of hErbB-2ΔNLS as a DN inhibitor of endogenous ErbB-2 proliferative effects in breast cancer. Proliferation was also evaluated by propidium iodide staining and flow cytometry analysis with similar results. FIG. 6B shows our results in Control siRNA-C4HD-ErbB-2ΔNLS cells indicating their lack of proliferative response to MPA.

Abrogation of ErbB-2 Nuclear Localization Inhibits In Vivo Growth of Breast Tumors Expressing Steroid Hormone Receptors and ErbB-2

Figure 7A:
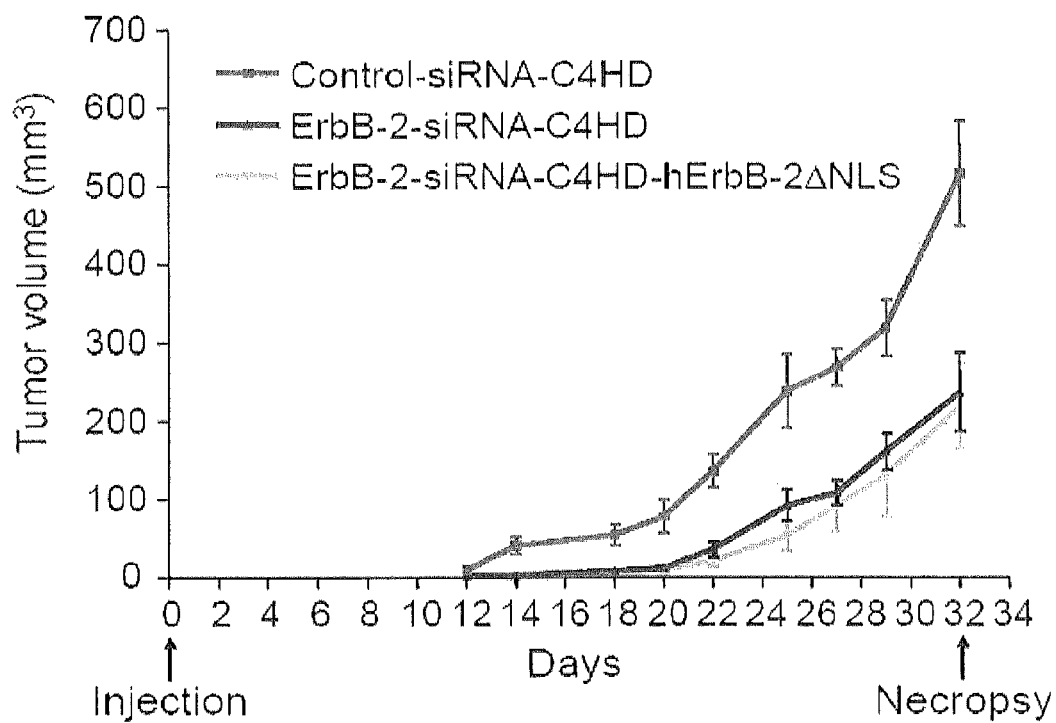
FIG. 7. In vivo blockage of ErbB-2 nuclear localization (A and B) Cells (106) from each experimental group were inoculated subcutaneously (s.c.) in mice treated with MPA and tumor volume was calculated as described in Materials and Methods. Bottom: Decrease in tumor mass in mice injected with C4HDhErbB-2ΔNLS cells as compared to mice injected with C4HD cells. Each point represents the mean volume±SEM of 6 independent tumors for all experimental groups except for ErbB-2-siRNA-C4HD and ErbB-2-siRNA-C4HD-hErbB-2ΔNLS groups which contained 4 tumors. (C) Content of hErbB-2ΔNLS. GFP expression levels were determined by flow cytometry. Shown is a representative sample of each tumor type. (D) Tumor lysates were analyzed by WB with the indicated phosphoprotein antibodies and membranes were reprobed with the respective total protein antibody. Shown are two representative samples of mice injected with C4HD (1 and 2) and with C4HD-hErbB-2ΔNLS cells (3 and 4). Lane 5, C4HD cells nontreated with MPA used as control of protein phosphorylation state. (E) ChIP analysis in tumor samples. The DNA-protein complexes were pulled down with the Stat3 and ErbB-2 antibodies or with control IgG and the resulting DNA was amplified by qPCR using primers indicated in FIG. 5. Results are expressed as fold over IgG control and represent the average of three replicates±SEM. Shown is a representative sample of each tumor type.

Our breast cancer model has unique features that make it particularly attractive for in vivo studies targeting ErbB-2. Since C4HD tumors overexpress ErbB-2 and also have high levels of ER and PR, they resemble a phenotype present in approximately 50% of human breast cancers that overexpress ErbB-2 and associated with resistance to hormonal treatment (20). In this study, Control-siRNA-C4HD, ErbB-2-siRNA-C4HD, and ErbB-2-siRNA-C4HD-hErbB-2ΔNLS cells were inoculated subcutaneously (s.c.) in mice treated with MPA. We are here describing a representative experiment of a total of three. All mice (n=6) injected with Control-siRNA-C4HD cells developed tumors which became palpable after 12 days' inoculation. On the contrary, only 4 out of 6 mice injected with ErbB-2-siRNA-C4HD cells or with ErbB-2-siRNA-C4HD-hErbB-2ΔNLS cells developed tumors with a delay of 4 days in tumor latency, as compared with tumors from the control group. Mean volume (FIG. 7A) and growth rates (Table 3) of tumors developed from either ErbB-2-siRNA-C4HD or from ErbB-2-siRNA-C4HD-hErbB-2ΔNLS cells were significantly lower than those of tumors from the control group.

TABLE 3

Tumor growth rates

| Treatment | Mean tumor vol (mm³) ± SEM | Growth rate (mm³/day) | % Growth inhibition | Delay in tumor growth (days) |
|---|---|---|---|---|
| First protocol | | | | |
| Control-siRNA-C4HD | 516.7 ± 67.1* | 23.1 ± 1.5* | | |
| ErbB-2-siRNA-C4HD | 237.1 ± 50.1# | 11.2 ± 0.9# | 54.1$^a$ | 7$^a$ |
| ErbB-2-siRNA-C4HD-hErbB-2ΔNLS | 218.7 ± 55.5# | 10.2 ± 1.6# | 57.6$^a$ | 7$^a$ |
| Second protocol | | | | |
| C4HD | 491.8 ± 64.0* | 32.1 ± 3.5* | | |
| C4HD-hErbB-2ΔNLS | 123.1 ± 21.8# | 8.5 ± 1.0# | 74.9$^b$ | 6.5$^b$ |

Growth rates were calculated as the slopes of growth curves. In the first protocol, volume and percentage of growth inhibition in tumors from mice injected with ErbB-2-siRNAC4HD or ErbB-2-siRNA-C4HD-hErbB-2ΔNLS cells with respect to mice injected with Control siRNA-C4HD cells were calculated at day 32, as described in Materials and Methods. In the second protocol, comparisons between tumors developed from C4HD hErbB-2ΔNLS and C4HD cells were performed at day 20. # versus *, P<0.001. $^a$ With respect to Control siRNA cells and $^b$ with respect to C4HD cells, for growth inhibition, P<0.001.

Figure 7B:
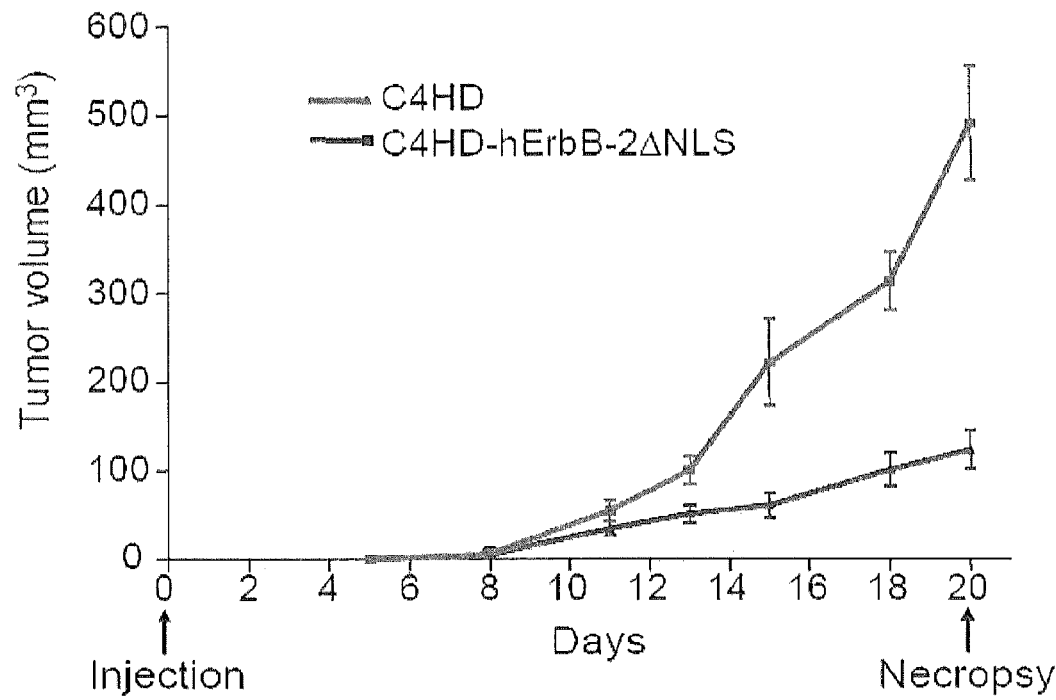
Figure 7C:
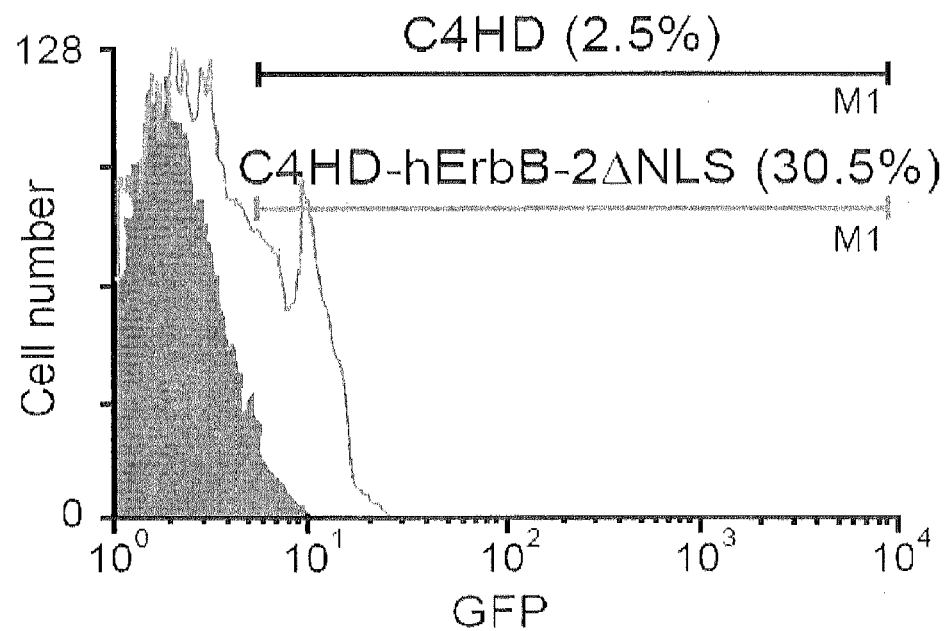
Figure 7C:
Figure 7C:
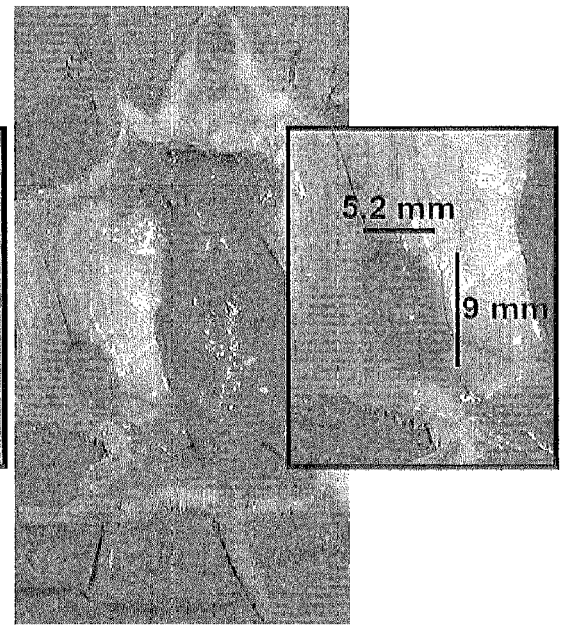
Figure 7D:
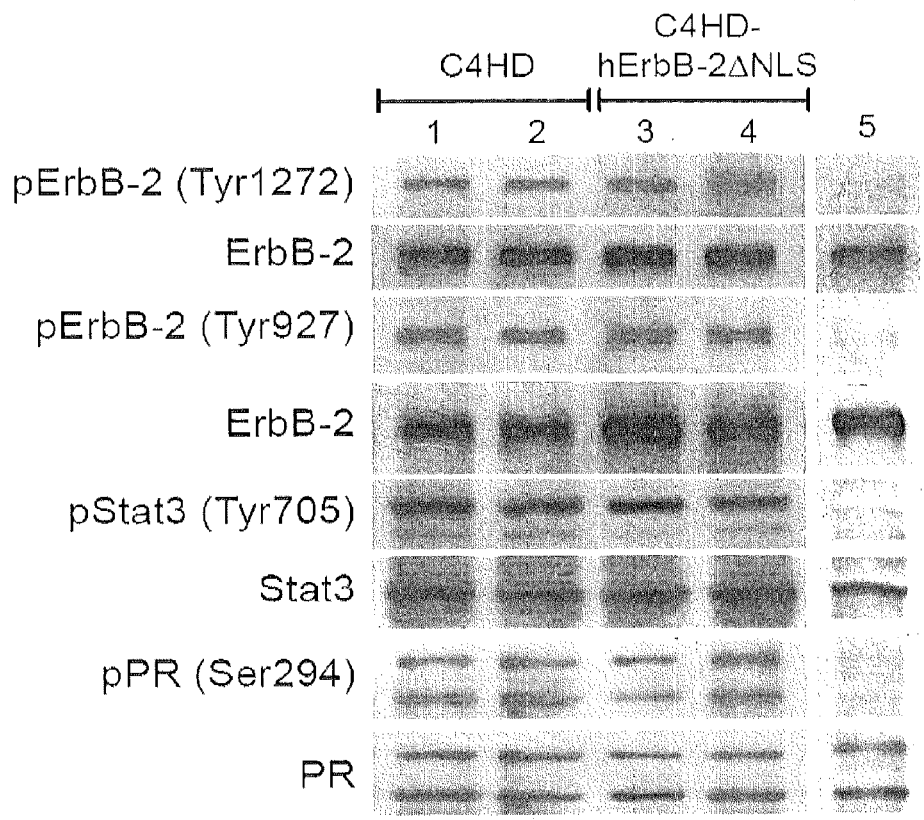
Figure 7E:
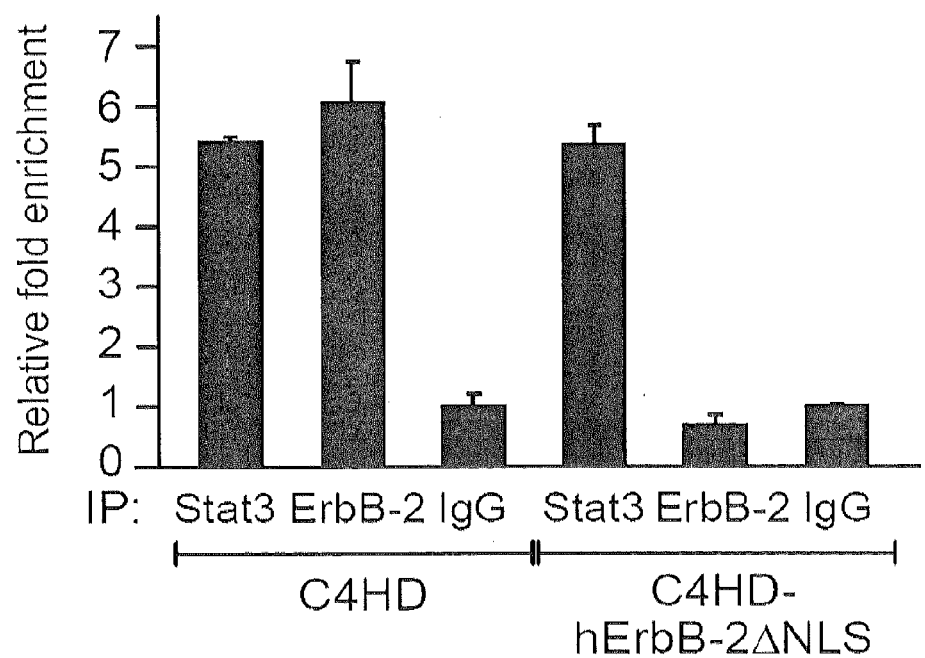

We then used a second experimental protocol in which we addressed whether transfection of hErbB-2ΔNLS to C4HD cells maintaining the expression of endogenous ErbB-2 could modulate the in vivo proliferative response to MPA. For this purpose, C4HD cells were transiently transfected with the hErbB-2ΔNLS vector (C4HD-hErbB-2ΔNLS) or with the empty pcDNA 3.1 vector (C4HD) and cells from each experimental group were inoculated s.c. in mice treated with MPA. We are here showing the results of a representative experiment of a total of four. All mice (n=6) injected with the C4HD-hErbB-2ΔNLS cells and with C4HD cells developed tumors that became palpable after 5 days' inoculation. As seen in FIG. 7B, expression of the hErbB-2ΔNLS in C4HD cells strongly inhibited MPA-induced proliferation. Mean volume (FIG. 7B, and Table 3) and growth rates (Table 3) of tumors developed from C4HD-hErbB-2ΔNLS cells were significantly lower than those of tumors from the control group. Tumors were excised at day 32 in the first protocol and at day 20 in the second and Results are summarized in Table 3. Histopathological analysis revealed that tumors from mice receiving ErbB-2-siRNA-C4HD, ErbB-2-siRNA-C4HD-hErbB-2ΔNLS or C4HD-hErbB-2ΔNLS cells showed significantly lower histological grade (II), with 3-4 mitosis per 10 HPF, as compared to tumors from animals receiving Control-siRNA-C4HD or C4HD cells, both of which showed histological grade III with over 10 mitoses per 10 HPF. The experimental strategies used here relied on transient transfections with the hErbB-2ΔNLS expression vector. Therefore, we explored its intratumoral expression at the end of the experiments. We choose to study samples of the second protocol because of the far-reaching implications of the use of hErbB-2ΔNLS as a single-agent therapy. Since hErbB-2ΔNLS is GFP-tagged, we analyzed its content by flow cytometry. FIG. 7C shows that at day 20 approximately 30% of the cells still expressed the hErbB-2ΔNLS mutant. Next, we examined the state of activation of ErbB-2, Stat3 and PR in the tumor samples. Comparable ErbB-2 and Stat3 phosphorylation levels were found in tumors developed in mice injected with C4HD-hErbB- 2ΔNLS and C4HD cells (FIG. 7 D)). Similar levels of PR phosphorylation at Ser294, which directly correlates with PR transcriptional activity (24), were present in tumors developed from C4HD-hErbB-2ΔNLS and C4HD cells. ChIP analysis demonstrated comparable levels of Stat3 recruitment to the cyclin D1 promoter in tumors arising from C4HD-hErbB-2ΔNLS and C4HD cells (FIG. 7E). On the contrary, we did not find ErbB-2 recruitment to the cyclin D1 promoter in C4HD-hErbB-2ΔNLS cells (FIG. 7E). These results further support the direct involvement of the nuclear Stat3/ErbB-2 transcriptional complex in in vivo growth of breast tumors expressing both PR and ErbB-2.

Discussion

Our present findings in breast cancer cells demonstrate that a steroid hormone receptor, PR, induces ErbB-2 nuclear translocation, its colocalization and physical association with Stat3 at the nuclear compartment, and the assembly of a transcriptional complex in which ErbB-2 acts as a coactivator of Stat3. In this newly discovered class of complex, the transcription factor (Stat3) is first phosphorylated at the cytoplasmic level via its coactivator (ErbB-2) function as an upstream effector. Our results also highlight that ErbB-2 function as a Stat3 coactivator drives progestin-induced cyclin D1 promoter activation, a new and unexpected non-classical PR genomic mechanism. The assembly of the nuclear Stat3/ErbB-2 transcriptional complex plays a key role in both in vitro and in vivo progestin-induced breast tumor growth. In addition to ErbB-2, all the ErbB family members have been detected in the nucleus (29). Since ErbBs lack a putative DNA binding domain, it has been proposed that other transcription factors with DNA binding capacity cooperate with ErbBs to regulate gene expression. Although pioneering findings demonstrated that ErbB-2 modulates COX-2 promoter activation functioning as a transcription factor (30), the capacity of ErbB-2 to act as a transcriptional coactivator had so far remained completely unknown. Our series of functional studies in mouse and human breast cancer cells have provided the first evidence that ErbB-2 acts indeed as a transcriptional coactivator of Stat3. As previously shown for constitutively activated ErbB-2 (30), our data now show that PR induces full-length ErbB-2 protein translocation to the nucleus. We also revealed a new feature of ErbB-2 nuclear status, as we identified its specific phosphorylation at Tyr 1222/1272 and 877/927, induced by progestins via c-Src.

The nuclear interaction of EGF-R and Stat3 in the promoter of the inducible nitric oxide synthase (iNOS), containing both EGF-R binding sites (AT-rich sequences, ATRS) and Stat3 response elements, was identified in seminal studies (18). In that work, the nature of EGF-R and Stat3 nuclear interplay was explored by a different strategy than ours here, since it relied on identifying genes containing both ATRS and Stat3 response elements in their promoters. The presence of two clusters of ATRS and Stat3 binding sites was essential for EGF-R regulation of the iNOS promoter (18). This highlights a major difference with respect to the nuclear ErbB-2/Stat3 transcriptional complex function in the cyclin D1 promoter, which we here found requires only Stat3 binding to the GAS sites and ErbB-2 recruitment to said sites in order to act as a Stat3 coactivator. Without being bound to any particular theory, a likely interpretation of this difference is that EGF-R/Stat3 and ErbB-2/Stat3 complexes regulate chromatin targets by distinct mechanisms as a general rule. It may also indicate that the nature of the interaction between ErbBs and Stat3 within intact cells depends on the set of Stat3/ErbBs binding motifs available in the target gene promoter/enhancer regions, as well as on the specific sequences and unique structural features of the DNA neighboring the Stat3/ErbBs binding sites. Consistent with the latter, Stat3 and EGF-R do not associate at the cyclin D1 promoter, the first to be found regulated by nuclear EGF-R (17), and which also contains a cluster of ATRS/Stat3 sites (18).

Our data showed that the nuclear import of Stat3 mediated by MPA occurs independently of ErbB-2 nuclear localization, as reported for Stat3 and EGF-R (18). Comigration of Stat3 and EGF from the cell surface to the perinuclear region via receptor mediated endocytosis has been previously described (3). Our results are consistent with these earlier findings since we here revealed that hErbB-2ΔNLS moves from the cytoplasmic membrane to the perinuclear region in response to MPA, and thus retains the potential capacity to cotransit with Stat3. Interestingly, our findings identified yet another level of the interaction between Stat3 and ErbB-2, showing that the specific entrance of Stat3 to the nucleus, once located in the perinuclear cytoplasm, is not associated to ErbB-2 nuclear translocation.

It has long been acknowledged that progestins, acting through the classical PR, induce cyclin D1 gene expression in breast cancer cells (4,10). However, the contribution of PR rapid signaling and of PR transcriptional mechanisms still remains to be elucidated. Cyclin D1 promoter lacks a canonical PRE, for which this gene has become a model to investigate the mechanisms through which progestin/PR regulate the expression of genes independently of PR binding to PREs. Seminal works have demonstrated that progestin rapid activation of p42/p44 mitogen-activated kinases (MAPKs) and of phosphatidylinositol 3-kinase (PI-3K)/Akt pathways mediate PR regulation of cyclin D1 expression in breast cancer (4,10,23). Another study suggested that progestins induce cyclin D1 promoter activation via PR tethering to the AP-1 transcription factor at an AP-1 binding site encoded in the distal promoter (9). Our data provide completely novel insight into the mechanism of PR induction of cyclin D1 expression in breast tumors, which integrates rapid PR activation of ErbB-2 and Stat3 and a nonclassical PR transcriptional mechanism consisting of the assembly on the cyclin D1 promoter of a nuclear complex in which ErbB-2 acts a coactivator of Stat3.

The molecular mechanisms of ErbB-2 and Stat3 interaction that lead to breast cancer growth remain almost completely unexplored. Most recently, we found that HRG bound ErbB-2 activates Stat3 through the co-option of PR signaling (22). Activated Stat3 in turn acts as a downstream effector of both HRG/ErbB-2 and unliganded PR to induce proliferation of mammary tumors (22). On the other hand, a startling study showed that targeting Stat3 inhibits growth of ErbB-2 overexpressing mammary cancer cells (26). It has also been found that overexpression of ErbB-2 correlates with Stat3 activation and binding to its response elements in the p21Cip 1 promoter, and that this is involved in chemotherapy resistance in breast tumor (13). An exciting and novel finding of our study is its demonstration of a direct correlation between nuclear ErbB-2 function as a Stat3 transcriptional coactivator and breast cancer growth. Indeed, we found that cells expressing the mutant hErbB-2ΔNLS show a strongly reduced response to progestin induced in vitro and in vivo proliferation. Notably, transfection of hErbB-2ΔNLS to C4HD cells expressing endogenous ErbB-2 (C4HD-hErbB-2ΔNLS cells) abrogated their proliferative response to progestins, consistent with our results identifying the role of hErbB-2ΔNLS as a DN inhibitor of wild-type ErbB-2 nuclear translocation. Our molecular studies in tumors from mice injected with C4HD-hErbB-2ΔNLS cells revealed high levels of ErbB-2 and Stat3 tyrosine phosphorylation as well as a significant degree of PR phosphorylation at Ser294, which has been found to directly correlate with PR transcriptional activity (24). We also detected a strong Stat3 binding to the cyclin D1 promoter in tumors arising from C4HD-hErbB-2ΔNLS cells. Most challenging was our finding that ErbB-2 recruitment to the cyclin D1 was completely abrogated in these tumors. These results have far-reaching therapeutic implications since they indicate that growth of breast tumors with intact ErbB-2 tyrosine kinase function and PR transcriptional activity can be abolished by blockage of ErbB-2 nuclear translocation. At present, COX-2 is the only gene whose expression has been shown to be modulated through ErbB-2 role as a transcriptional activator (30). Interestingly, COX-2 inhibition in MCF-7 cells overexpressing ErbB-2 and in the parental MCF-7 cells had no effect on proliferation of the latter but suppressed the invasive activity of the ErbB-2 overexpressing MCF-7 cells (30). Undoubtedly, other yet unidentified genes regulated by ErbB-2 through its role as a transcription factor, may be involved in ErbB-2 proliferative effects. On the other hand, our present results support the exciting notion that ErbB-2 function as a transcriptional coactivator may be the one directly involved in ErbB-2 stimulation of breast cancer growth.

Approximately 50% of human breast cancers that overexpress ErbB-2 also display ER and PR, a phenotype associated with resistance to hormonal therapy, whose clinical management still remains to be established (20). Although clinical data indicate that combined anti-hormonal and anti-ErbB-2 therapies, such as blockage of ErbB-2 with the recombinant humanized anti-ErbB-2 monoclonal antibody trastuzumab (Herceptin), improve outcome as compared to endocrine treatment alone, other studies suggested that this dual strategy might in fact render lower results than those obtained through the combination of trastuzumab with chemotherapy (20). This confronts us with a significant number of patients requiring new therapies for ErbB-2 overexpressing breast tumors. Our present findings provide strong rationale for a potential novel gene therapy intervention in PR- and ErbB-2-positive breast tumors comprising the transfer of hErbB-2ΔNLS.

Materials and Methods
Animals and Tumors

Experiments were carried out with female BALB/c mice raised at the IBYME. Animal studies were conducted as described (21), in accordance with the highest standards of animal care as outlined in the NIH Guide for the Care and Use of Laboratory Animals and were approved by the IBYME Animal Research Committee. C4HD tumor line displays high levels of estrogen receptor (ER) and PR, overexpresses ErbB-2 and ErbB-3, exhibits low ErbB-4 levels and lacks EGF-R expression (2). This tumor line expresses neither glucocorticoid receptor (GR) nor androgen receptor (AR) (2).

Reagents

Medroxyprogesterone acetate (MPA) and RU486 were purchased from Sigma-Aldrich (San Louis, Mich.). 4-Amino-5-(4-chlorophenyl)-7-(t-butyl)pyrazolo[3,4-d]pyrimidine (PP2), Tyrphostin AG825, and Jak inhibitor I were purchased from Calbiochem (San Diego, Calif.).

Antibodies

The following antibodies were used for Western blots: phospho-Stat3 (Tyr705) (B-7), total Stat3 (C-20), phospho-Jak1 (Tyr1022/1023), total Jak1 (HR-785), total Jak2 (C-20), ErbB-2 (C-18, raised against the C-terminus), ErbB-2 (9G6, raised against the N-terminus), and phospho-tyrosine (PY99), all from Santa Cruz Biotechnology (Santa Cruz, Calif.); phospho-ErbB2 (Tyr 1221/1222), phospho-ErbB2 (Tyr877), phospho-Jak2 (Tyr1007/1008), c-Src, and phospho-Src (Tyr416), from Cell Signaling (Beverly, Mass.); cyclin D1, PR (clone hPRa7), and actin (clone ACTN05), from Neomarkers (Freemont, Calif.); β tubulin from Sigma-Aldrich; histone H3 from Abcam (Cambridge, Mass.); phospho-PR (Ser294) from Affinity BioReagents (Rockford, Ill.) and HRP-conjugated secondary antibody from Vector Laboratories (Burlingame, Calif.). The antibodies used for immunoprecipitation experiments, chromatin immunoprecipitation (ChIP), and sequential ChIP assays were the rabbit polyclonal anti-ErbB-2 and anti-Stat3 antibodies (C-18 and C-20, respectively, from Santa Cruz Biotechnology) and rabbit IgG (Sigma-Aldrich) was used as negative control.

Cell Cultures, Treatments, and Proliferation Assays

Primary cultures of epithelial cells from C4HD tumors were performed as described (2). T47D cells were obtained from American Type Culture Collection and T47D-Y cells were a generous gift from Dr. K. Horwitz (Denver, Colo.). To evaluate the effects of the pharmacological inhibitors on MPA-induced proteins phosphorylation or cyclin D1 expression, cells were preincubated for 90 min with RU486, PP2, Tyrphostin AG825 or Jak inhibitor I before addition of MPA. Cell proliferation was evaluated by [3H]-thymidine incorporation assay and cell cycle distribution was analyzed by flow cytometry, as described (22).

Western Blots and Immunoprecipitations

Lysates were prepared from cells subjected to the different treatments and proteins were subjected to SDS-PAGE as previously described (21). Membranes were immunoblotted with the antibodies detailed in each experiment. When phospho(p)-protein antibodies were used, filters were reprobed with total protein antibodies. Signal intensities of pErbB-2, pStat3, pSrc, pPR, pJak1, and pJak2 bands were analyzed by densitometry and normalized to total protein bands. Similarly, signal intensities of PR, cyclin D1, Stat3, and ErbB-2 bands were normalized to actin or β tubulin bands. Data analysis showed a significant increase in pErbB-2, pStat3, and pSrc levels by MPA treatment as compared to nontreated cells, and a significant inhibition of MPA-induced proteins phosphorylation when the pharmacological inhibitors of ErbB-2 and Stat3 or PR and ErbB-2 siRNAs were used ($P<0.001$). Similar data analysis showed that increase in cyclin D1 levels by MPA treatment from 12 to 72 h, as compared to control cells, was significant as well as inhibition of MPA effects by ErbB-2 and Stat3 inhibitors and siRNAs ($P<0.001$). The NEPER Nuclear and Cytoplasmic Extraction Reagents technique (Pierce Biotechnology) was performed as per manufacturer's instructions. Nuclear association between ErbB-2 and Stat3 was studied by performing coimmunoprecipitation experiments using 200 μg of nuclear protein lysates as described (22).

Plasmids and Transient Transfections

The luciferase reporter plasmid downstream the cyclin D1 human promoter region (−1745 cyclin D1-luc), and constructs truncated at positions −963, −261, −141, were kindly provided by Dr. R. Pestell (Northwestern University Medical School, Chicago, Ill.). These constructs were generated by truncation of the 1745-bp length promoter in order to sequentially exclude 5′ regions of the promoter. The −963 cyclin D1-luc construct excludes one GAS site (−984), the −261 cyclin D1-luc excludes three GAS sites (−984, −568 and −475) and the −141 cyclin D1-luc excludes four GAS sites (−984, −568, −475 and −239). The empty vector pA3 Luc was also provided by Dr. R. Pestell. The luciferase reporter plasmid containing four copies of the m67 high-affinity binding site (p4×m67-tk-luc) and the pTATA-tk-Luc reporter lacking the m67 insertion were a gift from Dr J. Darnell (The Rockefeller University, New York, N.Y.). The *Renilla* luciferase expression plasmid RLCMV was obtained from Promega (Madison, Wis.). Dominant negative Stat3 expression vector, Stat3Y705-F, which carries a tyrosine to phenylalanine substitution at codon 705 that reduces phosphorylation on tyrosine of the wild-type Stat3 protein, therefore inhibiting both dimerization and DNA binding of Stat3 (6,7,16) was kindly provided by Dr J. Darnell (New York, USA). The empty pcDNA3.1 vector was also a gift of Dr J. Darnell. Human wild-type ErbB-2 expression vector (hErbB-2WT) as well as the empty pMe18SM vector were a gift from by Dr. T. Yamamoto (University of Tokyo, Japan) (1). The GFP-tagged human ErbB-2 mutant which lacks the putative nuclear localization signal sequence (aa 676-KRRQQKIRKYTMRR-689) (SEQ ID NO:3), resulting in the sequence of KLM at the deletion junction (hErbB-2ΔNLS), was generously provided by Dr. M. C. Hung (The University of Texas M.D. Anderson Cancer Center, Houston, Tex.) (Giri et al., 2005). The empty pEGFP-N1 vector was obtained from BD Biosciences Clontech (Palo Alto, Calif.). The plasmid encoding the human wild-type hPR-B was kindly provided by Dr. K. Horwitz. In experiments assessing MPA capacity to induce the transcriptional activation of Stat3, C4HD and T47D cells were transiently transfected for 48 h with 1 μg of −1745 cyclin D1-luc reporter plasmid or the truncated −963, −261 and −141 constructs, or with 1 μg p4×m67-tk-luc and 10 ng of RL-CMV used to correct variations in transfection efficiency. As control, cells were transfected with 1 μg of either the pA3 Luc or pTATA-tk-Luc reporters. Cells were cotransfected with 2 μg of Stat3Y705-F when indicated. Total amount of transfected DNA was standardized by adding the empty pcDNA3.1 vector. In experiments assessing the role of ErbB-2 in Stat3 transcriptional activation, cells were cotransfected with 2 μg of hErbB-2WT, hErbB-2ΔNLS or the empty vectors pMe18SM and pEGFP-N1. When these vectors were cotransfected with p4×m67-tk-luc, 400 ng were added instead of 2 μg. Cells were then starved for 24 h and treated with MPA during 24 h, or were left untreated. The Fugene 6 transfection reagent technique (Roche Biochemicals) was performed as described (22). Transfection efficiencies, evaluated using the pEGFP-N1 vector and determined by the percentage of cells that exhibited GFP 4 days after transfection, varied between 60-70%. Transfected cells were lysed and luciferase assays were carried out using the Dual-Luciferase Reporter Assay System (Promega) in accordance with manufacturer's instructions. Triplicate samples were analyzed for each datum point. Differences between experimental groups were analyzed by ANOVA followed by Tukey test between groups.

siRNA Transfections siRNAs targeting ErbB-2, Stat3, and Pr were synthesized by Dharmacon, Inc (Lafayatte, Colo.) (ErbB-2siRNA: 5'GAUGGUGCUUACUCAUUGA3' (SEQ ID NO:8), designed to specifically knockdown mouse ErbB2 but not human ErbB-2; Stat3siRNA: 5'GGUCAAAUUUC-CUGAGUUGUU3' (SEQ ID NO:9) targets mouse Stat3; and 5'GAGCAGAGAUGUGGGAAUGUU3' (SEQ ID NO:10) targets human Stat3; PRsiRNA: 5'AUAGGCGA-GACUACAGACGUU3'(SEQ ID NO:11)). A nonsilencing siRNA oligonucleotide from Dharmacom which does not target any known mammalian gene was used as a negative control. Transfection of siRNAs duplexes was performed by using the DharmaFECT transfection reagent following the manufacturer's direction for 3 days. For reconstitution experiments cotransfection of 25 nM ErbB-2 siRNA with 2 μg expression vectors was performed using DharmaFECT Duo transfection reagent (Dharmacon).

Immunofluorescence and Confocal Microscopy

Cells grown on glass coverslips were fixed and permeabilized in ice-cold methanol and were then blocked with PBS 1% BSA. ErbB-2 was localized using either a rabbit polyclonal (C-18) or a mouse monoclonal (F-11) ErbB-2 antibody (Santa Cruz Biotechnology) and Stat3 was detected using a mouse monoclonal antibody (124H6, Cell Signaling), followed by incubation with a goat anti-rabbit IgG-Alexa 488 (Molecular Probes, Eugene, Oreg.) secondary antibody for ErbB-2 (C-18) and with a rhodamine conjugated goat anti-mouse secondary antibody (Jackson ImmunoResearch Laboratories, West Grove, Pa.) for both ErbB2 (F-11) and Stat3. Negative controls were carried out using PBS instead of primary antibodies, or 5× competitive peptide (Santa Cruz Biotechnology) when ErbB-2 (C-18) was used. When cells were transfected with hErbB-2ΔNLS, green fluorescent protein from this expression vector was visualized by direct fluorescence imaging. Approximately 100-200 cells were analyzed for each treatment, out of which around 80% showed the same pattern of Stat3 and ErbB-2 cellular localization. FIGS. 2A, 3B and C, illustrate a few cells representative of the ones examined. Cells were analyzed using a Nikon Eclipse E800 confocal laser microscopy system (22).

ChIP and Sequential ChIP Assays

ChIP was performed as described elsewhere (Hawthorne et al., 2005) with minor modifications. Briefly, chromatin was sonicated to an average of about 500 bp. Sonicated chromatin was then immunoprecipitated using 4 μg of either an anti-ErbB-2 or an anti-Stat3 antibody and rabbit IgG as control. The IP was collected using Protein A beads (Upstate Biotechnology, Lake Placid, N.Y.), which were washed repeatedly to remove nonspecific DNA binding. The chromatin was eluted from the beads and crosslinks were removed overnight at 65° C. DNA was then purified and quantified using real-time PCR. For sequential ChIP experiments, Stat3 immunoprecipitates were eluted with DTT and then subjected to a second round of immunoprecipitation with ErbB-2 antibody or with IgG.

Real-Time Quantitative PCR

ChIP DNA was amplified by real-time PCR (qPCR), performed with an ABI Prism 7500 sequence detector using SYBR green PCR master mix (Applied Biosystems, Foster City, Calif.). The primers used were as follows: 5'-TTCCG-GTGGTCTGGTTCCT-3' (SEQ ID NO:12) and 5'-GAGA-CACGATAGGCTCCTTCCTAA-3'(SEQ ID NO:13) designed to amplify a region of the mouse cyclin D1 promoter containing two GAS sites (−971 and −874), 5'-GGAACCTTCGGTGGTCTTGTC-3'(SEQ ID NO:14) and 5'-GAATGGAAAGCTGAGAAACAGTGA-3' (SEQ ID NO:15) designed to amplify a region of the human cyclin D1 promoter containing one GAS site (−984). These primers were designed with "Primer Express" real-time PCR primer design software (Applied Biosystems). PCR was performed for 40 cycles with 15s of denaturing at 95° C. and annealing and extension at 60° C. for 1 min.

In Vivo Inhibition of ErbB-2 Nuclear Localization

C4HD cells were transiently transfected with the siRNAs and expression vectors detailed under Results. After transfection, 106 cells from each experimental group were inoculated s.c. into animals treated with a 40-mg MPA depot in the flank opposite to the cell inoculum. Tumor volume, growth rate, and growth delay were determined as previously described (21). Comparison of tumor volumes between the different groups for specific times was done by analysis of variance followed by Tukey's t test among groups. Linear regression analysis was performed on tumor growth curves, and the slopes were compared using analysis of variance followed by a parallelism test to evaluate the statistical significance of differences.

REFERENCES

1. Akiyama, T., S. Matsuda, Y. Namba, T. Saito, K. Toyoshima, and T. Yamamoto. 1991. The transforming potential of the c-erbB-2 protein is regulated by its autophosphorylation at the carboxyl-terminal domain. Mol. Cell Biol. 11:833-842.

2. Balana, M. E., R. Lupu, L. Labriola, E. H. Charreau, and P. V. Elizalde. 1999. Interactions between progestins and heregulin (HRG) signaling pathways: HRG acts as mediator of progestins proliferative effects in mouse mammary adenocarcinomas. Oncogene 18:6370-6379.

3. Bild, A. H., J. Turkson, and R. Jove. 2002. Cytoplasmic transport of Stat3 by receptor-mediated endocytosis. EMBO J. 21:3255-3263.

4. Boonyaratanakornkit, V., E. McGowan, L. Sherman, M. A. Mancini, B. J. Cheskis, and D. P. Edwards. 2007. The role of extranuclear signaling actions of progesterone receptor in mediating progesterone regulation of gene expression and the cell cycle. Mol. Endocrinol. 21:359-375.

5. Boonyaratanakornkit, V., M. P. Scott, V. Ribon, L. Sherman, S. M. Anderson, J. L. Maller, W. T. Miller, and D. P. Edwards. 2001. Progesterone receptor contains a proline-rich motif that directly interacts with SH3 domains and activates c-Src family tyrosine kinases. Mol. Cell 8:269-280.

6. Bromberg, J. F., C. M. Horvath, D. Besser, W. W. Lathem, and J. E. Darnell, Jr. 1998. Stat3 activation is required for cellular transformation by v-src. Mol. Cell Biol. 18:2553-2558.

7. Bromberg, J. F., M. H. Wrzeszczynska, G. Devgan, Y. Zhao, R. G. Pestell, C. Albanese, and J. E. Darnell, Jr. 1999. Stat3 as an oncogene. Cell 98:295-303.

8. Casimiro, M., O. Rodriguez, L. Pootrakul, M. Aventian, N. Lushina, C. Cromelin, G. Ferzli, K. Johnson, S. Fricke, F. Diba, B. Kallakury, C. Ohanyerenwa, M. Chen, M. Ostrowski, M. C. Hung, S. A. Rabbani, R. Datar, R. Cote, R. Pestell, and C. Albanese. 2007. ErbB-2 induces the cyclin D1 gene in prostate epithelial cells in vitro and in vivo. Cancer Res. 67:4364-4372.

9. Cicatiello, L., R. Addeo, A. Sasso, L. Altucci, V. B. Petrizzi, R. Borgo, M. Cancemi, S. Caporali, S. Caristi, C. Scafoglio, D. Teti, F. Bresciani, B. Perillo, and A. Weisz. 2004. Estrogens and progesterone promote persistent CCND1 gene activation during G1 by inducing transcriptional derepression via c-Jun/c-Fos/estrogen receptor (progesterone receptor) complex assembly to a distal regulatory element and recruitment of cyclin D1 to its own gene promoter. Mol. Cell Biol. 24:7260-7274.

10. Faivre, E., A. Skildum, L. Pierson-Mullany, and C. A. Lange. 2005. Integration of progesterone receptor mediated rapid signaling and nuclear actions in breast cancer cell models: role of mitogen-activated protein kinases and cell cycle regulators. Steroids 70:418-426.

11. Giri, D. K., M. Ali-Seyed, L. Y. Li, D. F. Lee, P. Ling, G. Bartholomeusz, S. C. Wang, and M. C. Hung. 2005. Endosomal transport of ErbB-2: mechanism for nuclear entry of the cell surface receptor. Mol. Cell Biol. 25:11005-11018.

12. Guo, W., Y. Pylayeva, A. Pepe, T. Yoshioka, W. J. Muller, G. Inghirami, and F. G. Giancotti. 2006. Beta 4 integrin amplifies ErbB2 signaling to promote mammary tumorigenesis. Cell 126:489-502.

13. Hawthorne, V. S., W. C. Huang, C. L. Neal, L. M. Tseng, M. C. Hung, and D. Yu. 2009. ErbB2-mediated Src and signal transducer and activator of transcription 3 activation leads to transcriptional up-regulation of p21Cip1 and chemoresistance in breast cancer cells. Mol. Cancer Res. 7:592-600.

14. Labriola, L., M. Salatino, C. J. Proietti, A. Pecci, O. A. Coso, A. R. Kornblihtt, E. H. Charreau, and P. V. Elizalde. 2003. Heregulin induces transcriptional activation of the progesterone receptor by a mechanism that requires functional ErbB-2 and mitogen-activated protein kinase activation in breast cancer cells. Mol. Cell Biol. 23:1095-1111.

15. Leslie, K., C. Lang, G. Devgan, J. Azare, M. Berishaj, W. Gerald, Y. B. Kim, K. Paz, J. E. Darnell, C. Albanese, T. Sakamaki, R. Pestell, and J. Bromberg. 2006. Cyclin D1 is transcriptionally regulated by and required for transformation by activated signal transducer and activator of transcription 3. Cancer Res. 66:2544-2552.

16. Li, L. and P. E. Shaw. 2002. Autocrine-mediated activation of STAT3 correlates with cell proliferation in breast carcinoma lines. J. Biol. Chem. 277:17397-17405.

17. Lin, S. Y., K. Makino, W. Xia, A. Matin, Y. Wen, K. Y. Kwong, L. Bourguignon, and M. C. Hung. 2001. Nuclear localization of EGF receptor and its potential new role as a transcription factor. Nat. Cell Biol. 3:802-808.

18. Lo, H. W., S. C. Hsu, M. Ali-Seyed, M. Gunduz, W. Xia, Y. Wei, G. Bartholomeusz, J. Y. Shih, and M. C. Hung. 2005. Nuclear interaction of EGFR and STAT3 in the activation of the iNOS/NO pathway. Cancer Cell 7:575-589.

19. Migliaccio, A., D. Piccolo, G. Castoria, M. Di Domenico, A. Bilancio, M. Lombardi, W. Gong, M. Beato, and F. Auricchio. 1998. Activation of the Src/p21ras/Erk pathway by progesterone receptor via cross-talk with estrogen receptor. EMBO J. 17:2008-2018.

20. Prat, A. and J. Baselga. 2008. The role of hormonal therapy in the management of hormonal-receptor-positive breast cancer with co-expression of HER2. Nat. Clin. Pract. Oncol. 5:531-542.

21. Proietti, C., M. Salatino, C. Rosemblit, R. Carnevale, A. Pecci, A. R. Kornblihtt, A. A. Molinolo, I. Frahm, E. H. Charreau, R. Schillaci, and P. V. Elizalde. 2005. Progestins induce transcriptional activation of signal transducer and activator of transcription 3 (Stat3) via a Jak- and Src-dependent mechanism in breast cancer cells. Mol. Cell Biol. 25:4826-4840.

22. Proietti, C. J., C. Rosemblit, W. Beguelin, M. A. Rivas, M. C. Diaz Flaque, E. H. Charreau, R. Schillaci, and P. V. Elizalde. 2009. Activation of Stat3 by heregulin/ErbB-2 through the co-option of progesterone receptor signaling drives breast cancer growth. Mol. Cell Biol. 29:1249-1265.

23. Saitoh, M., M. Ohmichi, K. Takahashi, J. Kawagoe, T. Ohta, M. Doshida, T. Takahashi, H. Igarashi, A. Mori-Abe, B. Du, S. Tsutsumi, and H. Kurachi. 2005. Medroxyprogesterone acetate induces cell proliferation through up-regulation of cyclin D1 expression via phosphatidylinositol 3-kinase/Akt/nuclear factor-kappaB cascade in human breast cancer cells. Endocrinology 146:4917-4925.

24. Shen, T., K. B. Horwitz, and C. A. Lange. 2001. Transcriptional hyperactivity of human progesterone receptors is coupled to their ligand-dependent down-regulation by mitogen-activated protein kinase-dependent phosphorylation of serine 294. Mol. Cell Biol. 21:6122-6131.

25. Sutherland, R. L. and E. A. Musgrove. 2004. Cyclins and breast cancer. J. Mammary. Gland. Biol. Neoplasia. 9:95-104.

26. Tan, M., K. H. Lan, J. Yao, C. H. Lu, M. Sun, C. L. Neal, J. Lu, and D. Yu. 2006. Selective inhibition of ErbB2-overexpressing breast cancer in vivo by a novel TATbased ErbB2-targeting signal transducers and activators of transcription 3-blocking peptide. Cancer Res. 66:3764-3772.

27. Tsai, M. J. and B. W. O'Malley. 1994. Molecular mechanisms of action of steroid/thyroid receptor superfamily members. Annu. Rev. Biochem. 63:451-486.

28. Tzahar, E., H. Waterman, X. Chen, G. Levkowitz, D. Karunagaran, S. Lavi, B. J. Ratzkin, and Y. Yarden. 1996. A hierarchical network of interceptor interactions determines signal transduction by Neu differentiation factor/neuregulin and epidermal growth factor. Mol. Cell Biol. 16:5276-5287.

29. Wang, S. C. and M. C. Hung. 2009. Nuclear translocation of the epidermal growth factor receptor family membrane tyrosine kinase receptors. Clin. Cancer Res. 15:6484-6489.

30. Wang, S. C., H. C. Lien, W. Xia, I. F. Chen, H. W. Lo, Z. Wang, M. Ali-Seyed, D. F. Lee, G. Bartholomeusz, F. Ou-Yang, D. K. Giri, and M. C. Hung. 2004. Binding at and transactivation of the COX-2 promoter by nuclear tyrosine kinase receptor ErbB-2. Cancer Cell 6:251-261.

31. Xu, W., X. Yuan, K. Beebe, Z. Xiang, and L. Neckers. 2007. Loss of Hsp90 association up-regulates Src-dependent ErbB2 activity. Mol. Cell Biol. 27:220-228.

The foregoing is illustrative of the present invention, and is not to be construed as limiting thereof. The invention is defined by the following claims, with equivalents of the claims to be included therein. All publications, patent applications, patents, patent publications, sequences identified by GenBank and/or protein accession numbers, and other references cited herein are incorporated by reference in their entireties for the teachings relevant to the sentence and/or paragraph in which the reference is presented.

That which is claimed is:

1. A method of treating breast cancer in a subject, comprising delivering to a subject in need of such treatment a nucleic acid sequence encoding a mutant ErbB-2 polypeptide in an amount effective to inhibit cancer cell proliferation, wherein the mutant lacks a functional nuclear localization signal, cannot translocate to the nucleus of the cell in which it is present, and functions as a dominant-negative inhibitor of endogenous ErbB-2 by inhibiting nuclear translocation of endogenous ErbB-2 in the cell in which the mutant is present, wherein the cancer overexpresses ErbB-2, and the mutant ErbB-2 polypeptide retains intrinsic tyrosine kinase activity and does not inhibit endogenous ErbB-2 tyrosine kinase activity.

2. The method of claim 1, wherein the cancer is estrogen receptor positive.

3. The method of claim 1, wherein the nuclear localization signal is deleted.

4. The method of claim 1, wherein the mutant inhibits progestin induced cancer cell proliferation.

5. The method of claim 1, wherein the mutant inhibits progesterone receptor inducement of endogenous ErbB-2.

6. The method of claim 1, wherein the cancer is resistant to at least one ErbB-2 targeting therapy selected from the group consisting of trastuzumab, lapatinib, and pertuzumab.

7. The method of claim 1, wherein the cancer is resistant to at least one hormonal therapy selected from the group consisting of tamoxifen and anastrozole.

8. The method of claim 1, wherein the mutant of ErbB-2 is delivered as a single-agent therapy.

9. The method of claim 1, wherein the mutant of ErbB-2 is delivered in combination with at least one additional cancer therapy.

10. The method of claim 9, wherein the at least one additional cancer therapy is an ErbB-2 targeting therapy selected from the group consisting of trastuzumab, lapatinib, and pertuzumab.

11. The method of claim 9, wherein the at least one additional cancer therapy is a hormonal therapy selected from the group consisting of tamoxifen and anastrozole.

12. The method of claim 1, wherein the mutant of ErbB-2 is delivered to the subject as a nucleic acid sequence that encodes the mutant and expresses the mutant in the subject.

13. The method of claim 1, wherein the mutant of ErbB-2 is delivered to the subject by injection.

14. The method of claim 1, wherein the mutant of ErbB-2 is delivered to the subject by liposome-mediated transfection.

15. The method of claim 1, wherein the mutant does not comprise a nuclear localization signal sequence of SEQ ID NO:3.

16. The method of claim 1, wherein the cell retains endogenous ErbB-2 expression.

* * * * *

SEQUENCE LISTING

<160> NUMBER OF SEQ ID NOS: 15

<210> SEQ ID NO 1
<211> LENGTH: 40523
<212> TYPE: DNA
<213> ORGANISM: Homo sapiens

<400> SEQUENCE: 1

```
agttcccgga tttttgtggg cgcctgcccc gcccctcgtc ccctgctgt gtccatatat      60 cgaggcgata gggttaaggg aaggcggacg cctgatgggt taatgagcaa actgaagtgt    120
tttccatgat ctttttgag gtagggctgt ttactgtcac caccctgtc ggattttact     180 tcctaaacgt acctgtaact atccacttct ctccatctct tctggcacca ccctggttaa    240
agacaccatc atgtgtcgcc aagacagccg cagtagcttc ttaatggctc tccctgcctc    300
tacttttgcc tcttccaacc tgcgctccat tttgaaaaat taaaatttgc ccatatcact    360
ttttttttct taaaattatt tactggctcc caattacctt gggtaaaata cagtctccac    420
aaaccctgcc tgatttggcc cctgtccact ggtctccctc actcccttgc tccagacccg    480
cttcagaggg ctatgtccct caagcttcct gactgcctgg cctggtctga atcactcact    540 cttcttttt cttctagtcg caattgaagt accacctccc gagggtgatt gcttcccat     600 gcggggtaga acctttgctg tcctgttcac cactctacct ccagcacaga atttggctta    660
tggtaggcgc taactgcgtt tgtttgttct tctgtttaat gaatgaacag catacatcaa    720
cataagaact tgacaaatcc agggctgtaa aatcatcagt atggttctgc actgagatcg    780
gagagaagta atatttctag gaaaattagg aaccctggga acaggacgct tgctttagta    840
tcctctccct gctcacctcc cctgcactcc catcagcacc gacccacacc caatctcata    900
gaagccttgt agctaaggat cacccttttct cctccccac tctcctcacc ccttgtcaac    960 ttttctttt cgtcctgggg gttggaatga gtaagaagta gcctgggatt ccattcactc   1020
acttaacaaa catttctgag tccttagctc tagcaccttg ctaagcaagg caaaatctcc   1080
aggaggcacc attcacattg cattttctgt gaatggtgct ctggggagca gcattcacat   1140
tgccttttct gtgaatggca aattcttcca gttaaatata acatgaatag tgtcccctgg   1200
agttgaccac ccaactgata ctgactgaga agctgaaatg aacaaaacaa ccccttagcc   1260
ctccaggagc tgaccggaaa tccagtgcta atactacttt gcatcttaca gattagttct   1320
tttacaatac tgttttttt tcttttttca tttcattttg tcctttctgt gactctggga   1380
tgagtctttt tatgaggatc ctcatataaa gatggacatt taggattaaa gaggatgaaa   1440
```

```
tcctgacaaa ataggggagtc tcccctttag aaaattccta agtaaggctg ggggtggtgg      1500
ctcacgcctg taatcccagc actttgggag gccgaggcgg acggatcacc tgaggttagg      1560
agtttgagac cagcctgacc aacatggaga accccatct ctactaaaaa tacaaaatta       1620
gttgggtgtg gtggtgcatg cctgtaatcc cagctactca ggaggctgag gcaggagaat      1680
cgcttgaacc cagggaggca gaggttgtgg tgagccaaga ttgcgccatc gcactccagc      1740
ctgggcaaca agagcgaaac tcaaaaaaaa aaaaaaaag aaaagaaaa ttccaatttt        1800 gaaggcctca tcctatatta tgtcaaacat actgaaatgc agtaacgccc cacattaaat      1860
aagatttata ataactata catatatata attcaatcta attgctgtta atagttgaca       1920
tattgctaca tttatataca tttagttaaa aaaaattttt tttcccagac agcctctcac      1980
tctttcacct agactgaagt gcagtggcat gatcacgact cactgcaacc tcaacctccc      2040
agactcaagt gatccttcca tctcagcctc ctgagtagct gggactgcag catgcgccac      2100
tatgccctgc taattttttt aatttttgt agagacacgg tcttgctatg ttgcctagac       2160
tggtctccaa ttcctgggct cgagtgatcc tcccgcctca acctcccaaa gtgctgggat      2220
tacgggcgtg agccatgcca cacggccata aatattaat tttcgcagct ttcttatatt       2280
ttagaactaa caatgaaat ttgttcgggt ctaaagtatt tcagaggtcc ttgaaaaccc       2340
atgcctacat acctgatgga aaaagcaatc ctaggttaat ggtggaagtg ggagtagaga      2400
cttctgttct gttgacttct tggaagatgg ggtactgtct ctctgggaca gctcttgaga      2460
atttccctgc cagcacagcc ccagataaca atctctagat ggcgattacc tggcctctct      2520
tcccaacttt ctagcctgga gccccctagtt ctccctgag cctccttagc ttgtccttct      2580
tcctaacttg tatttggctt cagatgtgat ccacagtctg aaaagtcact aattcattcc      2640
ttcaactcag gcttattgag tcctcctgtg tatcagccat tgtactcatg ggggaaaaaa     2700
aagacaaagc atatgttaat agtagagtgt gctggacagg cacagtggct catgcctgta      2760
atcccagcac tttgggaggg cgaggcaggt ggatcatctg aggtcaggag ttcgagacca      2820
gcctgaccta acatggagaa actcctgaga tcgtgccatt gcactccagc ctgggcaaca      2880
agagcaaaac tccgtttcaa aaaaaaaaa aaagtatag tgtgctaaag gctcaacggc         2940
aagctgacca tgttcttaga tcaaaattgg tagagagtct acaatgtggg ttccttattc      3000
atcaaatgtt tattaagttt accatgtgca agtctctggg aacagagtga tgaacaaggc      3060
actgtacttt tcatggtcag aggagggaaa caggccataa acaagtgtca aacaaaagac      3120
tgaagccagg tgcggtggct cacatctgta atcccagcac tgtgggaggc caaggcaggc      3180
ggatcatgag atcaggagat cgagaccatc ctagccaaca tggtgaaacc ccatctctac      3240
taaaaataca aaaaattag ctgggcatgg tggcacgtgc ctgtaatccc agctactccg       3300
gaagctgagg caggagaatt gcttgaacca gggagttgga ggttgcagtg agcctggatt      3360
atgccactgc actccagcct ggtgacagag cgagactcca tctacattaa aaaaaaaat      3420 atatatat atatatacac acacacacac acacacacac acatacccctc taacccagga      3480 atttcactcc taggtatacc tacataagct ccagtatacc taaacaagtg caaatttgtt      3540
taagtacagt tatttgtggt agcattagtc attgttttca atgcaagaa gaaaaaggaa      3600 acaactaaat gtccatcaat agggaatgaa ttatattaat ggagggagag ccatacaatg      3660
gaaggctgaa cagaaattaa taggaatggg gcagatttgt aatgtactag catggtaaaa     3720
ccttcatgat agatatagat atagatatag atatagatat agatatatat acatatacat      3780
atacatatac atatacatat atatatatat atatatatat ctcttgtgtc tcagcctccc      3840
```

```
gagtagctgg gattacaggt gtgtgccacc acatccggct aattttttgta ttttttagta    3900 gagacagggc ttcaccatgt tggtaaggct gtcttgaact cccgacctca ggtgatccac    3960
ctgtctcagc ctcccaaagt gctgggatta taggcatgag ccatcacacc tggccaaata    4020
tttttgataa gtatcaagtg cacagtgcag aacaaaatat gtgtgtgtgt atgcatgtgt    4080
atgtacacct atacacttat atacagtacc ccatgtgaag aaaaataagg gtacgtgtta    4140
tgcgcgtagt attatggttg ttattttttga gaatatatct agaaagataa aaagaaagt    4200 ggaaatagtt cttgcctctg gtgggaagtg ggactatgtg cctgatcaat agggaagtaa    4260
ggaacacttt tttttttttt tttaaacgg agttttttgct cttgttaccc aggttggagt    4320
gcaatggcgc gatcttagct cactgcaacc tctgcctccc aggttcaagc gattctgctg    4380
cctcagcctc ctgagtagct gggattatag gcatgcgcct ccacgcctgg ctaattttgt    4440
atttttagta aagatggggt ttctccatgt tggtcaggct ggtcttgaac tccccacctc    4500
aggtgatccg tccgcctcag cctcccaaag tgctaggatt acaggcgtga gccaccgtgc    4560
ctggccagga acgcttttta tttttgtacc tttaaaagtg tgtaccgtct gtgtatataa    4620
tcagttaaaa acaaagaaaa gctgagtgtg gtggctcatg cctgtaatcc cagcccttaa    4680
ggaggccgag gccggcggca gatcacctga ggtcaggagt tcaagaccgg cctgaccaaa    4740
acggtgaaaa ctcatctcta caaaaacata aaaattagcc aggcatgatg gcaagtgcct    4800
gtaatcccag ctggttggga ggctgaggtg ggagacttgc ttgaacctag gaggcagaga    4860
ttgcagtgag ccaagactgt accactgcac tccagcctgg gcaacagagc aagtctctgt    4920
ctcaaaacaa aaacaaaaac acaagaaaaa atgtaaaac aatttcatgc agtagcaagc    4980
atcgagttaa atacagttga cccttgaaca acacaggttt gaattgcacg ggtccattta    5040
tactcacatt tcttccacct ctgccacccc caaaatagca agaccaaccc catctctttt    5100
cctttctctt ccccctcctc agcctactca atgtgaagat gatgaggatg aaaacctttg    5160
tgatgatcca cttccactta atgaatggta atatgttttt ttcttactta tgattttctt    5220
agtagcattt tcttttctct agcttccttt attgtaaaaa tacagtatat aacacatatc    5280
acatacaaaa tgtgtgtaaa tggactgttt gctattgata agtattctgg taaacagtag    5340
actattagtt ttttttgttt tgtgacaagg tctccctctg tcgcccagcc tggaatgccg    5400
tggtgtgatc atggctcact gcagccaaaa acttctgggc taaagcaatc ctctactaaa    5460
aatacaaaaa ttagccaggc atggtggtgc gcttctgtaa tcccagctac tcaggaggct    5520
gaggcaggag aattgcttga acccgggagg cagaggttgc agtgagctga gattgcaccg    5580
ttgcattcca gcctggacaa cagagcgaga ctccatctcg aaaataaaat aataataata    5640
ataataataa taataataat aataataggg ctgggtgtgg tggctcatgc ctgtaatccc    5700
agcactttgg gaggccaagg tggacagatc acctgaggtc aggagtctca attaaaaat    5760 aaataggccg ggcacagtgg ctcatgccca taatcccagc actttgggag gccgaggtgg    5820
gcagatcacc tgaggtcagg agtttgagac cagcctggcc aacacggaga aacgctgcct    5880
ctatcaaaaa tacaaaaatt agctggatgt ggtggtgcat gctataatcc cagtaatacc    5940
agctactcgg aaggctgagg caggagaatc actcgaatcc gggacacgga ggttgcagtg    6000
agccgacatc atgccactgc gctccagcct gggtgacagt gagactctgt ctcagaaaaa    6060
aaaaaaaaaa aaaaaaaaa aaaaaaaaat atatatatat atatatatat atatatatat    6120
atatatatat gtgtgtatat atatatatat acacatatat gtgtgtatat atatatacac    6180
acacacatat atatgtgtat atataaaata aaataaataa taataaaaca tttactttgg    6240
```

```
ctgctgttgc tgcggggaga attgcagggt gtcaaaagta gcactggtgg aggggtagtg    6300
atcaaagtct ggtgctttag cccaaaggag aaatgataga gactcagact agctggtgat    6360
ggaggtagaa taagcataaa tgtatcaaaa agaggagttg atagatctta aagaatgatt    6420
ggatttgaag ggcaaaggaa gagaagaatc aaccaggtgg gttcagtgaa tgaaaccatc    6480
agaaacgaat tgtcccctga aatcaagact ttgtgattgc catagttgta tgcttctcaa    6540
aggttcctcg tctcctcttc cttggaccaa aagtcagagg caagaatgcc ctcattcata    6600
ccccagtggt ctatacctcc agcagcaagt cgagtgagca agtgatgtcc tgaaaggccc    6660
agtggatcag tggaatgaag cgggcaggaa gacttagtgc tcctgaaaca aggaatccag    6720
aatccaggag aaggatggct cagtggggct ttcaagggac aagtatgggg gttgaagggg    6780
tcactgtccc tataccaaat ccgaaaatat tgtgaccagg aaccattctg tccaactctt    6840
ctatttcagg tggcaaagca aagctatatt caagaccaca tgcaaagcta ctccctgagc    6900
aaagagtcac agataaaacg ggggcaccag tagaatggcc aggacaaacg cagtgcagca    6960
cagagactca gaccctggca gccatgcctg cgcaggcagt gatgagagtg acatgtactg    7020
ttgtggacat gcacaaaagt gaggtgagtc gcaggacaga agagtgcttt ttgtttcagc    7080
agagcagcct ggggagagat aaaagctact cctggggcct gggcctgcat tcctgagatg    7140
tgggtaagag gggcccaggg tcagagtgtc tggcaagctt ggctctgccc ctttgctgtc    7200
ctggagacta gggctaatcc tgggctcagg gagtggcctc cccatggtta ggatacaagt    7260
gctcatcaag ggccacccct aggaaggacc aatttttccta tcagaagctt ctaagttatc    7320
ctcctttggc ccaaagggac acctcaagcc tactctgagg aactctttcc aatgaactaa    7380
ttcctacagt cacttcccca gcaacctgtg cctcagcctc aaggcactgt ggggtaggcc    7440
tcagtttgtg gcctggacat cggactgtgg accagacgac tcctcccgat ttctgttgt    7500
tttcagtcct ctgaccccaa gctggctggt gaagtaggta gagggaggag actttggtgc    7560
atgcatacac acacacacac acacacacac acacacacac acacacacac acacacacac    7620
gtctcctgtg cccccagtc tccatggctg gtcaatgatt gactggcatt tcacaggccg    7680
ctggttgcag cccagcctg ttgacttaga ggtcaccctc ggaagctaga gccctgtcct    7740
gcctcttcag tgtcagtggt cactccactg cccacaggct ggggtcttgg gcaaaacaca    7800
cgcatctgcc ctgatctgag tttgctgccc tctgtcccgc agtcagcccc actctgttcc    7860
cactccctct ccccagcccc ctagctagac ccctctcacc agcaccccctt tcccttccct    7920
gagggtcccc ctcgctgtct ttgtccctca gacatcctct ttcctgggct ctcctgccag    7980
gccctgctgg agggacagtt aaggaggaaa tcgaatcagc agcgcccacc cctgccccc    8040
ttcctctcct cttgtcagac accagacgag gttttttcct ctggcttccc agctctgaat    8100
gggctcattc ttttcagag gctcggcccc tctcgagcct cctccccagg gcgtgagttc    8160
tgaccccagc tcctccccc atccccactc cagcccctc tccagcttgc tccaccctct    8220
ctaccgccca ccgggactgg gcattgtctg ccagtccggg tttcttcctg ggatttggga    8280
tgcagagagg atgggtttgc ttgggcgggg gggtggagag tgaaggggg aagcaggatc    8340
tttgtagagg gagggaccta cagttacctg gacttctttc tctgtctcc cctcttggta    8400
cccttgactg gggctcttga gggtaatggg tgaagccaaa tctgccatgg ctcagttccc    8460
agctcagctc tgtgaccttg ggaaagttcc tttagctcgt ggaatctcaa ggctcaaggt    8520
tcctcttctg caaaatgggg aatgataaca cctgcctcct ctggagtctt ggggactcag    8580
tgttctgagg aacgtggctg taggtcagag tggcacagag tagggtccaa tgaagcatgg    8640
```

```
cgtccacagt agctttcctg actggactaa cctttccgga cacaacagca gggcaggggt      8700
ggggcctggg gagaaaggac acctctaacc ctgatcctaa catcccgatg gcctctaagg      8760
ctgcctgcac actcatccag gtgcaagccc tccaaggtgt ggtgtgatga accagtgact      8820
cctggagcca ggtcagcgca tcctcttccc gcagggctgt aagctgcagg actgagaggc      8880
aggttgacca ggtcctgggc tggatgatgg ggtgagagta aggggtcagt tttgatacat      8940
gcccaacttt tctctctagc cctaagacat cctgggcaaa ttgcttacct cagttccnct      9000
gatcctcacc ctaaccctaa caccagctca agagaaaata gggatattga tggccatcca      9060
gaagggctgc tgtgttccat acacagcaat atttctcgaa tgtttgtgac agcggtccaa      9120
ggaataagtt aattttacat tatcactctg gataccgtga caaaactcca ccttatcctt      9180
actatatgaa tgtgctaggg ttgttttttt gttttgtttt ttttttttt ttttgagaca      9240 gagtttcgct cttgttgccc aggctggagt acaatggcgc gatcttggct caccgcaacc      9300
tccgcttccc aggttcaagc gattcacctg cctcagcctt cccgagtagc tgggattaca      9360
ggcatgcgcc accatgcccg gctaattttg tgtttttagt agagacaggg tttctccatg      9420
ttggtcaggc tggtaccaaa ctcccgacct caggtgatcc acctgccttg gcctcccaaa      9480
gtgctgcaat tacaggcatg agccaccgca cccagccgtg ctagggtctt tttctgttca      9540
attcctttct ctctcttgct ctcttttcttt ctttcaatgg agtcttactc tgtcacccag      9600
gctggagtgc agtggcaaga tctcagctca ctgcaacctc tgccctctga gttcaagcaa      9660
ttctcctgcc tcagcctccc gagtagctgg gattacaggt gcctgccacc acacctagtt      9720
aatttttgta cttttagtag agatgggggtt ttgtcatgtt ggccaggctg gtctcgaact      9780
cctgacctcg tgatctgcct gtcttggcct cccaaagtgc tgggattaca ggcatgagcc      9840
gccatactcg gccaactttg tattactttc ttaaagagag tttcccaaat tatataagct      9900
tcaggcccca caaaacctag atctgcccca gtataactaa atctgggacc atttattgag      9960
caattattat gtgccaagta ttgcgctgag tgcttccaga gcattatctc ctttaaccnc     10020
agcatagtat gtcagatgct gttttacaga tgagccaact gagaccagag atgctcagtc     10080
acttgcccaa ggtgacatga ctgatatgga atagagtcaa gatttttttt ttttttttg     10140 acacggagtc tcactctgtc tcccaggctg gagtgcagag gcgcaatctc agctcactgc     10200 aagtctgcc tccaggttc acgccattct cctgcctcag cctcctgagt agctgggact     10260
acaggcaccc gccaccacac ctggctaatt ttttgtattt ttagcagaga cagggtttca     10320
ccgtgttagc caggatggtc tcgatctcct gacctcgtga tctgcctgcc tcggcctccc     10380
aaagtgctgg aattacaggt gtgagccacc gcgactggcc agattcaaga tttgaaccca     10440
ggtcctcttg gtcccagagg ccctgtttc tcaactccct aggatggcat agcaacctgt     10500
cccacaagag gtgcctgctt taagtgtgct cagcacatgg aagcaagttt agaaatgcaa     10560
gtgtatacct gtaaagaggt gtgggagatg gggggggagg aagagagaaa gagatgctgg     10620
tgtccttcat tctccagtcc ctgataggtg cctttgatcc cttcttgacc agtatagctg     10680
cattcttggc tggggcattc aactagaac tgccaaattt agcacataaa aataaggagg     10740
cccagttaaa tttgaatttc agataaacaa tgaataattt gttagtataa atatgtccca     10800
tgcaatatct tgttgaaatt aaaaaaaaaa aaaaagtct tccttccatc cccaccccta     10860
ccactaggcc taaggaatag ggtcaggggc tccaaataga atgtggttga gaagtggaat     10920
taagcaggct aatagaaggc aaggggcaaa gaagaaacct tgaatgcatt gggtgctggg     10980
tgcctcctta aataagcaag aagggtgcat tttgaagaat tgagatagaa gtctttttgg     11040
```

```
gctgggtgca gttgctcgtg gttgtaattc cagcactttg ggaggctgag gcgggaggat    11100
cacctgaggt tgggagttca agaccagcct caccaacgtg gagaaaccct gtctttacta    11160
aaaatacaaa aaattagctg gtcatggtgg cacatgcctg taatcccagc tgctcgggag    11220
gctgaggcag gagaatcact tgaaccaggg aggcagaggt tgtggtgagc agagatcgcg    11280
ccattgctct ccagcctggg caacaagagc aaaagttcgt ttaaaaaaaa aaaaagtcc     11340 tttcgatgtg actgtctcct cccaaatttg tagaccctct taagatcatg cttttcagat    11400
acttcaaaga ttccagaaga tatgccccgg gggtcctgga agccacaagg taaacacaac    11460
acatccccct ccttgactat caattttact agaggatgtg gtgggaaaac cattatttga    11520
tattaaaaca aataggcttg ggatggagta ggatgcaagc tccccaggaa agtttaagat    11580
aaaacctgag acttaaaagg gtgttaagag tggcagccta gggaatttat cccggactcc    11640
gggggagggg gcagagtcac cagcctctgc atttagggat tctccgagga aaagtgtgag    11700
aacggctgca ggcaacccag gcgtcccggc gctaggaggg acgcacccag gcctgcgcga    11760
agagagggag aaagtgaagc tgggagttgc cactcccaga cttgttggaa tgcagttgga    11820
gggggcgagc tgggagcgcg cttgctccca atcacaggag aaggaggagg tggaggagga    11880
gggctgcttg aggaagtata agaatgaagt tgtgaagctg agattcccct ccattgggac    11940
cggagaaacc aggggagccc ccgggcagc cgcgcgcccc ttcccacggg gcctttact    12000 gcgccgcgcg cccggccccc accctcgca gcacccgcg ccccgcgccc tcccagccgg    12060
gtccagccgg agccatgggg ccggagccgc agtgagcacc atggagctgg cggccttgtg    12120
ccgctggggg ctcctcctcg ccctcttgcc cccggagcc gcgagcaccc aaggtgggtc    12180
tggtgtgggg aggggacgga gcagcggcgg gaccctgccc tgtggatgcc ccgccgaggt    12240
cccgcggccg gcggggccag aggggcccgg acgagctctc ctatcccgaa gttgtggaca    12300
gtcgagacgc tcagggcagc cgggccctgg ggccctcggg cgggaggggg cagttacacg    12360
gcagcggctc gagatggccc atccaagaga ctggcgcttt ccaggctccg aggggctccg    12420
ggaacttgtc aaagaagttc tctgaaattg ttcagaaagt tttcccgcaa agggtgtatt    12480
gcgtagagcg cgcgcgcgcg tttccccct tcttgagccc cctcaagctt tctcaaagcc    12540
tttccagttg gcagcctccg cctccggact ggcctgggct ggattccttg gggggtcct    12600 ctgcccctgcc cctcctccag cccctccccg ctcccctcca gacgattttg gtttggttgc    12660
tcctgcttct ggcggggtcg ggtgtgtgtg tgtgtggtgg agtggagggt ggcatagcaa    12720
cctgtcccaa ccagagccgg ggaggaaagg gtggcccgga gggtggcctc ttgctggggt    12780
ctgggttggg ggcggggag acgtttgctt tgaacagatt cttggggcca gcttagggac    12840
tgtgctctgt gacttttgga gcgcgtggac catggagggg tggggtggg tttcttgggg    12900 tgtaaagtgg gagagttccc agagaaggaa gctaagaaat aaggccagat gggagcctag    12960
ggagggctgc gttgttctgc tgccttttcc ttggtgctgt gcgtggggaa gggtgagtgg    13020
gggcagtgtg tatcctgacc catctgtcca cctgtgtgca ttaatcataa aagctaacat    13080
atagcctggg ccaggtatac tctgccagga actgtttgtg gtgttttgca tgcattctcc    13140
tttaatccta gaacacccct atagtggaag ttctgccagc attctggact gagtagcagt    13200
ccagaggttg agtagcagct agtaagtggt ggggtcaaga tgggacccca ggcagtgcga    13260
cccccaacca tgcattcgaa atcgctatat ggatgagtgc acctggagca atgagggaca    13320
ctgctccctg agtcactggg ctgcagggga gacaaaatga aagtgttctg ggagtcgtgg    13380
gtggtctcca taggtcagag ggtctgggga gggagtgggt gtcatcgtgg ctgtgtgttg    13440
```

-continued

```
cccgagggc cctctgtgag tgagtgcatg gccgtgttat ctctgcaggt ctacgccagg    13500
gtgttcctca gttgtgtggt ctttgtattt gtgtgtctgg gctttgtgtt gccaaacagc    13560
agtctctctg ctgacttggg gacacaggct gaactctgtc ctctgcagga actcccttaa    13620
ggtgctgggc cagatctgcc ataaacagag ggaggtagcc ttctatggcc acgccttctt    13680
gctgaggaag aaggttcctc tcttccaggg agtacatcct tgccctccct gtttcccaga    13740
caagcatctt cacctctcat cttctgatga aagggtgag gccatactga gctgtcaggc    13800
tgagctgctg cccttcctca ccttgggctg ggagttgatc agggaatggc agttgctgca    13860
gagctggatt tgagggctgg gttctctgga tggggcctcc tcatgtcctc acccctcaac    13920
ctgcactatt gattgtgttg tgcaggagtt agttaaaaag tcattgcaca gcctgggcaa    13980
caaggcaaaa ctctgtacaa aaatacaaa aattagttgg atgtgattac acgtgcctgt    14040
agtcccagct actccggagg ctgaggcagg aggatcacct gagcccagga agttgaggct    14100
tgcagtgagc tgtgattgca aatgctctcc agcctgggtg acagtgtgag actccgtttc    14160
agaaaaaaag tataccaccc agctgcctcc agcacccaga ttttacccaa ggggtgaggt    14220
ctggggcagg aatgtggggg aaggggaggc ctaggggag ccccagaggg gtcaggattt    14280
ttctgaaatc ctttcttaga ggtatgggtt ttacaaattg cagcaaatac atccttttaa    14340
tcttgcagaa ctccttcata tttttaattcc agtatgattc ttccaacagc ctcctctctt    14400
tactatactt ggggaaagta ctcatttttat ttgtcaagaa aaaacaatt gaaagatag    14460 ggatcaaatg taaaagaaa aaatacgtgg cattccaaag tcaaacacaa agcatgttta    14520
attttctcgt ggtttgggat tacccatatt cctgctgtat gaacctgtct tgtcttaact    14580
tttaagaaat gtacggtgta cttcctatat gctaggtttt tatccatgct ttcatttaat    14640
ctctgtgaca gtcctgtgaa gtaggtgcac agatgagaaa atggaagttc agagaaatga    14700
agcaacttat ccaaggctcc cagctaccca gtaatgtcca gggaattttt ggactctgaa    14760
gaggaggcat taagaggtgg ttagagtctt attccagcca acaataatgg gttgaacaaa    14820
gccttagggg caggcaggtg gccagatggg aggagaagcg ctcctcttgt tcaggcgaat    14880
gacctttcca tccacttctc taggctgtag aaagtggagc tgagctgggg gccctgaggt    14940
tccctcttga cttcagagtc ctctcccttc ctgtccagcc aatgcctgtc ttccttttgg    15000
gccctaccag catgacaggg ggctgcgggc aggaggggac agaggccacg ttgacacaca    15060
gggctgtggg tgagagagac agctgaagtg tcagcgtgag gggccagtgt ggggctgcgg    15120
ctgggagggc tggggtgggg cccagggtag ttgtgcctgt ccttgggtga tggaatgatc    15180
tggaaagaga ttccttccct gccctccacc tgtgagaagc ccctctagag tgacatctcc    15240
atcttatgtt tggccaccca tcctccccct gggaagagag ccgaggtggg gtaagggatg    15300
tgtactcttt caaggagtgg gagaattatt ctagcgaatg tttgtgttgt cccagttctg    15360
tttacaaagc ctcgtcatgt ttacagatgg ctgcgcaatt cattacctca tttaactctc    15420
atgtacctcc tctgagggag taagagctgt tacagccaag tttaggtcag taaatattca    15480
ccaagttgca ggtactgcag ggcatagaga tgaatccgat ttagcttctg ccctggaggt    15540
ctgggaactt gctcaagatc actcagtgag cagctgagct agggttctca actaaagacc    15600
ctgggcccag gccctggtct gatgtcaggc ctgatacacc aggtgtttgt ggtcggggaa    15660
tcccagtgtc acttgaatgg gctgtgcat tatgggtctg ggagagctga gctttgggga    15720
cacaggtcat tttactgtag tattcatgga aaccaaggga agtattggct ttctgctgt    15780 gagcaagagg agcagctggg gctgcaagct ggtggggagg agagaaccca cctgagagaa    15840
```

```
acctcaggac tggggtcaag tcctgaccac cagagtccag agagacatga aggactgtga   15900
ccagctctga gcagagagat ggattccatg acctcaactg gtcccttttg ttcggagact   15960
cgtgactgga cttcattcat ccactcattc attcattcac tcagcagaca cttatctagc   16020
gctccctgtg gctggtcctg cctcatactg tctttgctct ggagaattgg aggttggggt   16080
tcctgagggg cagggtcctg agacaagga cactcctggg tagaattagg acctaccccc   16140
caggaaatca acggggacca ggtgccgtgg ctcacacctg taatcccagc actttgggag   16200
gccgagacgg gcggatcaca aggtcagcag ttcaggacca gcctggccaa catggtgaaa   16260
cccgcctcaa ctaaaaatac aaaaattagc caggtgtggt gtcaggcacc cgtaatccca   16320
gctactgagg aggctgaggc aggagaattg cttgaacccg ggaggcagag gttgcagtga   16380
gccgagattg cgccactgca ctccagcctg gcgacagggc gagactccat ctcaaaaaaa   16440
gaaaaccaat gggacagggc agatatgggg acaatggtaa ggagatggga gagtgggagg   16500
gaggtgtcag gaagaccttc ttgacttcat gtaggctggt gggggtgtta gccagcaagc   16560
ctccagttcc ctgggaaccg ttctcagggt accaatttta ccacctgtct gcaaacactt   16620
taagattctt aatcagactc aaattggcca caaatcaggt aaacaaactc actagtgggg   16680
tggggctacc acccgttctg accctccagc ccaacccagc ccagccaccc tgccctccgt   16740
agagcctgtg tgtttatcg gtggcattgg gagaattagt gtgtatttat gttggcgtgg   16800
ggtgtggggt ggatttgtgt gtgtgcagtt aggcctagtg gaaggaatgt gggatctgaa   16860
ggcaggccag cctgagttcc agtcctgcct gttgctcaca agctttatga ggcgagagct   16920 aaccccctgcc agcctcagtt gtcttctttg caagatggag gttgcagccc cagtctctgg   16980
agcatgttat gcagatccac cgagagtgcc tgccaggcac acagtaggtg ctcagctcag   17040
ttactgtggc ggcccccact ccccattgtt gttgttttcc tattgcctgg cggccacagc   17100
tggtatccct tgaaaagggc tacaggggt ggagtcggac cctgccccag ccctgtggag   17160
accctgggct tgggccaggg cctggggtct gggcctgcag acagctgtgt ctataaagca   17220 gctgaaggc tgaggccggg ggaggtcctg gcagcagggc gttattttgg gcctggcctg   17280 ccaccccag ctcctgtttc tcttgggagt ctgttggggg aggaagtgtg gggaagagga   17340
gggggtgcaa gtgggtgagg catggagtgg ggaggcctcc ctcagggaca tggacccttg   17400
agttctattt ctgttcctcc ctcctgttcc tccctctttg tccttatctg cctagagagg   17460
tgggaataga ggccattctg agtatcacta ggagaccacc agtttgtggc cactggccac   17520
tggcccaggc agggaacctg ggggcttgcc ctaccagcct ctcccagcaa tctgaaggca   17580
gggggtacct cgtattaccc cctaggattt gaccttaggc tccaacttgc tgggagagca   17640
gtgcctctgg tgtcagaccc caagccagcc cttgtgctgt ccctgaatct gcatgtagcc   17700
tgtgggaggc ggagcagtga ccggcaggaa ttctgggcag ctcaggcacc tgtgggcctg   17760
agggtgccct ctgcccccac ccttccgatc tcctgggcaa gacacgccag gtgattcatc   17820
tcaccagagc agaaaaacaa gttcaactgg gcactttaat ctcccctcac tggcaggcct   17880
ggtgtgagct gctaccccgg cgccctcac cagggtgct ttacctcctc tagtattcct   17940
gaccttagtg ggcatttctg gtctcaggga taccaggctg gggtccaagt gggccaggtc   18000
tggcagttca gccctatgcc ccatggctga tggctcgcgc tgggcaggta tgcagggctg   18060
acgtagtgcc tttgtggcag cagtttcgtg gcacacattc tgccagctgg ttctggagtc   18120
ttgccctgag gaggtggcca gggtgagggt gccagcgcag gaacctttgg cgcatgcttc   18180
accctggcct gggatctgca gcctgggtcc agatgcccac aactggaatc tgacgctcct   18240
```

```
tttctcttca tgggggactc ccagaggtct ctgcaatgac cagagccccg gttgtcccat    18300
gcctcagctg caactccagc tgaccctcct tccccactct ctgggtggca ttacgggggt    18360
gtggatccct tgccaagagg ttggcatgtg ggtgtgctgg aatggcatag ggagaatgca    18420
ccgagtttgt ttgcttggga gaggggcagg gggtatccag aagattcatg attcgtcatc    18480
gcctctcttg ggggattttt accccttttgc cctgagttgt gcctttggga caaaggaagc    18540
ctttctttgc cagccaacac cctgtactgg cgggcgagct ccccagggct ggcacgctgg    18600
ggcagcctct gaatgcacag ggtgggccta gtcagaagaa gcctttcccc tgaaatccct    18660
ctacttccca agcacgcaag ctttctcctg ctgttaaacc tgcagtgtgc aagggacatg    18720
ggcggagggg tccttcagtc aggcttctcc ctgtctgagg tggcatgact tggagtgagt    18780
ttggatgggg tggccaggtc tgagaaggtc ccccgccagt gtcctctgac ccatctgctc    18840
tctcctgcca gtgtgcaccg gcacagacat gaagctgcgg ctccctgcca gtcccgagac    18900
ccacctggac atgctccgcc acctctacca gggctgccag gtggtgcagg gaaacctgga    18960
actcacctac ctgcccacca tgccagcct gtccttcctg caggtgaggc ccgtgggcaa    19020
cccagccagg ccctgcctcc agctgggctg agccctctgt ttacaggtgg gtggcagaag    19080
aaggtgccct gccttctgt ttcctctctt gttgtggttt ctcaaccagg aagtcctttc    19140
taacatctaa cccccattca ttttactgca gaatcagttg actctctcta taacgtggct    19200
ggccgaggtc atgtctggat gggatgcgtc tgtgtttccg ctaaatcttg tgctctcttg    19260
ccagcatgat catgtcccct gtccacctgc tccagccact atccctctcc cacttacagc    19320
agaagaaagg gctggtgaga aaggtggatt acaggcccac ttctgccact gacgagccct    19380
atgaatgtgg cctacacccc cttagcttca ctgggtctca gtttccctat ctgtatattg    19440
ggagcagttg tgaagctcag aagagaaatg tctgtgaaaa ggttatgaac aggagggaga    19500
gtggaaacca acctgctgga tcgtgtccac agaccctgga atggggccac atgcttggtt    19560
tgtcaaattg cagacgccgg ccgggtgcga tggctcatgc ctgtaatccc agcactttgg    19620
gaggccgagg cggacagatc acttgaggtc gggagttcga ccagcctg accaacatgg    19680 agaaaccccg tctctactga aaatacaaaa ttagccaggc atggtggcac atgcctataa    19740
tcccagctac ttgggaaggc tgaggcagga gaatcacttg aacctgggag acggaggttg    19800
tggtgagcct agatcgtgcc attgtactcc agcctgggca acaagagtga aactccgtct    19860 caaaaaaaa aaatttgcag acgccatccc atccaggcct ttgctttcac tgatgaagaa    19920
actgagatac agagagggca gggcacctgt tcggagttta tgaaatgccc ccccaccatt    19980
atctttcttg atcatataag aatctggtga ggcaaggtag ggcgtgatct ttatctctat    20040
tttatcgttt tatttaagcg ggaacaggac tgctcagtgg ctgggggcct tgcccaagat    20100
ctccaagtac tggggaaccc cagggaggcc ctgggggggtg gcagtgttcc tatttcagcc    20160
ccactctgct tccccctccc aggatatcca ggaggtgcag ggctacgtgc tcatcgctca    20220
caaccaagtg aggcaggtcc cactgcagag gctgcggatt gtgcgaggca cccagctctt    20280
tgaggacaac tatgccctgg ccgtgctaga caatggagac ccgctgaaca ataccacccc    20340
tgtcacaggg gcctccccag gaggcctgcg ggagctgcag cttcgaagcc tcacaggtgg    20400
ccttcaccgt cattgaaacc ttctcttggt tattcagagc tgaccagggc cactgctaac    20460 caggggagg ctttgtgtgc attagaaatg gtgtcccttc tggcagacg caggcagagc    20520 ccgggaagac gccctcagaa gattggaaaa agattcccct tcttcctggg aagttgtagc    20580
ttgcgtcagc acatataatt caatcgtgag aatgcaggct gggttttgc ccccacttgg    20640
```

```
ctgagtgaag tgtacagtga acaacctatg taactatttg ctggccctgg agccgactct   20700
gccccagagt ctgggtgcca ggtgctttgc ccgcatggcc catttcagtc acgctgcagt   20760
cctgtcagga aaaaatcagt gttattctca ttctacatat gagaaaactg aggcttgcag   20820
atataagggc caaagttac acagctagtg agtgatgggg ctgagtttca gactccacag    20880
tctcttaacc accaagcagc atgcccagag tagaggtgag aaggaaggag agagctgcgg   20940
tccacatgag catctggacc tagcatggac aactcactcc tccctggctc tcgctttgtt   21000
cttgttgcgg gtgtggtggt ggtgggactc aaagacggta aagatagctt tctctcctcc   21060
ctggggaatc tggggggttgt ttaaaaggcc tgctcctctt ttagaaggca ggagggcccc  21120
aagggaagca gaaggtgaca gaaggggaaa gggtcctctg atcattgctc accccacaga   21180
gatcttgaaa ggaggggtct tgatccagcg gaaccccccag ctctgctacc aggacacgat  21240
tttgtggaag gacatcttcc acaagaacaa ccagctggct ctcacactga tagacaccaa   21300
ccgctctcgg gcctgtaagc catgcccctc cctgctgcct cttctctcag acagcctgac   21360
cccagccgca aactcccaac ttacaaccca gtgcctgccc gccactgccc cagccgccta   21420
caccacccat ttcctccctc tctgtccctc ctgccatctc cctgtgcctc ttcatctctg   21480
gggttctctg tcttgtctcc ctctgcttat aggttgtgcc tctggtttgg gggcctctca   21540
gcctgtctgg gtccctccct tgctgtgcag ttggcctcgt ggcctctgct gctgtttgtg   21600
cctctctctg ttactaaccc gtcctctcgc tgttagacat ctctctcact gcctgtctct   21660
ggttctgtcc tcaggccacc cctgttctcc gatgtgtaag ggctcccgct gctggggaga   21720
gagttctgag gattgtcaga gccgtgagtc tcagggaggc ctggagtcag ggaagggag    21780
ggctggggcc gggtggaatg caggtgtcat acaggtgaca tgggaggggt gggataacag   21840
gcttgggatg tctcccctgg gccaggtagt ctccctagaa ggtgatgctg atgagggtct   21900
ggtgcccagg gcgccactca gccctcatcc tgccctttgc ccaacagtga cgcgcactgt   21960
ctgtgccggt ggctgtgccc gctgcaaggg gccactgccc actgactgct gccatgagca   22020
gtgtgctgcc ggctgcacgg gccccaagca ctctgactgc ctggtatgtg cctctgcttt   22080
gtgcccaatg tgctctaccc cccaggatgc aagggggtggg caccctgcct ggtactgccc   22140
tattgcccct ggcacaccag ggcaaaacag cacagtgaaa gccagccacc tgtcccccca   22200
ggcctgcctc cacttcaacc acagtggcat ctgtgagctg cactgcccag ccctggtcac   22260
ctacaacaca gacacgtttg agtccatgcc caatcccgag ggccggtata cattcggcgc   22320
cagctgtgtg actgcctgtc cctgtgagtg ccagggagaa acacagtttt ctcattttgg   22380
tggggaggtt tgtttctgta aatgggagca tatggggagc actgtctgca tcttgctttg   22440
agagctggtc atgacagttc ctgccgagct gccttgttct ttcaacagct gtggagcagg   22500
tggcagtaag gagaggcagc taagagccca gacttggag ccagactgcc tgggtttgaa    22560
acccagctct atcaattagt aggcacgtga ccctcttgct gtgcctcagt ttcctcatca   22620
gtaaaatggg ggcaagaata gtcccaactg cataagatgg ttataacatt tgaaagagtt   22680
aatatttgta aagctcttag aacggtgcct ggtatgtact aagtgctcct aaatgttagc   22740
ttttattcta tagcctggtg aggtcagttt tacctttcgt tttgttttg agaccgaatt    22800
tagttagctc tatcgcagtg gcgcgatctc ggctcactgc aacctccgcc tcccaggttc   22860
gtgctattct cgtgtctcag cctcctgagt agctgggatt acaggcgccc accaccatgc   22920
ctcgctaaat tttgtatttt tagtagagac agggtttcac cacgttggcc agactggtct   22980
cgaactcctg acttcaggcg atccacctgc ctcggcctct gaaagtgctg ggattacagg   23040
```

```
cgtgagccac tgcacccgga cttttttttt tttggcagag tctcgctcca ttgcccaggc   23100
tggagtgcag tggtgcaatt ttggctcact gcaacctctg ccttccgcat tcaagcaatt   23160
cttgtgcctc agactcttga gtaggtggaa ctacaggcat gcaccaccat ggctgggtaa   23220
tttttgtatt tttagtagag acggagtttc actatgttgg ccaagctggt ctcgaactcc   23280
tgacctcaag tgatccaccc gccttggtct cccaaagtgc tgggattaca ggcatgagcc   23340
atcgtgcctg gcctagctca gttttattta acagatcacc tatttactga tgggcgttta   23400
tggactgggc tcagacctgg ggaacctctt tcctcctctc acaggaacag gagtgggcct   23460
tcagatcctg gctgactgtg ttagggagag gacaaaatgt agagccagac catttgggtt   23520
caaatcctcg ctcctccact cactagcaca atgaccttga ataatttaca gaactctctg   23580
ctttggtctc cctttttgca aaatgggaat ctcacagtgc tgatcccgtc tggttgttgt   23640
gaggggtaaa tggatgtcag gtgctgatgc gtggtagggc atttaagtat tggttgatat   23700
tattcttctt gtgcctgggc acggtaatgc tgctcatggt ggtgcacgaa gggccagggt   23760
atgtggctac atgttcctga tctccttaga caactacctt tctacggacg tgggatcctg   23820
caccctcgtc tgccccctgc acaaccaaga ggtgacagca gaggatggaa cacagcggtg   23880
tgagaagtgc agcaagccct gtgcccgagg tacccactca ctgcccccga ggccagctgc   23940
agttcctgtc cctctgcgca tgcagcctgg cccagcccac cctgtcctat ccttcctcag   24000
accctcttgg gacctagtct ctgccttcta ctctctaccc ctggccccec tcagccctac   24060 aagtgtccct atatcccctg tcagtgtggg gaggggcccg gaccctgatg ctcatgtggc   24120
tgttgacctg tcccggtatg aaggctgaga cggccccttc cccacccacc cccacctcct   24180
cagtgtgcta tggtctgggc atggagcact tgcgagaggt gagggcagtt accagtgcca   24240
atatccagga gtttgctggc tgcaagaaga tctttgggag cctggcattt ctgccggaga   24300
gctttgatgg gtaagagtgg gcacgatgac ctgagacagt gtcagggcag acagagtcct   24360
gaggatccag atgtggcagc atctcttggg gatggcagga gacagaagtg ggggatcaa   24420 gaatgcaaag aaagcagatg ggagaccaga ggagcagggc ctttggtggg tgggggtgat   24480
tatttttgta aatgacatgc tatccgtgaa caaggacttg tatggaggtc agaccatcta   24540
gataaagtaa aattccctt gagttcatag cagctttatt caaaatatcc ccaaattgga   24600
aataactcaa atgtgcatca ctaggtgaag gaataaacaa gtggcagtgt atccatttgg   24660
tgaagttcta cttagcaacc aaaggaaatg aactaccgat acaacataaa tgaatctcag   24720
aaacattaca ttgagcaaaa gaagccagag acaagattcc atactgtctg atccccttta   24780
tgtgaggctc tgaaccgaaa aaaccactct gtggtgggag agatcagaac ggtggttgcc   24840
ccagggtggg gggcttcaaa agggaggcac acaaggacat ttctggggta atagaaatgc   24900
tctgtatagt gattggggta gtggatacat gagcgaatcc atttgtcaaa actcatcaaa   24960
ctgtgtgata agagtctgtg catttttatt atttcatttt attttttgag atagagtctc   25020
actctgtcag caggctggag tgcagtggta cgatcttggc tcactgcaac ctctgcctcc   25080
tggattcaag caattctcct gcctcagtct cctgagtagc tgggactaca ggtgtgtgcc   25140
accatgccca gctaatttt gtatttttaa tagagatggg gtttcaccat gttggcaagg   25200
atggtctcga tctcttgacg tcgtgatccg cccacctcag cctcccaaag tgctgggatt   25260
acaggcatga gccaccacac ccggtgcatt ttattgtata taagttatac ttcaataaga   25320
aatgaattgg ggccaggcac ggtggctcac gcctgtaatc ccagcacttt gggaggccga   25380
ggcaggcaga tcacttgagg tcaggagttc aagaccagcc tggccaacat ggtgaaaccc   25440
```

```
catctctact aaaaaatata aaaaattagc caggcttcct ggcatgcgcc tatcatccca    25500
gctacttggg aggctgaggc aggagaattg catgaactcg ggaggtggag gttgtagtga    25560
gctgagattt cgctattgca ctccagcctg ggcgacagag tgagaccctg tctcaaaaag    25620
aaaaaaaaaa aaaagggtca ggcgccgtgg tgcacacctg taatcccagc actttgggag    25680
gctgaagcag gaagattgct tgagcccagg aattcaagaa cagcgtgggc aacatagtga    25740
gatcccatct ctacaaaaaa acacaaaaaa ttagccgggc atggtggtac gcacctgtag    25800
tctcagctac tagggagact gaggtgggag aatcacctga gcctgggagg tggaggttgc    25860
agtgggttga aatcatgtca ctgtactcca gcctgggtga cagaatgaga ccctgtctca    25920 aaaaaaaaa aaaaaaaaaa attcccttc acacttcctt tacctccact cccctttcca    25980
gagggggcca tggttaacag tgtgtgtgtt cacctagacc gtttatgcat ctgtagacac    26040
acacacagtg aagtgtggtt ttcgtcgttt tggtggggag gttggtttct gtaaatggga    26100
acatataggg agcactgtct gcaccttgct ttgagagccg gtcatgacag ttcccattga    26160
actgccttgt tctttcaata gctgcagagc aggtggcggc aaggagaggc agctaagagc    26220
ccagacttgg gagccagact gcctgggttt gaaaccccggc tctaccactt actaggcatg    26280
tgacccttgt gctgtgcctc agtttcttca tctgtaaagt gggggcaaga acagtcccaa    26340
cttcataaga tggttatacc accatgcctg gccagatgat tataaagttt gaatgagtta    26400
atatttgtaa agctcttaga acagtgcctg gcagatacta ggtgctccta aatgttggtt    26460
tttattatgt ggctgggtgg ctcggggttt tatttaacag ctcccctatt tactaataga    26520
catttagatc atgttccatt ttcactctta caaacagttc cactttgtgt gtggctctgg    26580
gaacatgggc cagtgtctcc ctaggccaca ttcctagaaa taagatttct tttctttttt    26640
tttttttttt gagacagagt ctcgctttat cgccaggctg gtgtgcagta gtgtgatctc    26700
ggctcactgc aacctctgcc tcccgggttc aagtgattct cctgcctcag cctctcgagt    26760
aactgggact ataggcgcgc ggcaccacac ccagctaatt tttgtatttg tagtagagat    26820
ggggtttcac catgttggcc aggatggtct ccatctcttg acttcgtgat ccgcccgcct    26880
cggcctccca aagtgctggg attacaggcg tgagccactg agcccaggca gaataagat    26940 ttctagatca aaggatataa atactgtttt gatagatgtt gccgaactaa ggcctgggct    27000
ttgaagccca ggatgggaac agctgggctc gatgggcaaa gggtttgagt gaaggcattc    27060
atggtgggga gtggctggca tggccagtgc tgggagtgat gtccaccctg ttcctggccc    27120
tgctgactcc tctcctgacc cctccaggga cccagcctcc aacactgccc cgctccagcc    27180
agagcagctc caagtgtttg agactctgga agagatcaca ggtgggctct gtctctgcat    27240
cctgttctgc aggggctggg agtccttgtc ctgtccccac tcctttaatc tcaccctctg    27300
cctgcaggtt acctatacat ctcagcatgg ccggacagcc tgcctgacct cagcgtcttc    27360
cagaacctgc aagtaatccg gggacgaatt ctgcacaagt gagcactgag aaagaggggg    27420
cctgatgggg aggagtccca gggaggagtc cctgtgggaa gctttgggcc tgaggagta    27480 ctcctgtagc agtaaccttt ccatgaaagt ctgcagagtg tgctggggat ggaggaagat    27540
gagaatagcc tttgctgacc gggaagggggt ccgtggtaag gtgcccacct ttctcccata    27600
gtggcgccta ctcgctgacc ctgcaagggc tgggcatcag ctggctgggg ctgcgctcac    27660
tgagggaact gggcagtgga ctggccctca tccaccataa cacccacctc tgcttcgtgc    27720
acacggtgcc ctgggaccag ctctttcgga acccgcacca agctctgctc cacactgcca    27780
accggccaga ggacgagtgt ggtaagacag ggagcccagt gtgcgcactc cccatctgcc    27840
```

```
agcacacagc agtgcccagg gggccctggc agcagcgttc ttggacttgt gcagactgcc   27900
cgtctctgtg caccctctt gactcagcac agctctggct ggcttggcct cttggcatgg   27960
cttctctagc tgggtcctac ctgccttggc atccttccct ccccctctgt ttctgaaatc   28020
tcagaactct tcctctccct acatcggccc cacctgtccc caccctcca gcccacagcc    28080 atgcccacag ccagttccct ggttcacttg gacctggggc ctcccctaaa agtcccctgc   28140
ggtcccttcc tcctcactgc agtgggcgag ggcctggcct gccaccagct gtgcgcccga   28200
gggcactgct ggggtccagg gcccacccag tgtgtcaact gcagccagtt ccttcggggc   28260
caggagtgcg tggaggaatg ccgagtactg caggggtatg aggggcggag gagagggtgg   28320
ctggaggggt gcatggggct cctctcagac cccctcacca ctgtcccttc tctcaggctc   28380
cccagggagt atgtgaatgc caggcactgt ttgccgtgcc accctgagtg tcagccccag   28440
aatggctcag tgacctgttt tggaccggtg agctgctggc gggctcagag ctgggtggag   28500
gggggcagcg aggggggattg ccagggactt ggcaggatgg cgagatgcag tagggtgtgc   28560
tatctggtaa aatatccctg gagagggctc agcgctcaga cctgaacagc aacagagtgg   28620
cagaaaaggg gcctggggga cactggggcc cttcagacta tgaaaaggtt ctaaggaggt   28680
ctgtgttggt ggctgtgact gtggctgtgc tagggtggtg agccctgtgg gctcaggcgt   28740
cagactacct ggattcagac ccagctcctg cttccaacct tggttttta ttcctaaaat    28800 gggtattgta ataataccta ccttgctggg gtgtggcaag aatgaaatta aacagggctt   28860
ggcacagtga agcacgggaa aggctttcta cagagcagtg actgttgtta ctcgctgtta   28920
caccttaggt aatgcgtttt cctctctggg tgcctcccat tttctggctc aagtccctgc   28980
ccaggatcaa gcttggagga gggccccgag ggaggggcca cagagactgg gtgaagagca   29040
agggtgtttg tcccaggagc atggcgaaaa ttgctgctgg gtggccttgg gaagcacaaa   29100
ggggacccaa ctaagggcct gatcctactg ccctgggggt gtcagtgcca gccccccaca   29160
aatcttttct gcccccccca ggaggctgac cagtgtgtgg cctgtgccca ctataaggac   29220
cctcccttct gcgtggcccg ctgccccagc ggtgtgaaac ctgacctctc ctacatgccc   29280
atctggaagt ttccagatga ggaggcgca tgccagcctt gccccatcaa ctgcacccac    29340
tcgtgagtcc aacggtcttt tctgcagaaa ggaggacttt cctttcaggg gtctttctgg   29400
ggctcttact ataaagggg accaactctc cctttgtcat atcttgtttc tgatgacaaa    29460
aataacacat tgttaaaatt gtaaaattaa aacatgaaat ataaattaat gccctagcag   29520
ttctatcccc actgttaata atttgaaata ttttcctct agttatttt gtctgtgcac     29580 attctaatat gtatatataa gttaacatat attaatatta ttctccagtt atttttatct   29640
gtgcacattt taacacacac acacacacac acacacacac acatatgtat ttttagacgg   29700
agtttcactc tgtcgcccag gctggagtgc agtagtacaa tcttggctca ctgcagcctc   29760
cacctcctgg gtttaagcaa ttctcctgct tccgcctcct gagtagctgg gattacggga   29820
acgtgctacc ttgcctggct aatttttgta tttttagtac ataggatttc accatgttgg   29880
ccaggctggt ctcgaacccc tgacctcagg tgatctgcca gcctcggtcc cccaaagtgt   29940
tgggattaca gcggtgagcc accatgccca gtcatatatt tcttttaac aaatagaatc    30000 atagatcata catattgttt gcaaattgct ttttctcact ttccagaacc ttgaaatgtt   30060
tttccatgtt ctaacatggt gatctacctt attctttaa ttttttcttat ttagttgtct   30120 ttacacatga aacacatgaa tacatccttg tgataaacat tttcagtaac ataaaagtat   30180
aaatgttaca aagccaacgt gcccttttcac tcaactccct gtccacccag tctctcctgt   30240
```

```
ctgctgggag aaccaccgca ttgacttgtg tgttcaccct tccaggctct tttctgcaca   30300
cttatataga catactacat ttatattagg tcgagtcaaa taagattgct gtttgtgtaa   30360
accaaaaagt gtcaagagcc tgggcgcagt gactcacacc tgtaatccca gcactttggg   30420
aggctgaggc aggcagatca cttgagatca ggagttcgag accaatctgg ccaacatagc   30480 gagacccgt ctctactaaa aatacaaaaa ctagccaggt gtggtgatgc tgttctgcac    30540
tttgctttcc ccccgacttg aggtatcctt tcttgtgagt acagacggat ctaccacctt   30600 tattttttttt ttaattactc aacctgtaac atggatgtaa tttcactttg tttttgaggg  30660
atattgagct tgtttccctg ttttttgcagt ttattgcaat tgagctccac acacaagtga  30720
gccctctttt gtatgccccc tagtgggaat acagtgctgg caatgtttat cacaaggata   30780
tattcatgca tttcaattta aagacaacta aatgagaaaa attaaaagaa tatggatcca   30840
ggctgggcat ggtggctcac gcctgtaatc ccagcacttt gggaggccga ggcaggcaga   30900
tcacctgagg tcaggagttc aagaccagcc tggccaacat ggcaaaaccc cgtctctact   30960
aaaaatacaa aaattagcca ggcgtggtgg tgggcgcctg taatcccagc tatttgagag   31020
gttgagacag gagaattgct tgaacctggg cagcggaggt tgcagtgaga cgagattgca   31080
ccagtgcact ccaacctggg caacacagtg caactccttc tcaagaaaaa aagaaaaaa   31140 aaaaagaata tgggtccaga tccatatgga tcctagatcc agatcacggt gttagaacat   31200
ggaaaaacat tgcaagattc tgctaagtga aaaaagcatt tgcaaacagt atgtacagtc   31260
tatattcaga ggaggaactg ctgggtcata gatgatattt cataggtatt gccaaaccgt   31320
tctctggaga agtggtatgg gtttaccctg ggattcttct atggagggaa tagttgagct   31380
cccgggcttg ctcttctggg tgcccctccc cgcttcctat ccaccacaag gagctgcagg   31440
ggagcggggc atgccggttc cttggctgga aaggagtct ccttgtgagg tggtagaagg    31500
agcactgacg gccttgagcc cagtttctgc ctttgtcaaa tggggataat gacccagcca   31560
caccctcccc agggttgttg tgaggctgga aaggtggttc caagagggt ggttcccaga    31620 attgttgatg agactgtttc tcctgcagct gtgtggacct ggatgacaag ggctgccccg   31680
ccgagcagag agccaggttg gcctggaccc caggatgtac ccttcattgc ccttcactcc   31740
cccactggat gctgggtggt cactgctgta gggaggggac cccctgacat atgtcccttc   31800
ccacccactc ttccactgtg gaacctcctg tcattttcca cttcaccaag tgacagagga   31860
cctgctcaga tgctgagggg aggggactgc aaggaaagat ggctaggaaa cccagtccct   31920 ccacaccta gagtaacttg atgccttgtg agggacacag gcaaagttca attccttgga    31980
agtcaaggga gactgagaag agtacagctg cagcactgag ggagtgatga attcttaact   32040
ggggatggtg ggaggcttcg agtgggaggt ggcatttgag ctaggctttg agagaggagc   32100
aggtattgca cttgcattta ggtagaaagc attggggtgc aaggtgacac tggaggggga   32160
ggcatcagga aatccaggat gtcttcaaag ttctggtgtc gggggctgtt gagtaagcac   32220
aggaataagg gggtcaagtt agagtcaggg tggggtctga cctggatgcc ataggacctg   32280
atccccaagc cacagggtgg gacttgactg ggcagtgggg acctttggaa aggactttgg   32340
ggagaaaaac agactggagt ctgtcttagg cgatcatcgg tccgtgaaat gagcatgtgt   32400
tacaggcttg gtatgtacca gaccctgtgc taagcaaggg ggtatggaga ggagagggtg   32460
acaagaatat tggatcaaca cccgggagct ccatctatcc caggatgcac tatctttttt   32520
ttattttttt gagacggagt ctcactctgc ctgcaggctg gagtgcagtg gctccatctc   32580
ggttcactgc aacctctgcc tcctgggttc aagcgcttct tgtgcctcag cctcccaagt   32640
```

```
agctgggatt acaggcacat gccaccacac ccagctaatt tttgtatttt tagtagagac   32700
ggggtttcac catgttggcc aggatggtct cgatctcttg acctcaagat ccgcccacct   32760
tggcctccca aagtgctggg attacagaca tgagccaccg tgcccagcca gatacgctat   32820
ctttttattg agtgattgag acagggtctt gctctcttgt ccagtcttga atgtggtggt   32880
gtaatcacag gctcactgca gccttgacct cctgggctca agttacccett ctgcagtagc   32940 tgggactata ggagcgtgcc accacgcctg ggtaatttaa aaattttttt ttgtatagac   33000
agggtctcac tatgttgccc gagctggtct caaactcgtg ggctcaagtg atcctccagt   33060
tttggcctcc caaaatgttg ggatcacagg agtgagccac cactcctggc gatgagccaa   33120
gtcttttttt ttttttttttt tttttgatat ggagtcttgc tctgttgccc aggctggagt   33180
gcaatgacac gatcttggct cactgcaacc tctgcctccc aggttcaagc agttcaagca   33240
atcctcctgt ctcagccccc cagtagctgg gattacaggc atgcgctacc acgtccggct   33300 aattttttgta ttttttagtag agatgaggtt ttgccatgtt ggccaggctg gtcttgaact   33360
gctgacctca ggtgatccac ctgcctcggc ctcccaaagt gctgggatta caggtgtgag   33420
ccatcgtgcc tggcggagcc gagtcttaaa agatgaccct gtggagaaat ggtggtccag   33480
gctgaaggga cagcctatgc aaacactggg aggtgtggaa atcatgacc tgtgggtgga   33540 aattttggct agaacatcaa aatcatcagg tgtacattcc tgtacccatg cagcagtcag   33600
aatctctggg ggtggggccc caaaattgta tgcatacaga ctgtgtgctg atttgtgata   33660
ttacttagga ttttttgact ttacaatggt ggaaaagcaa taatatacat tcagtataaa   33720
ccgtactttg aatacccata cagccattct gttttttcact tttattttta tttatttatt   33780
tatttattat ttattttgag atgtcatttt gctgttgtta cccaggctgg agtgcaatgg   33840
cgcagtcttg gctcaccgca acctccacct ctcaggttca aacgattctc ctgcttcagc   33900
ctccagagtg gctgggatta caggcaggca ccaccacacc cggctaattt tgtattttta   33960
gtagagacgg ggtttctcca tgttagtcag gctggtctcg aactcgagag ctcaggtgat   34020
ctgcccatct cagcctcaag ccaccatgcc cagccctact ttcagtattc aataaattac   34080
atagccaggc accgtggctc acacctgtaa tcccagcact ttaggaggcc aaggtgggag   34140
gatcctttga ggccagaagc tcgagaccag cctgggcaac atagtgagac cccatttcta   34200
caaaaaataa aaaactagcc tgagtgtggt ggcgtgtgtc tgtagtccca gctacttggg   34260
cagctgaggt ggaaagactg cttgagccca gaggtcaggg ctgcagtggg ccatgatctc   34320
accactgcac tcagcctggg caacacagca aggccctgtc tcaaaaataa ataaataaat   34380
aacacaaact tatttaacag tttactataa aataggcttt gtgtcagatg attctgccca   34440
actgtaagct gctggcagtg taaatgttct gagcacgtgt aagccaggct aggtgtctta   34500
aatgcatttt cagtttcaac ttagaattgg tttatcagga cgtagcccct tggtgttgag   34560
gggcatgtgt attaacagtc tccttagtga ctttttttttt tttgagatgg agtcttgcac   34620
tggccgtagt gcagtggcac aatctcagct cactgcaacc tcttgtctcc cgggttcaag   34680
cgattctcct gcctcagtct cccaagtagc tgggattaca ggcacccaca ccacgcccag   34740 ctaattttttg tgtgtgtgta ttttttagtag agacgggggt tcactatgt tggccaggct   34800 ggtctcgaac tcctgaccctt gtgatctgcc cacctcagac tctcaaagtg ctaggattcc   34860
aggcatgagc caccgcgccc agagtcctta gtgatttttta caccatgaat tgttgaagcc   34920
ctaagccaga gccaagggca agagtataga gaatctggag atgcggagag ggttctgatt   34980
gcctacaagg agtttggact ttattgtgga ggcagcgggg agccaaggca ggttttagag   35040
```

```
taggagaggg tccaagcctg tgggtcaccc ttccgacttc cctttccgaa tgccaaacac    35100
cttcatgtcc cccgtgggcc ccctttgtcc ctcccacccc aaactagccc tcaatccctg    35160
accctggctt ccgcccccag ccctctgacg tccatcatct ctgcggtggt tggcattctg    35220
ctggtcgtgg tcttgggggt ggtctttggg atcctcatca agcgacggca gcagaagatc    35280
cggaagtaca cgatgcggag actgctgcag gaaacggagg tgaggcgggg tgaagtcctc    35340
ccagcccgcg tggggtctgc accggccccc ggcactgacc caccacccc tcacccagc      35400 tggtggagcc gctgacacct agcggagcga tgcccaacca ggcgcagatg cggatcctga    35460
aagagacgga gctgaggaag gtgaaggtgc ttggatctgg cgcttttggc acagtctaca    35520
aggtcagggc caggtcctgg ggtgggcggc cccagaggat ggggcggtg cctggagggg      35580 tgtggtcggc agttctgatg ggaggggcaa gagctggagg cagtgtttgg gggagggcag    35640
ttacagcgga gaagggagcg gggccaagcc ctagggtggt gaaggatgtt tggaggacaa    35700
gtaatgatct cctggaaggc aggtaggatc cagcccacgc tcttctcact catatcctcc    35760
tctttctgcc cagggcatct ggatccctga tggggagaat gtgaaaattc cagtggccat    35820
caaagtgttg agggaaaaca catccccaa agccaacaaa gaaatcttag acgtaagccc      35880 ctccacccte tcctgctagg aggacaggaa ggaccccatg gctgcaggtc tgggctctgg    35940
tctctcttca ttggggtttg gggagatatg actcccgcaa acctagacta ttttttttgga   36000 gacggagtct tgctctgtca cccaggctgg agtgcagtgg cgttatctcg gctcactgca    36060
acctccacct cctggactca agcgattttc atgcctcagg ctcctgagta gctgggatta    36120
caagcgcccg ctaatttttt tttttttttt gagacagagt ctcgctctgt cacccaggct    36180
agagtgaaat ggtgcggtct cagctcagcc tcccaggtta aagcgattct tctccctcag    36240
tctcctgagt agctgggatt acaggcgcga gccaccacgc ccggctaatt tttgtatttt    36300
tagtagagat gggatttcac catgttggcc aggttggtgt caaactcctg acctcatgat    36360
ccgcccgcct cggcctccca aagtgctggg attacaggtg tgagccaccg tgcccggcct    36420
aatctttgta ttttagtag agacagggtt tcaccatgtt gtccaggctg gtactttgag      36480
ccttcacagg ctgtgggcca tggctgtggt ttgtgatggt tgggaggctg tgtggtgttt    36540
gggggtgtgt ggtctcccat accctctcag cgtacccttg tccccaggaa gcatacgtga    36600
tggctggtgt gggctcccca tatgtctccc gccttctggg catctgcctg acatccacgg    36660
tgcagctggt gacacagctt atgccctatg gctgcctctt agaccatgtc cgggaaaacc    36720
gcggacgcct gggctcccag gacctgctga actggtgtat gcagattgcc aaggtatgca    36780
cctgggctct ttgcaggtct ctccggagca aacccctatg tccacaaggg gctaggatgg    36840
ggactcttgc tgggcatgtg gccaggccca ggccctccca gaaggtctac atgggtgctt    36900
cccattccag gggatgagct acctggagga tgtgcggctc gtacacaggg acttggccgc    36960
tcggaacgtg ctggtcaaga gtcccaacca tgtcaaaatt acagacttcg gctggctcg     37020 gctgctggac attgacgaga cagagtacca tgcagatggg gcaaggttag gtgaaggac     37080 caaggagcag aggaggctgg gtggagtggt gtctagccca tgggagaact ctgagtggcc    37140
acctccccac aacacacagt tggaggactt cctcttctgc cctcccaggt gcccatcaag    37200
tggatggcgc tggagtccat tctccgccgg cggttcaccc accagagtga tgtgtggagt    37260
tatggtgtgt gatggggggt gttgggaggg gtgggtgagg agccatggct ggagggagga    37320
tgagagctgg gatggggaga attacggggc cacctcagca tgtgaaggga gggaaggggc    37380
tgcctgtgcc ccaccttgca gggtctgtgc acttcccagg attagggaaa gaccgggtag    37440
```

```
ggtctgtctc ctggcatcac atctccccct gctacctgcc atgatgctag actcctgagc   37500
agaacctctg gctcagtaca ctaaagctcc ctctggccct cccactcctg acccgtctc    37560
tgccttaggt gtgactgtgt gggagctgat gacttttggg gccaaacctt acgatgggat   37620
cccagcccgg gagatccctg acctgctgga aaaggggag cggctgcccc agcccccat     37680
ctgcaccatt gatgtctaca tgatcatggt caaatgtgcg tggctgagct gtgctggctg   37740
cctggaggag ggtgggaggt cctggtgga ggagcccaca aggggcatga aggggacca     37800
ggatgtatgt agacccagga gccctagtat gttaggagcc tcaaaacctt cttgtatccc   37860
ttttacagtc aaagtccaaa gccactcttg aggaacactc ttgtacaaaa ttaagctggg   37920
cacagtggct catgcctgta atcccagtac ttttggaggc tgaggtggga ggatcccttg   37980
aagccaggag ttcaagacca gcctgggcaa catagtgaga tcctatctct acaaaaaata   38040
aaaaattat ctgggtgtgg tggtgtgtgc cagtagtccc agctactcag agaggctga     38100
ggcaggaaga tcacttgagc ctagtttaag gttgcagtaa gctatgattg caccactgaa   38160
atccagcctg ggtgacagag cgaaacctca tctcaaaaaa ataaaaaagc aaacaaaaag   38220
aaaaaaaaaa ttaaaaggga aactagaaga gatgccaaag gttctggctg aagaccccag   38280
agtctggtgc tacttctcta ccacctgagg gctttgggct gtcccttggg actgtctaga   38340
ccagactgga gggggagtgg gaggggagag gcagcaagca cacagggcct gggactagca   38400
tgctgacctc cctcctgccc caggttggat gattgactct gaatgtcggc caagattccg   38460
ggagttggtg tctgaattct cccgcatggc cagggacccc cagcgctttg tggtcatcca   38520
ggtactgggc ctctgtgccc catccctgcc tgtggctaag agcaccctcc tgcagagggt   38580
gggaaggaga gatgagtcca gtatgccagg cccctcacgg aaggctgcat gctgggctgg   38640
ggaggggcca ccatcctgcc tctccttcct ccacagaatg aggacttggg cccagccagt   38700
cccttggaca gcaccttcta ccgctcactg ctggaggacg atgacatggg ggacctggtg   38760
gatgctgagg agtatctggt accccagcag ggcttcttct gtccagaccc tgccccgggc   38820
gctgggggca tggtccacca caggcaccgc agctcatcta ccagggtcag tgccctcggt   38880
cacactgtgt ggctgtctgc ttacctcccc caaccccggt ggactagggt cccttttctct  38940
gatgttccct caactgtcac ctctcaagga aaccccatta tccctacaaa aaattcttac   39000
tgccttccaa cccctgtgac cccattctct ccacggtgac tgtgtcatac cccaaaggtg   39060
acctctgttt ttctcctgtg accctgtcac cttccatgga gtccccatcc cagatccgtg   39120
agtgaccccc atcatgactt tcttttcttgt ccccagagtg gcggtgggga cctgacacta   39180
gggctggagc cctctgaaga ggaggccccc aggtctccac tggcaccctc cgaagggct    39240
ggctccgatg tatttgatgg tgacctggga atggggcag ccaaggggct gcaaagcctc    39300
cccacacatg accccagccc tctacagcgg tacagtgagg accccacagt accctgccc    39360
tctgagactg atggctacgt tgcccccctg acctgcagcc cccagcctgg tatggagtcc   39420
agtctaagca gagagactga tgggcagggg aggtgggacc ttcagcccag gtccactgt    39480
gggggcagag ggagtggcag agacaccggg gttccttccc ctaatgggtc accttctctt   39540
gacctttcag aatatgtgaa ccagccagat gttcggcccc agccccttc gccccgagag    39600
ggccctctgc ctgctgcccg acctgctggt gccactctgg aaaggcccaa gactctctcc   39660
ccagggaaga atgggggtcgt caaagacgtt tttgccttttg ggggtgccgt ggagaacccc   39720
gagtacttga caccccaggg aggagctgcc cctcagcccc accctcctcc tgccttcagc   39780
ccagccttcg acaacctcta ttactgggac caggacccac cagagcgggg ggctccaccc   39840
```

-continued

```
agcaccttca aagggacacc tacggcagag aacccagagt acctgggtct ggacgtgcca    39900
gtgtgaacca gaaggccaag tccgcagaag ccctgatgtg tcctcaggga gcagggaagg    39960
cctgacttct gctggcatca agaggtggga gggccctccg accacttcca ggggaacctg    40020
ccatgccagg aacctgtcct aaggaacctt ccttcctgct tgagttccca gatggctgga    40080
aggggtccag cctcgttgga agaggaacag cactgggggag tctttgtgga ttctgaggcc   40140
ctgcccaatg agactctagg gtccagtgga tgccacagcc cagcttggcc ctttccttcc    40200
agatcctggg tactgaaagc cttagggaag ctggcctgag aggggaagcg gccctaaggg    40260
agtgtctaag aacaaaagcg acccattcag agactgtccc tgaaacctag tactgccccc    40320
catgaggaag gaacagcaat ggtgtcagta tccaggcttt gtacagagtg ctttctgtt     40380 tagtttttac ttttttttgtt ttgttttttt aaagatgaaa taaagaccca gggggagaat   40440
gggtgttgta tggggaggca agtgtggggg gtccttctcc acccactt tgtccatttg      40500 caaatatatt ttggaaaaca gct                                            40523
```

<210> SEQ ID NO 2
<211> LENGTH: 1255
<212> TYPE: PRT
<213> ORGANISM: Homo sapiens

<400> SEQUENCE: 2

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255
```

```
His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
        290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
        370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
        450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
        530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
        610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670
```

```
Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
            755                 760                 765

Asp Glu Ala Tyr Val Met Ala Gly Val Gly Ser Pro Tyr Val Ser Arg
770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
            835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
            915                 920                 925

Arg Glu Ile Pro Asp Leu Leu Glu Lys Gly Glu Arg Leu Pro Gln Pro
930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
            995                 1000                1005

Leu Glu Asp Asp Asp Met Gly Asp Leu Val Asp Ala Glu Glu Tyr
        1010                1015                1020

Leu Val Pro Gln Gln Gly Phe Phe Cys Pro Asp Pro Ala Pro Gly
        1025                1030                1035

Ala Gly Gly Met Val His His Arg His Arg Ser Ser Ser Thr Arg
        1040                1045                1050

Ser Gly Gly Gly Asp Leu Thr Leu Gly Leu Glu Pro Ser Glu Glu
        1055                1060                1065

Glu Ala Pro Arg Ser Pro Leu Ala Pro Ser Glu Gly Ala Gly Ser
        1070                1075                1080
```

```
Asp Val Phe Asp Gly Asp Leu Gly Met Gly Ala Ala Lys Gly Leu
    1085            1090            1095

Gln Ser Leu Pro Thr His Asp Pro Ser Pro Leu Gln Arg Tyr Ser
    1100            1105            1110

Glu Asp Pro Thr Val Pro Leu Pro Ser Glu Thr Asp Gly Tyr Val
    1115            1120            1125

Ala Pro Leu Thr Cys Ser Pro Gln Pro Glu Tyr Val Asn Gln Pro
    1130            1135            1140

Asp Val Arg Pro Gln Pro Pro Ser Pro Arg Glu Gly Pro Leu Pro
    1145            1150            1155

Ala Ala Arg Pro Ala Gly Ala Thr Leu Glu Arg Pro Lys Thr Leu
    1160            1165            1170

Ser Pro Gly Lys Asn Gly Val Val Lys Asp Val Phe Ala Phe Gly
    1175            1180            1185

Gly Ala Val Glu Asn Pro Glu Tyr Leu Thr Pro Gln Gly Gly Ala
    1190            1195            1200

Ala Pro Gln Pro His Pro Pro Ala Phe Ser Pro Ala Phe Asp
    1205            1210            1215

Asn Leu Tyr Tyr Trp Asp Gln Asp Pro Pro Glu Arg Gly Ala Pro
    1220            1225            1230

Pro Ser Thr Phe Lys Gly Thr Pro Thr Ala Glu Asn Pro Glu Tyr
    1235            1240            1245

Leu Gly Leu Asp Val Pro Val
    1250            1255

<210> SEQ ID NO 3
<211> LENGTH: 14
<212> TYPE: PRT
<213> ORGANISM: Homo sapiens

<400> SEQUENCE: 3

Lys Arg Arg Gln Gln Lys Ile Arg Lys Tyr Thr Met Arg Arg
1               5                   10

<210> SEQ ID NO 4
<211> LENGTH: 27
<212> TYPE: DNA
<213> ORGANISM: Artificial
<220> FEATURE:
<223> OTHER INFORMATION: PCR primer

<400> SEQUENCE: 4
atcgctagca tggagctggc ggccttg                                          27

<210> SEQ ID NO 5
<211> LENGTH: 27
<212> TYPE: DNA
<213> ORGANISM: Artificial
<220> FEATURE:
<223> OTHER INFORMATION: PCR primer

<400> SEQUENCE: 5
atcaagcttg atgaggatcc caaagac                                          27

<210> SEQ ID NO 6
<211> LENGTH: 30
<212> TYPE: DNA
<213> ORGANISM: Artificial
<220> FEATURE:
<223> OTHER INFORMATION: PCR primer
```

<400> SEQUENCE: 6
atcaagctta tgctgctgca ggaaacggag                                             30

<210> SEQ ID NO 7
<211> LENGTH: 29
<212> TYPE: DNA
<213> ORGANISM: Artificial
<220> FEATURE:
<223> OTHER INFORMATION: PCR primer

<400> SEQUENCE: 7
atcaccggta acactggcac gtccagacc                                              29

<210> SEQ ID NO 8
<211> LENGTH: 19
<212> TYPE: RNA
<213> ORGANISM: Artificial
<220> FEATURE:
<223> OTHER INFORMATION: siRNA sequence

<400> SEQUENCE: 8
gauggugcuu acucauuga                                                         19

<210> SEQ ID NO 9
<211> LENGTH: 21
<212> TYPE: RNA
<213> ORGANISM: Artificial
<220> FEATURE:
<223> OTHER INFORMATION: siRNA sequence

<400> SEQUENCE: 9
ggucaaauuu ccugaguugu u                                                      21

<210> SEQ ID NO 10
<211> LENGTH: 21
<212> TYPE: RNA
<213> ORGANISM: Artificial
<220> FEATURE:
<223> OTHER INFORMATION: siRNA sequence

<400> SEQUENCE: 10
gagcagagau gugggaaugu u                                                      21

<210> SEQ ID NO 11
<211> LENGTH: 21
<212> TYPE: RNA
<213> ORGANISM: Artificial
<220> FEATURE:
<223> OTHER INFORMATION: siRNA sequence

<400> SEQUENCE: 11
auaggcgaga cuacagacgu u                                                      21

<210> SEQ ID NO 12
<211> LENGTH: 19
<212> TYPE: DNA
<213> ORGANISM: Artificial
<220> FEATURE:
<223> OTHER INFORMATION: PCR primer

<400> SEQUENCE: 12
ttccggtggt ctggttcct                                                         19

```
<210> SEQ ID NO 13
<211> LENGTH: 24
<212> TYPE: DNA
<213> ORGANISM: Artificial
<220> FEATURE:
<223> OTHER INFORMATION: PCR primer

<400> SEQUENCE: 13
gagacacgat aggctccttc ctaa                                              24

<210> SEQ ID NO 14
<211> LENGTH: 21
<212> TYPE: DNA
<213> ORGANISM: Artificial
<220> FEATURE:
<223> OTHER INFORMATION: PCR primer

<400> SEQUENCE: 14
ggaaccttcg gtggtcttgt c                                                 21

<210> SEQ ID NO 15
<211> LENGTH: 24
<212> TYPE: DNA
<213> ORGANISM: Artificial
<220> FEATURE:
<223> OTHER INFORMATION: PCR primer

<400> SEQUENCE: 15
gaatggaaag ctgagaaaca gtga                                              24
```